(12) United States Patent
Lampe et al.

(10) Patent No.: US 9,309,198 B2
(45) Date of Patent: Apr. 12, 2016

(54) N-[3-(2-CARBOXYETHYL)PHENYL]PIPERIDIN-1-YLACETAMIDE DERIVATIVES AND USE THEREOF AS ACTIVATORS OF SOLUBLE GUANYLATE CYCLASE

(71) Applicant: Bayer Pharma Aktiengesellschaft, Berlin (DE)

(72) Inventors: Thomas Lampe, Düsseldorf (DE); Michael Hahn, Langenfeld (DE); Johannes-Peter Stasch, Solingen (DE); Karl-Heinz Schlemmer, Wuppertal (DE); Frank Wunder, Wuppertal (DE); Sherif El Sheikh, Köln (DE); Volkhart Min-Jian Li, Velbert (DE); Eva Maria Becker-Pelster, Wuppertal (DE); Friederike Stoll, Düsseldorf (DE); Andreas Knorr, Erkrath (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/402,232

(22) PCT Filed: May 17, 2013

(86) PCT No.: PCT/EP2013/060222
§ 371 (c)(1),
(2) Date: Nov. 19, 2014

(87) PCT Pub. No.: WO2013/174736
PCT Pub. Date: Nov. 28, 2013

(65) Prior Publication Data
US 2015/0152050 A1    Jun. 4, 2015

(30) Foreign Application Priority Data
May 22, 2012 (DE) .......................... 10 2012 208 530

(51) Int. Cl.
| | | |
|---|---|---|
| *C07D 211/14* | (2006.01) | |
| *C07D 217/04* | (2006.01) | |
| *C07D 221/06* | (2006.01) | |
| *A61K 31/445* | (2006.01) | |
| *A61K 31/451* | (2006.01) | |
| *A61K 31/472* | (2006.01) | |
| *C07D 221/20* | (2006.01) | |
| *C07D 211/06* | (2006.01) | |
| *C07D 211/18* | (2006.01) | |
| *C07D 211/46* | (2006.01) | |
| *C07D 295/15* | (2006.01) | |
| *A61K 31/438* | (2006.01) | |
| *A61K 45/06* | (2006.01) | |

(52) U.S. Cl.
CPC ............ *C07D 211/14* (2013.01); *A61K 31/438* (2013.01); *A61K 31/445* (2013.01); *A61K 31/451* (2013.01); *A61K 31/472* (2013.01); *A61K 45/06* (2013.01); *C07D 211/06* (2013.01); *C07D 211/18* (2013.01); *C07D 211/46* (2013.01); *C07D 217/04* (2013.01); *C07D 221/20* (2013.01); *C07D 295/15* (2013.01)

(58) Field of Classification Search
None
See application file for complete search history.

(56) References Cited

U.S. PATENT DOCUMENTS

| | | | |
|---|---|---|---|
| 5,041,453 A | 8/1991 | Huang et al. | |
| 5,693,650 A | 12/1997 | Müller et al. | |
| 5,811,429 A | 9/1998 | Connell et al. | |
| 5,935,984 A | 8/1999 | Goldmann et al. | |
| 6,667,334 B1 | 12/2003 | Neises et al. | |
| 6,693,102 B2 | 2/2004 | Stasch et al. | |
| 6,743,798 B1 | 6/2004 | Straub et al. | |
| 6,833,364 B1 | 12/2004 | Straub et al. | |
| 6,835,752 B2 | 12/2004 | Tani et al. | |
| 6,884,821 B1 | 4/2005 | Shinoda et al. | |
| 7,005,440 B1 | 2/2006 | Jayyosi et al. | |
| 7,173,037 B2 | 2/2007 | Alonso-Alija et al. | |
| 7,176,204 B2 | 2/2007 | Miyachi et al. | |
| 7,238,716 B2 | 7/2007 | Momose et al. | |
| 7,241,785 B2 | 7/2007 | Momose et al. | |
| 7,244,861 B2 | 7/2007 | Matsuura et al. | |
| 7,368,578 B2 | 5/2008 | Momose et al. | |
| 7,371,777 B2 | 5/2008 | Clark et al. | |
| 7,465,825 B2 | 12/2008 | Van Zandt et al. | |

(Continued)

FOREIGN PATENT DOCUMENTS

| | | |
|---|---|---|
| EP | 0 608 709 A1 | 8/1994 |
| EP | 0 638 553 A1 | 2/1995 |

(Continued)

OTHER PUBLICATIONS

International Search Report (PCT/ISA/210) mailed on Aug. 6, 2013, by the European Patent Office as the International Searching Authority for International Application No. PCT/EP2013/060222.

(Continued)

*Primary Examiner* — Zinna Northington Davis

(74) *Attorney, Agent, or Firm* — Buchanan Ingersoll & Rooney

(57) ABSTRACT

The present application relates to novel substituted 2-(piperidin-1-yl)acetamide derivatives, to processes for preparation thereof, to the use thereof for treatment and/or prevention of diseases, and to the use thereof for production of medicaments for treatment and/or prevention of diseases, especially for treatment and/or prevention of cardiovascular diseases.

10 Claims, No Drawings

(56) References Cited

U.S. PATENT DOCUMENTS

| | | |
|---|---|---|
| 7,491,748 B2 | 2/2009 | Tani et al. |
| 7,816,367 B2 | 10/2010 | Akerman et al. |
| 7,998,988 B2 | 8/2011 | Bartel et al. |
| 8,796,335 B2 | 8/2014 | Hahn et al. |
| 9,018,258 B2 | 4/2015 | Lampe et al. |
| 9,018,414 B2 | 4/2015 | Lampe et al. |
| 2003/0105097 A1 | 6/2003 | Simon et al. |
| 2005/0187266 A1 | 8/2005 | Su |
| 2005/0234066 A1 | 10/2005 | Bailey et al. |
| 2011/0034450 A1 | 2/2011 | Hahn et al. |
| 2011/0092554 A1 | 4/2011 | Chesworth et al. |
| 2011/0130445 A1 | 6/2011 | Lampe et al. |
| 2012/0028971 A1 | 2/2012 | Lampe et al. |

FOREIGN PATENT DOCUMENTS

| | | |
|---|---|---|
| EP | 1 229 010 A1 | 8/2002 |
| EP | 1 285 908 A1 | 2/2003 |
| EP | 1 939 189 A1 | 7/2008 |
| WO | WO 94/12181 A1 | 6/1994 |
| WO | 96/12473 A1 | 5/1996 |
| WO | 96/30036 A1 | 10/1996 |
| WO | WO 00/06568 A1 | 2/2000 |
| WO | WO 00/06569 A1 | 2/2000 |
| WO | 00/64888 A1 | 11/2000 |
| WO | 01/19778 A1 | 3/2001 |
| WO | WO 02/36553 A2 | 5/2002 |
| WO | WO 02/42301 A1 | 5/2002 |
| WO | WO 03/095451 A1 | 11/2003 |
| WO | 2004/099170 A2 | 11/2004 |
| WO | 2006/050097 A1 | 5/2006 |
| WO | 2006/055625 A2 | 5/2006 |
| WO | WO 2006/066948 A1 | 6/2006 |
| WO | WO 2011/051165 A1 | 5/2011 |

OTHER PUBLICATIONS

Demko et al., "Preparation of 5-Substituted 1H-Tetrazoles form Nitriles in Water," Journal of Organic Chemistry, (Nov. 3, 2011), vol. 66, No. 24, pp. 7945-7950.

Evgenov et al., "NO-independent stimulators and activators of soluble guanylate cyclase: discovery and therapeutic potential," Nature Reviews Drug Discovery, (Sep. 2006), vol. 5, No. 9, pp. 755-768.

Hayashi, "Rhodium-Catalyzed Asymmetric 1,4-Addition of Organoboronic Acids and Their Derivatives to Electron Deficient Olefins," Synlett, (2001), No. SI, pp. 879-887.

Hörig et al., "From Bench to Clinic and Back: Perspective on the 1st IQPC Translational Research Conference," Journal of Translational Medicine, (2004), vol. 2, No. 44, pp. 1-8.

Mase et al., "Synthesis of a Muscarinic Receptor Antagonist via a Diastereoselective Michael Reaction, Selective Deoxyflourination and Aromatic Metal-Halogen Exchange Reaction." Journal of Organic Chemistry, (2001), vol. 66, No. 20, pp. 6775-6786.

Moradi et al., "Palladium-Catalyzed R-Arylation of Esters," Journal of the American Chemical Society, (2001), vol. 123, No. 3, pp. 7996-8002.

Nossaman et al., "Stimulators and Activators of Soluble Guanylate Cyclase: Review and Potential Therapeutic Indications," Critical Care Research and Practice, (2012), vol. 2012, pp. 1-12.

Patani et al., "Bioisosterism: A Rational Approach in Drug Design," Chemical Reviews, (1996), vol. 96, No. 8, pp. 3147-3176.

Sakai et a., "Rhodium-Catalyzed Conjugate Addition of Aryl- or 1-Alkenylboronic Acids to Enones," Organometallics, (1997), vol. 16, No. 20, pp. 4229-4231.

Schäfer et al., "Failure is an Option: Learning from Unsuccessful Proof-of-Concept Trials," Drug Discovery Today, (Nov. 2008), vol. 13, No. 21/22, pp. 913-916.

Schmidt et al., "NO- and Haem-Independent Soluble Guanylate Cyclase Activators," Handbook of Experimental Pharmacology, (2009), vol. 191, pp. 309-339.

Stasch et al., "NO- and Haem-Independent Activation of Soluble Guanylyl Cyclase: Molecular Basis and Cardiovascular Implications of a new Pharmacological Principle," British Journal of Pharmacology, (Jul. 2002), vol. 136, No. 5, pp. 773-783.

Stasch et al., "Targeting the Heme-Oxidized Nitric Oxide Receptors for Selective Vasodilation of Diseased Blood Vessels," The Journal of Clinical Investigation, (Sep. 2006), vol. 116, No. 9, pp. 2552-2561.

Varchi et al., "Copper Catalyzed Conjugate Addition of Highly Functionalized Arylmagnesium Compounds to Enones," Tetrahedron, (Apr. 28, 2000), vol. 56, Issue 18, pp. 2727-2731.

Weintraub et al., "Syntheses of Steroidal Vinyla Ethers Using Palladium Acetate-Phenanthroline as Catalyst," Journal of Organic Chemistry, (1997), vol. 62, No. 5, pp. 1560-1562.

Wolfe et al., "Palladium-Catalyzed Amination of Aryl Halidesand Aryl Triflates: N-Hexyl-2-Methyl-4-Methoxyaniline and N-Methyl-N-(4-Chlorophenyl) Aniline," Organic Systems, Coll. (2004), vol. 10, pp. 423; (2002), vol. 78, pp. 23, (8 pages).

N-[3-(2-CARBOXYETHYL)PHENYL] PIPERIDIN-1-YLACETAMIDE DERIVATIVES AND USE THEREOF AS ACTIVATORS OF SOLUBLE GUANYLATE CYCLASE

This application is the national stage application (under 35 U.S.C. §371) of PCT/EP2013/060222 filed May 17, 2013, which claims benefit of German application 102012208530.0 filed May 22, 2012.

The present application relates to novel substituted 2-(piperidin-1-yl)acetamide derivatives, to processes for preparation thereof, to the use thereof for treatment and/or prevention of diseases, and to the use thereof for production of medicaments for treatment and/or prevention of diseases, especially for treatment and/or prevention of cardiovascular diseases.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be classified into two groups either by structural features or by the type of ligands: the particulate guanylate cyclases which can be stimulated by natriuretic peptides, and the soluble guanylate cyclases which can be stimulated by NO. The soluble guanylate cyclases consist of two subunits and contain one haem per heterodimer, which is part of the regulatory centre. This is of central importance for the activation mechanism. NO is able to bind to the iron atom of haem and thus markedly increase the activity of the enzyme. Haem-free preparations cannot, by contrast, be stimulated by NO. Carbon monoxide (CO) is also able to attack at the central iron atom of haem, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which may lead, for example, to hypertension, platelet activation, increased cell proliferation, endothelial dysfunction, atherosclerosis, angina pectoris, heart failure, thromboses, stroke and myocardial infarct.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attacks at the central iron atom of haem. In addition to the side effects, the development of tolerance is one of the crucial disadvantages of this mode of treatment [O. V. Evgenov et al., Nature Rev. Drug Disc. 5 (2006), 755].

Substances which directly stimulate soluble guanylate cyclase, i.e. without previous release of NO, have been identified in recent years. The indazole derivative YC-1 was the first NO-independent but haem-dependent sGC stimulator described [Evgenov et al., ibid.]. Based on YC-1, further substances were discovered which are more potent than YC-1 and show no relevant inhibition of phosphodiesterases (PDE). This led to the identification of the pyrazolopyridine derivatives BAY 41-2272, BAY 41-8543 and BAY 63-2521. Together with the recently published structurally different substances CMF-1571 and A-350619, these compounds form the new class of the sGC stimulators [Evgenov et al., ibid.]. A common characteristic of this substance class is an NO-independent and selective activation of the haem-containing sGC. In addition, the sGC stimulators in combination with NO have a synergistic effect on sGC activation based on a stabilization of the nitrosyl-haem complex. The exact binding site of the sGC stimulators at the sGC is still being debated. If the haem group is removed from the soluble guanylate cyclase, the enzyme still has a detectable catalytic basal activity, i.e., as before, cGMP is formed. The remaining catalytic basal activity of the haem-free enzyme cannot be stimulated by any of the stimulators mentioned above [Evgenov et al., ibid.].

In addition, NO- and haem-independent sGC activators were identified, with BAY 58-2667 being a prototype of this class. Common characteristics of these substances are that, in combination with NO, they have only an additive effect on enzyme activation, and that the activation of the oxidized or haem-free enzyme is markedly stronger than that of the haem-containing enzyme [Evgenov et al., ibid.; J. P. Stasch et al., Br. J. Pharmacol. 136 (2002), 773; J. P. Stasch et al., J. Clin. Invest. 116 (2006), 2552]. It is evident from spectroscopic investigations that BAY 58-2667 displaces the oxidized haem group which, as a result of the weakened iron-histidine bond, is attached only weakly to the sGC. It has also been shown that the characteristic sGC haem-binding motive Tyr-x-Ser-x-Arg is imperative both for interaction of the negatively charged propionic acids of the haem group and for the activity of BAY 58-2667. Against this background, it is assumed that the binding site of BAY 58-2667 to sGC is identical to the binding site of the haem group [J. P. Stasch et al., J. Clin. Invest. 116 (2006), 2552].

The compounds described in the present invention are likewise capable of activating the haem-free form of soluble guanylate cyclase. This is also confirmed by the fact that firstly these novel activators display no synergistic effect with NO at the haem-containing enzyme and secondly their action cannot be blocked by the haem-dependent inhibitor of soluble guanylate cyclase, 1H-1,2,4-oxadiazolo[4,3-a]quinoxalin-1-one (ODQ), but is even potentiated by this inhibitor [cf. O. V. Evgenov et al., Nature Rev. Drug Disc. 5 (2006), 755; J. P. Stasch et al., J. Clin. Invest. 116 (2006), 2552].

Accordingly, it was an object of the present invention to provide novel compounds which act as activators of soluble guanylate cyclase in the manner described above and can be used as such in particular for the treatment and prevention of cardiovascular disorders.

WO 94/12181-A1 discloses substituted aryl compounds as fibrinogen receptor antagonists for the prevention of thromboses and embolisms, and EP 0 638 553-A1 describes carboxamides having a terminal carboxyl group as antithrombotically active compounds. WO 02/36553-A2 discloses substituted phenylalkanecarboxylic acids as inhibitors of cell adhesion. WO 2006/066948-A1 describes piperidine derivatives having anti-inflammatory action. EP 1 939 189-A1 claims multicyclic compounds having PPAR-agonistic activity for the treatment of disorders of lipid metabolism. WO 2011/051165-A1 discloses phenylacetamido-substituted 3-phenylpropionic acids acting as activators of soluble guanylate cyclase.

The present invention provides compounds of the general formula (I)

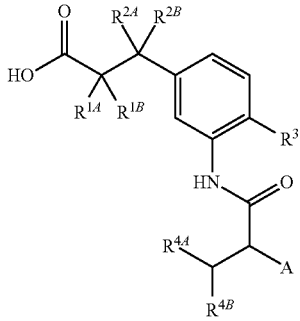

in which
R$^{1A}$ and R$^{1B}$ independently of one another represent hydrogen, methyl, ethyl or n-propyl
or
are attached to one another and together with the carbon atom to which they are attached form a cyclopropyl or cyclobutyl ring,
R$^{2A}$ represents hydrogen, methyl, ethyl, n-propyl, isopropyl, cyclopropyl, methoxy, ethoxy or cyclopropyloxy,
R$^{2B}$ represents hydrogen or methyl,
or
R$^{2A}$ and R$^{2B}$ are attached to one another and together with the carbon atom to which they are attached form a cyclopropyl or cyclobutyl ring,
R$^{3}$ represents hydrogen, fluorine, chlorine, methyl, trifluoromethyl or ethyl,
R$^{4A}$ and R$^{4B}$ independently of one another represent methyl, trifluoromethyl or ethyl
or
are attached to one another and together with the carbon atom to which they are attached form a cyclopropyl, cyclobutyl or cyclopentyl ring which may be substituted up to two times by fluorine
and
A represents an optionally substituted or fused piperidine ring of the formula

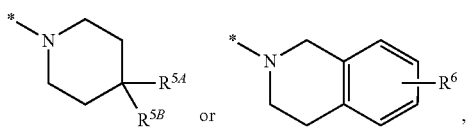

wherein
* denotes the point of attachment to the remainder of the molecule,
R$^{5A}$ represents hydrogen, (C$_1$-C$_4$)-alkyl, cyclopropyl, cyclobutyl, methoxy, ethoxy or phenyl, where (C$_1$-C$_4$)-alkyl for its part may be substituted up to three times by fluorine,
R$^{5B}$ represents hydrogen or methyl,
or
R$^{5A}$ and R$^{5B}$ are attached to one another and together with the carbon atom to which they are attached form a cyclopropyl or cyclobutyl ring, and
R$^{6}$ represents hydrogen, fluorine, chlorine, methyl or trifluoromethyl,
and their salts, solvates and solvates of the salts.

Compounds according to the invention are the compounds of the formula (I) and their salts, solvates and solvates of the salts, the compounds encompassed by formula (I) of the formulae mentioned below and their salts, solvates and solvates of the salts and the compounds encompassed by formula (I) and mentioned below as working examples, and their salts, solvates and solvates of the salts, if the compounds encompassed by formula (I) and mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for the isolation, purification or storage of the compounds according to the invention.

Physiologically acceptable salts of the inventive compounds include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, N,N-diisopropylethylamine, monoethanolamine, diethanolamine, triethanolamine, dimethylaminoethanol, diethylaminoethanol, procaine, dicyclohexylamine, dibenzylamine, N-methylmorpholine, N-methylpiperidine, arginine, lysine and 1,2-ethylenediamine.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^{2}$H (deuterium), $^{3}$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^{3}$H or $^{14}$C isotopes are suitable for this purpose. In addition, the incorporation of isotopes, for example of deuterium, can lead to particular therapeutic benefits as a consequence of greater metabolic stability of the compound, for example to an extension of the half-life in the body or to a reduction in the active dose required; such modifications of the compounds according to the invention may therefore in some cases also constitute a preferred embodiment of the present invention. Isotopic variants of the compounds according to the invention can be prepared by generally customary processes known to those skilled in the art, for example by the methods described below and the procedures reported in the working examples, by using corresponding isotopic modifications of the particular reagents and/or starting compounds therein.

In addition, the present invention also encompasses prodrugs of the compounds according to the invention. The term "prodrugs" refers here to compounds which may themselves be biologically active or inactive, but are converted while present in the body, for example by a metabolic or hydrolytic route, to compounds according to the invention.

The present invention comprises as prodrugs in particular hydrolysable ester derivatives of the carboxylic acids of the formula (I) according to the invention. These are to be understood as meaning esters which can be hydrolysed to the free carboxylic acids, as the main biologically active compounds, in physiological media, under the conditions of the biological tests described hereinbelow and in particular in vivo by enzymatic or chemical routes. ($C_1$-$C_4$)-alkyl esters, in which the alkyl group can be straight-chain or branched, are preferred as such esters. Particular preference is given to methyl, ethyl or tert-butyl esters.

In the context of the present invention, unless specified otherwise, the substituents are defined as follows:

In the context of the invention, ($C_1$-$C_4$)-alkyl represents a straight-chain or branched alkyl radical having 1 to 4 carbon atoms. Preferred examples include: methyl, ethyl, n-propyl, isopropyl, n-butyl, isobutyl, sec-butyl and tert-butyl.

In the context of the present invention, it is the case that for all radicals which occur more than once, their meaning is independent of the others. When radicals in the compounds according to the invention are substituted, the radicals may be mono- or polysubstituted, unless specified otherwise. Substitution by one or by two or three identical or different substituents is preferred. Substitution by one or by two identical or different substituents is particularly preferred.

Preference is given in the context of the present invention to compounds of the formula (I) in which
$R^{1A}$ represents hydrogen or methyl,
$R^{1B}$ represents hydrogen,
or
$R^{1A}$ and $R^{1B}$ are attached to one another and together with the carbon atom to which they are attached form a cyclopropyl or cyclobutyl ring, $R^{2A}$ represents hydrogen, methyl, ethyl, isopropyl or cyclopropyl,
$R^{2B}$ represents hydrogen,
or
$R^{2A}$ and $R^{2B}$ are attached to one another and together with the carbon atom to which they are attached form a cyclopropyl ring,
$R^{3}$ represents fluorine, chlorine or methyl,
$R^{4A}$ represents methyl,
$R^{4B}$ represents trifluoromethyl,
or
$R^{4A}$ and $R^{4B}$ are attached to one another and together with the carbon atom to which they are attached form a cyclopentyl ring which may be substituted up to two times by fluorine,
and
A represents an optionally substituted or fused piperidine ring of the formula

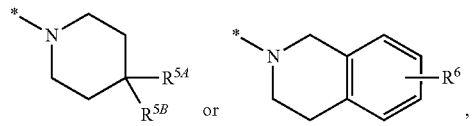

wherein
* denotes the point of attachment to the remainder of the molecule,
$R^{5A}$ represents hydrogen, methyl, trifluoromethyl, ethyl, isopropyl or cyclopropyl,
$R^{5B}$ represents hydrogen
or
$R^{5A}$ and $R^{5B}$ are attached to one another and together with the carbon atom to which they are attached form a cyclopropyl ring,
and
$R^{6}$ represents hydrogen or fluorine,
and their salts, solvates and solvates of the salts.

A particular embodiment of the present invention comprises compounds of the formula (I) in which
$R^{1A}$, $R^{1B}$, $R^{2A}$ and $R^{2B}$ each represent hydrogen,
and their salts, solvates and solvates of the salts.

A further particular embodiment of the present invention comprises compounds of the formula (I) in which
$R^{1A}$ represents methyl,
$R^{1B}$ represents hydrogen,
or
$R^{1A}$ and $R^{1B}$ are attached to one another and together with the carbon atom to which they are attached form a cyclopropyl ring,
and
$R^{2A}$ and $R^{2B}$ each represent hydrogen,
and their salts, solvates and solvates of the salts.

A further particular embodiment of the present invention comprises compounds of the formula (I) in which
$R^{2A}$ represents methyl,
and
$R^{1A}$, $R^{1B}$ and $R^{2B}$ each represent hydrogen,
and their salts, solvates and solvates of the salts.

A further particular embodiment of the present invention comprises compounds of the formula (I) in which
$R^{4A}$ represents methyl,
and
$R^{4B}$ represents trifluoromethyl,
and their salts, solvates and solvates of the salts.

A further particular embodiment of the present invention comprises compounds of the formula (I) in which $R^{4A}$ and $R^{4B}$ are attached to one another and together with the carbon atom to which they are attached form a cyclopentyl ring,
and their salts, solvates and solvates of the salts.

A further particular embodiment of the present invention comprises compounds of the formula (I) in which
A represents an optionally substituted piperidine ring of the formula

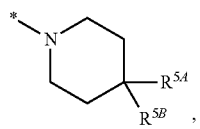

wherein
* denotes the point of attachment to the remainder of the molecule,
$R^{5A}$ represents hydrogen, methyl, trifluoromethyl, ethyl or cyclopropyl,
$R^{5B}$ represents hydrogen,
or
$R^{5A}$ and $R^{5B}$ are attached to one another and together with the carbon atom to which they are attached form a cyclopropyl ring,
and their salts, solvates and solvates of the salts.

In the context of the present invention, particular preference is given to compounds of the formula (I) in which
$R^{1A}$ represents hydrogen or methyl,
$R^{1B}$ represents hydrogen,
or
$R^{1A}$ and $R^{1B}$ are attached to one another and together with the carbon atom to which they are attached form a cyclopropyl ring,
$R^{2A}$ represents hydrogen or methyl,
$R^{2B}$ represents hydrogen,
$R^3$ represents fluorine or chlorine,
$R^{4A}$ represents methyl,
$R^{4B}$ represents trifluoromethyl,
and
A represents an optionally substituted piperidine ring of the formula

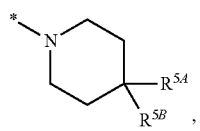

wherein
* denotes the point of attachment to the remainder of the molecule,
$R^{5A}$ represents hydrogen, methyl, trifluoromethyl or ethyl,
$R^{5B}$ represents hydrogen,
or
$R^{5A}$ and $R^{5B}$ are attached to one another and together with the carbon atom to which they are attached form a cyclopropyl ring,
and their salts, solvates and solvates of the salts.

The individual radical definitions specified in the particular combinations or preferred combinations of radicals are, independently of the particular combinations of the radicals specified, also replaced as desired by radical definitions of other combinations. Very particular preference is given to combinations of two or more of the abovementioned preferred ranges.

The invention furthermore provides a process for preparing the compounds of the formula (I) according to the invention, characterized in that a protected α-aminocarboxylic acid of the formula (II)

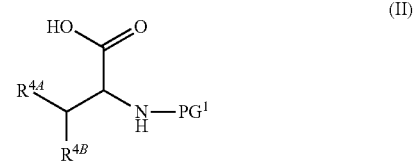

in which $R^{4A}$ and $R^{4B}$ have the meanings given above and
$PG^1$ represents a suitable amino protective group such as, for example, allyloxycarbonyl (Alloc), benzyloxycarbonyl (Z), tert-butoxycarbonyl (Boc) or 9-fluorenylmethoxycarbonyl (Fmoc),
is coupled in an inert solvent with the aid of a condensing agent in the presence of a base with an amine of the formula (III)

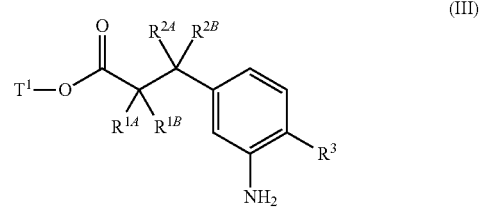

in which $R^{1A}$, $R^{1B}$, $R^{2A}$, $R^{2B}$ and $R^3$ have the meanings given above
and
$T^1$ represents $(C_1\text{-}C_4)$-alkyl or benzyl,
to give a carboxamide of the formula (IV)

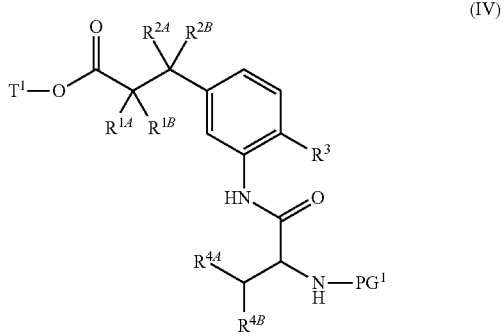

in which $PG^1$, $R^{1A}$, $R^{1B}$, $R^{2A}$, $R^{2B}$, $R^3$, $R^{4A}$, $R^{4B}$ and $T^1$ have the meanings given above, then, by removal of the protective group PG¹, the amine compound (V)

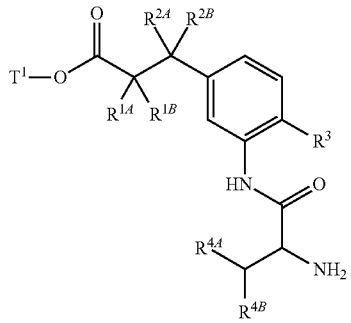

(V)

in which $R^{1A}$, $R^{1B}$, $R^{2A}$, $R^{2B}$, $R^3$, $R^{4A}$, $R^{4B}$ and $T^1$ have the meanings given above
is released, this is then reacted in the presence of a suitable reducing agent with a dialdehyde of the formula (VI)

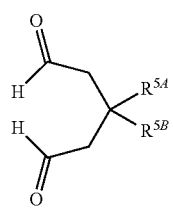

(VI)

in which $R^{5A}$ and $R^{5B}$ have the meanings given above
to give a mixture (with varying proportions) of the two cyclization products (VII) and (VIII)

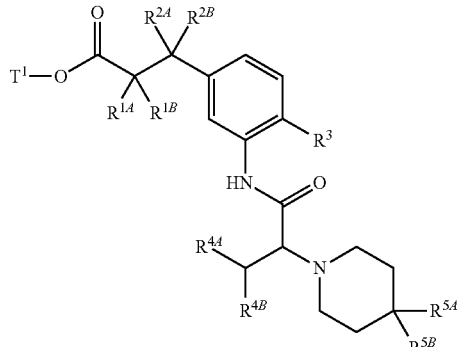

(VII)

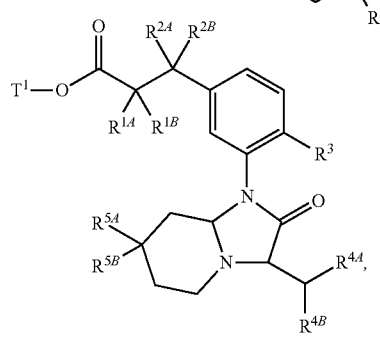

(VIII)

in which $R^{1A}$, $R^{1B}$, $R^{2A}$, $R^{2B}$, $R^3$, $R^{4A}$, $R^{4B}$, $R^{5A}$, $R^{5B}$ and $T^1$ have the meanings given above, this mixture is then treated with an excess of triethylsilane in trifluoroacetic acid so that the "wrong" cyclization product (VIII) is also converted into the desired target compound (VII), and the ester radical $T^1$ is finally removed by basic or acidic solvolysis or, in the case that $T^1$ represents benzyl, also by hydrogenolysis, giving the carboxylic acid of the formula (I-A)

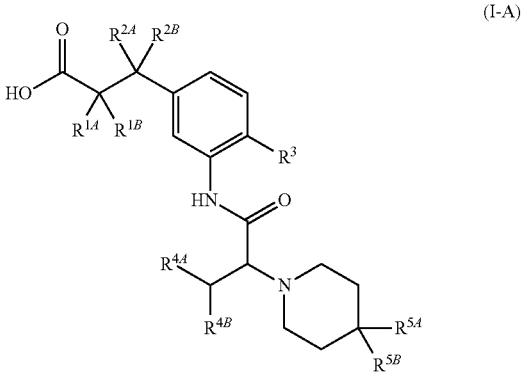

(I-A)

in which $R^{1A}$, $R^{1B}$, $R^{2A}$, $R^{2B}$, $R^3$, $R^{4A}$, $R^{4B}$, $R^{5A}$ and $R^{5B}$ have the meanings given above and the resulting compounds of the formula (I-A) are optionally separated by customary methods into their enantiomers and/or diastereomers and/or converted using the appropriate (i) solvents and/or (ii) bases or acids into the solvates, salts and/or solvates of the salts thereof.

Inert solvents for the process step (II)+(III)→(IV) [amide coupling] are, for example, ethers such as diethyl ether, diisopropyl ether, methyl tert-butyl ether, 1,2-dimethoxyethane, bis(2-methoxyethyl) ether, tetrahydrofuran or 1,4-dioxane, hydrocarbons such as benzene, toluene, xylene, pentane, hexane, heptane, cyclohexane or mineral oil fractions, halogenated hydrocarbons such as dichloromethane, trichloromethane, carbon tetrachloride, 1,2-dichloroethane, trichloroethylene or chlorobenzene, or dipolar aprotic solvents such as acetone, acetonitrile, ethyl acetate, pyridine, N,N-dimethylformamide (DMF), N,N-dimethylacetamide (DMA), dimethyl sulphoxide (DMSO), N-methylpyrrolidinone (NMP) or N,N'-dimethylpropyleneurea (DMPU). It is also possible to use mixtures of these solvents. Preference is given to using dimethylformamide or a mixture of dimethylformamide and pyridine.

Suitable condensing agents for this coupling reaction are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, α-chloroenamines such as 1-chloro-2-methyl-1-dimethylamino-1-propene, phosphorus compounds such as propanephosphonic anhydride, diethyl cyanophosphonate, bis(2-oxo-3-oxazolidinyl)phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate, or tertiary amine bases such as triethylamine, N-methylmorpholine, N-methylpiperidine, N,N-diisopropylethylamine, pyridine or 4-N,N-dimethylaminopyridine (DMAP). Preference is given to using O-(7-azabenzotriazol-1-yl)-N,N,N',N'-tetramethyluronium hexafluorophosphate (HATU) in combination with pyridine.

The reaction (II)+(III)→(IV) is generally carried out in a temperature range from 0° C. to +60° C., preferably at from +10° C. to +40° C.

Suitable protective groups $PG^1$ in compound (II) are customary amino protective groups such as, for example, allyloxycarbonyl (Alloc), benzyloxycarbonyl (Z), tert-butoxycarbonyl (Boc) or 9-fluorenylmethoxycarbonyl (Fmoc), where the protective group $PG^1$ is chosen such that the conditions of its removal in process step (IV)→(V) are compatible with the respective ester radical $T^1$ employed of compound (III) [see, for example, T. W. Greene and P. G. M. Wuts, *Protective Groups in Organic Synthesis*, Wiley, New York, 1999]. Preference is given to using the allyloxycarbonyl or the benzyloxycarbonyl group. Removal of the allyloxycarbonyl group is preferably effected using dimedone (5,5-dimethylcyclohexane-1,3-dione) in the presence of the tetrakis (triphenylphosphine)palladium(0) catalyst, whereas the benzyloxycarbonyl group is generally removed by hydrogenation (hydrogenolysis) in the presence of 5-10% palladium on activated carbon.

Reducing agents suitable for process step (V)+(VI)→(VII) [+(VIII)] are customary alkali metal borohydrides such as lithium borohydride, sodium borohydride or potassium borohydride, sodium cyanoborohydride or sodium triacetoxyborohydride. Preference is given to using sodium cyanoborohydride. The reaction is generally carried out in the presence of an acid/base mixture such as, for example, hydrochloric acid and triethylamine, in an alcoholic solvent such as methanol, ethanol or isopropanol. Depending on the reactivity of the respective components employed, the reaction is generally carried out in a temperature range from −20° C. to +60° C.

The "wrong" cyclization product of the formula (VIII) formed in varying proportions during the borohydride-mediated reaction of amine (V) with dialdehyde (VI) can likewise be converted by subsequent reduction with triethylsilane in trifluoroacetic acid as solvent into the desired cyclization product of the formula (VII) [cf., for example, D. N. Kursanov et al., *Synthesis* 1974, 633-651; U. Rosentreter, *Synthesis* 1985, 210-212], which, as a consequence, allows a higher yield of (VII) to be realized. This transformation can optionally be carried out after prior separation of the two cyclization products (VII) and (VIII), or it can advantageously be carried out using excess triethylsilane, directly with the purified product mixture obtained from the cyclization reaction.

Removal of the ester group $T^1$ in the process step (VII)→(I-A) is carried out by customary methods by treating the ester in an inert solvent with an acid or a base, where in the latter variant the salt initially formed is converted by subsequent treatment with an acid into the free carboxylic acid. In the case of the tert-butyl esters, ester cleavage is preferably carried out using acids. Benzyl esters are preferably cleaved by hydrogenation (hydrogenolysis) in the presence of a suitable catalyst such as, for example, palladium on activated carbon.

Suitable inert solvents for these reactions are water or the organic solvents customary for ester cleavage. These preferably include alcohols such as methanol, ethanol, n-propanol, isopropanol, n-butanol or tert-butanol, ethers such as diethyl ether, tetrahydrofuran, 1,4-dioxane or 1,2-dimethoxyethane, or other solvents such as acetone, acetic acid, dichloromethane, N,N-dimethylformamide or dimethyl sulphoxide. It is equally possible to use mixtures of these solvents. In the case of a basic ester hydrolysis, preference is given to using mixtures of water with dioxane, tetrahydrofuran, methanol and/or ethanol. In the case of the reaction with trifluoroacetic acid, preference is given to using dichloromethane, and in the case of the reaction with hydrogen chloride tetrahydrofuran, diethyl ether, dioxane, acetic acid and/or water.

Suitable bases are the customary inorganic bases. These include in particular alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate. Preference is given to lithium hydroxide, sodium hydroxide or potassium hydroxide.

Suitable acids for the ester cleavage are generally sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, optionally with addition of water. Preference is given to hydrogen chloride or trifluoroacetic acid in the case of the tert-butyl esters and to hydrochloric acid or sulphuric acid in the case of the methyl or ethyl esters.

The ester cleavage is generally carried out in a temperature range of from −20° C. to +100° C., preferably at from 0° C. to +60° C.

If the ester group $T^1$ in (VII) or (VIII) represents tert-butyl, under the conditions of the above-described treatment of (VIII) or the mixture of (VII) and (VIII) with triethylsilane and trifluoroacetic acid there is a simultaneous removal of this ester group so that the compound of the formula (I-A) according to the invention is obtained directly.

If appropriate, compounds of the formula (I) according to the invention can also be prepared by alkylating an α-aminocarboxylic acid of the formula (IX)

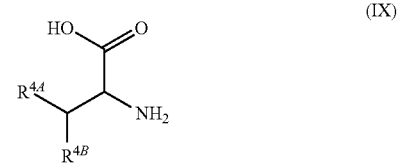

in which $R^{4A}$ und $R^{4B}$ have the meanings given above
in an inert solvent in the presence of a base with a compound of the formula (X)

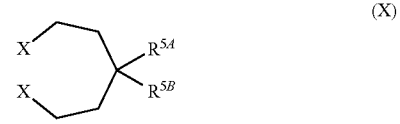

in which $R^{5A}$ und $R^{5B}$ have the meanings given above and

X represents a suitable leaving group such as, for example, chlorine, bromine, iodine, mesylate, tosylate or triflate, to give a compound of the formula (XI)

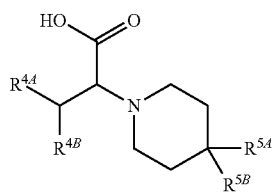
(XI)

in which $R^{4A}$, $R^{4B}$, $R^{5A}$, and $R^{5B}$ have the meanings given above, then coupling this in an inert solvent with the aid of a condensing agent in the presence of a base with an amine of the formula (III)

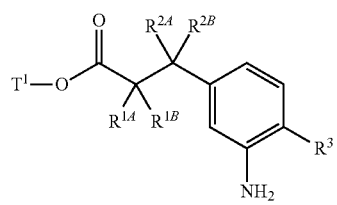
(III)

in which $R^{1A}$, $R^{1B}$, $R^{2A}$, $R^{2B}$ and $R^3$ have the meanings given above and $T^1$ represents $(C_1-C_4)$-alkyl or benzyl, to give a carboxamide of the formula (VII)

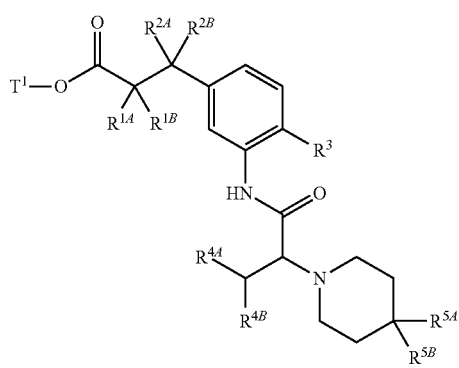
(VII)

in which $R^{1A}$, $R^{1B}$, $R^{2A}$, $R^{2B}$, $R^3$, $R^{4A}$, $R^{4B}$, $R^{5A}$, $R^{5B}$ and $T^1$ have the meanings given above, and then removing the ester radical $T^1$ as described above, giving the carboxylic acid of the formula (I-A)

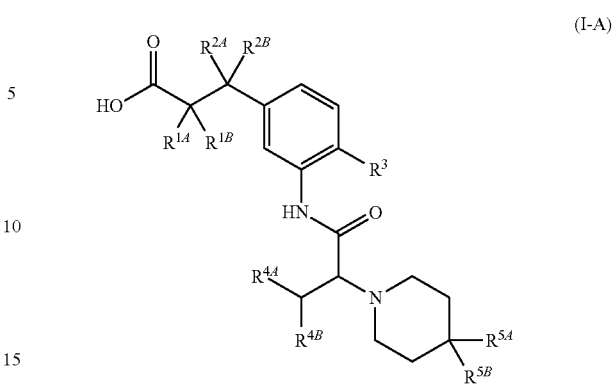
(I-A)

in which $R^{1A}$, $R^{1B}$, $R^{2A}$, $R^{2B}$, $R^3$, $R^{4A}$, $R^{4B}$, $R^{5A}$ and $R^{5B}$ have the meanings given above.

The alkylation reaction (IX)+(X)→(XI) is preferably carried out in water or in mixtures of water with water-miscible organic solvents such as methanol, ethanol, tetrahydrofuran, 1,4-dioxane, 1,2-dimethoxyethane, acetonitrile, N,N-dimethylformamide or dimethyl sulphoxide. Suitable bases are in particular alkali metal hydroxides such as, for example, lithium hydroxide, sodium hydroxide or potassium hydroxide, or alkali metal or alkaline earth metal carbonates such as lithium carbonate, sodium carbonate, potassium carbonate, calcium carbonate or caesium carbonate. Preference is given to using sodium hydroxide or potassium hydroxide. The reaction is generally carried out in a temperature range of from +50° C. to +150° C., preferably from +80° C. to +120° C.

The coupling reaction (XI)+(III)→(VII) is carried out under conditions analogous to those described above for the reaction (II)+(III)→(IV).

Compounds of the formula (I) according to the invention in which $R^{4A}$ and $R^{4B}$ are attached to one another and together with the carbon atom to which they are attached form a cyclobutyl or cyclopentyl ring can also be prepared by reacting a cycloalkenylboronic acid or ester of the formula (XII)

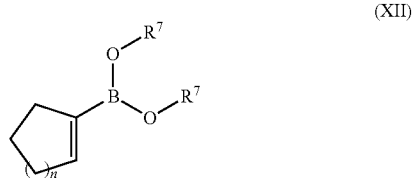
(XII)

in which n represents the number 0 or 1 and $R^7$ represents hydrogen or $(C_1-C_4)$-alkyl or the two radicals $R^7$ are attached to one another and together form a —$(CH_2)_2$—, —$C(CH_3)_2$—$C(CH_3)_2$—, —$(CH_2)_3$— or —$CH_2$—$C(CH_3)_2$—$CH_2$— bridge in the presence of a base with glyoxalic acid [OHC—COOH] and a piperidine derivative of the formula (XIII)

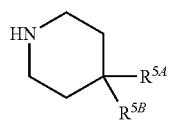

in which $R^{5A}$ und $R^{5B}$ have the meanings given above,
to give an α-piperidinocarboxylic acid of the formula (XIV)

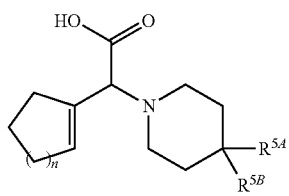

in which n, $R^{5A}$ und $R^{5B}$ have the meanings given above,
then coupling this in an inert solvent with the aid of a condensing agent in the presence of a base with an amine of the formula (III)

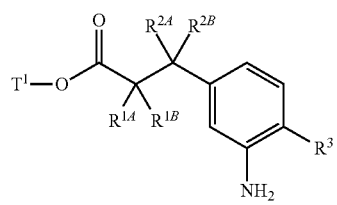

in which $R^{1A}$, $R^{1B}$, $R^{2A}$, $R^{2B}$ and $R^3$ have the meanings given above
and
$T^1$ represents $(C_1-C_4)$-alkyl or benzyl,
to give a carboxamide of the formula (XV)

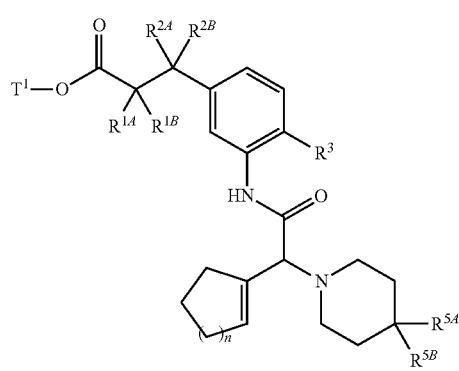

in which n, $R^{1A}$, $R^{1B}$, $R^{2A}$, $R^{2B}$, $R^3$, $R^{5A}$, $R^{5B}$ and $T^1$ have the meanings given above,
then hydrogenating in the presence of a suitable palladium or platinum catalyst to give a compound of the formula (XVI)

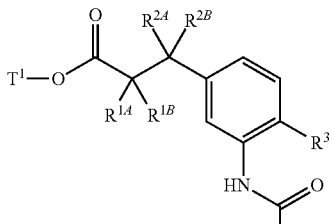

in which n, $R^{1A}$, $R^{1B}$, $R^{2A}$, $R^{2B}$, $R^3$, $R^{5A}$, $R^{5B}$ and $T^1$ have the meanings given above,
and finally cleaving the ester radical $T^1$ by basic or acidic solvolysis, giving the carboxylic acid of the formula (I-B)

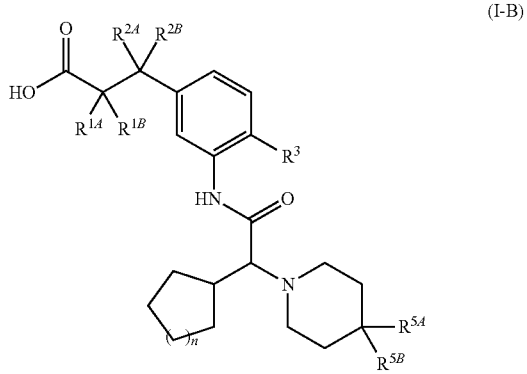

in which n, $R^{1A}$, $R^{1B}$, $R^{2A}$, $R^{2B}$, $R^3$, $R^{5A}$ and $R^{5B}$ have the meanings given above.

The preparation of the α-piperidinocarboxylic acid (XIV) from the cycloalkenylboronate (XII), glyoxalic acid and the piperidine derivative (XIII) is carried out analogously to a method described in the literature [see N. A. Petasis and I. A. Zavialov, J. Am. Chem. Soc. 119, 445-446 (1997)]. Here, the addition of a tertiary amine base such as, for example, triethylamine or N,N-diisopropylethylamine is advantageous.

The hydrogenation (XV)→(XVI) is generally carried out under a stationary hydrogen atmosphere at standard pressure or slightly elevated pressure. Suitable catalysts are in particular palladium or platinum on activated carbon (as carrier material) or platinum(IV) oxide. The reaction is carried out in an inert solvent customary for such purposes such as, for example, methanol, ethanol, tetrahydrofuran or ethyl acetate.

If the ester group $T^1$ in (XV) represents benzyl, under the hydrogenation conditions there is also a simultaneous removal of this ester group such that here, the compound of the formula (I-B) according to the invention is obtained directly.

The coupling reaction (XIV)+(III)→(XV) and the ester cleavage (XVI)→(I-B) are carried out under conditions analogous to those described above for the reactions (II)+(III)→(IV) and (VII)→(I-A).

Compounds of the formula (I-C) according to the invention

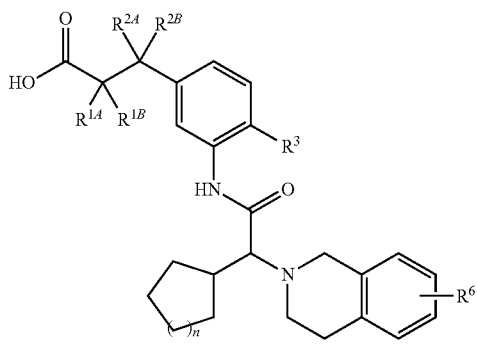
(I-C)

in which n, $R^{1A}$, $R^{1B}$, $R^{2A}$, $R^{2B}$, $R^3$ and $R^6$ have the meanings given above can be prepared in an analogous manner by employing, in the reaction sequence described above, instead of the piperidine derivative (XIII) a 1,2,3,4-tetrahydroisoquinoline of the formula (XVII)

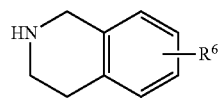
(XVII)

in which $R^6$ has the meaning given above.

The compounds of the formulae (I-A), (I-B) and (I-C) which can be prepared by the processes described above are in each case subsets of the compounds of the general formula (I) according to the invention.

Some of the α-aminocarboxylic acid intermediates of the formula (IX)

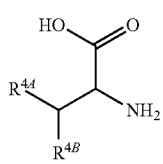
(IX)

in which $R^{4A}$ und $R^{4B}$ have the meanings given above are commercially available or described as such in the literature, or they can be prepared by known methods, for example by deprotonating a β,β-disubstituted carboxylic esters of the formula (XVIII)

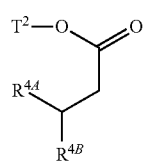
(XVIII)

in which $R^{4A}$ und $R^{4B}$ have the meanings given above and $T^2$ represents $(C_1\text{-}C_4)$-alkyl or benzyl, in an inert solvent with the aid of a base in the α-position, converting the product into the corresponding silyl enol ester (ketene acetal) and then brominating with N-bromosuccinimide to give the α-bromo derivative of the formula (XIX)

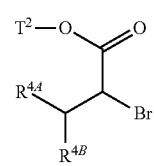
(XIX)

in which $R^{4A}$, $R^{4B}$ and $T^2$ have the meanings given above, subsequently reacting with sodium azide to give the compound of the formula (XX)

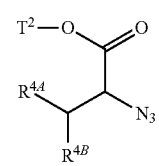
(XX)

in which $R^{4A}$, $R^{4B}$ and $T^2$ have the meanings given above, reducing this by catalytic hydrogenation to the α-amino acid ester of the formula (XXI)

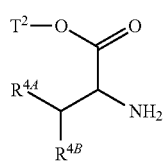
(XXI)

in which $R^{4A}$, $R^{4B}$ and $T^2$ have the meanings given above, and finally removing the ester radical $T^2$ by basic or acidic solvolysis or, in the case that $T^2$ represents benzyl, also by hydrogenolysis, giving the α-aminocarboxylic acid (IX).

The protected α-aminocarboxylic acid intermediates of the formula (II)

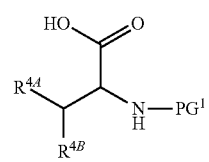
(II)

in which $R^{4A}$ and $R^{4B}$ have the meanings given above and $PG^1$ represents an amino protective group such as, for example, allyloxycarbonyl (Alloc), benzyloxycarbonyl (Z), tert-butoxycarbonyl (Boc) or 9-fluorenylmethoxycarbonyl (Fmoc)

are easily accessible by introduction of the respective protective group $PG^1$ at the stage of the α-aminocarboxylic acid (IX) or of the corresponding ester (XXI) (with subsequent removal of the $T^2$ radical).

Suitable for the α-deprotonation of the carboxylic ester (XVIII) are in particular non-nucleophilic strong bases such as, for example, sodium tert-butoxide or potassium tert-butoxide, sodium hydride or potassium hydride, lithium diisopropylamide or lithium bis(trimethylsilyl)amide, sodium bis(trimethylsilyl)amide or potassium bis(trimethylsilyl)amide; preference is given to using lithium diisopropylamide. The inert solvents employed are usually ethers such as diethyl ether, diisopropyl ether, methyl tert-butyl ether, tetrahydrofuran, 1,2-dimethoxyethane or bis(2-methoxyethyl) ether.

Following in situ conversion of the deprotonated ester into the silyl enol ester by addition of trimethylsilyl chloride, the bromination to (XIX) is preferably carried out using N-bromosuccinimide (NBS). The reaction sequence is advantageously carried out as a one-pot process and generally takes place in a temperature range of from −80° C. to +25° C.

The substitution reaction to give the azide compound (XX) is carried out by standard methods, for example by treatment with sodium azide in a dipolar aprotic solvent such as N,N-dimethylformamide. The subsequent reduction to the α-amino acid ester (XXI) is preferably carried out by hydrogenation in the presence of a palladium on activated carbon catalyst in an alcoholic solvent such as methanol or ethanol.

The removal of the ester group $T^2$ in the process step (XXI)→(IX) is carried out in a manner analogous to that described above for the ester radical $T^1$. Here, in the case that the ester group $T^2$ in (XX) represents benzyl, under the conditions of the hydrogenation (XX)→(XXI) there is likewise a simultaneous removal of this ester group so that the target compound (IX) is obtained directly.

The introduction of the protective group $PG^1$ at the stage of the α-aminocarboxylic acid (IX) or the corresponding ester (XXI) is carried out by generally customary methods [see, for example, T. W. Greene and P. G. M. Wuts, *Protective Groups in Organic Synthesis*, Wiley, New York, 1999].

Depending on their substitution pattern, the intermediates of the formula (III) can be prepared, for example, by either

[A-1] reacting a phosphonoacetic ester of the formula (XXII)

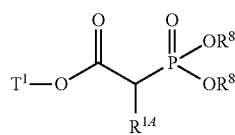

(XXII)

in which $R^{1A}$ and $T^1$ have the meanings given above
and
$R^8$ represents $(C_1-C_4)$-alkyl
in an inert solvent in a base-induced olefination reaction with a 3-nitrobenzoyl compound of the formula (XXIII)

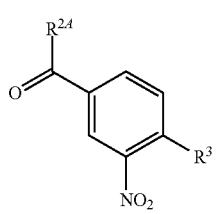

(XXIII)

in which $R^{2A}$ and $R^3$ have the meanings given above to give a compound of the formula (XXIV)

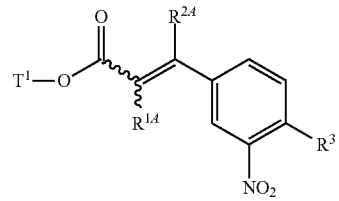

(XXIV)

in which $R^{1A}$, $R^{2A}$, $R^3$ and $T^1$ have the meanings given above, and then hydrogenating this in the presence of a suitable palladium or platinum catalyst to give a 3-(3-aminophenyl)propionic ester of the formula (III-A)

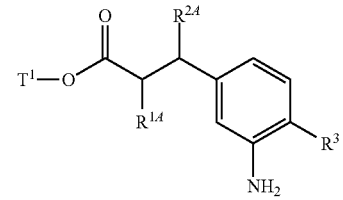

(III-A)

in which $R^{1A}$, $R^{2A}$, $R^3$ and $T^1$ have the meanings given above, or

[A-2] reacting a phosphonoacetic ester of the formula (XXII)

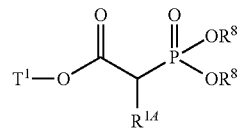

(XXII)

in which $R^{1A}$ and $T^1$ have the meanings given above
and
$R^8$ represents $(C_1-C_4)$-alkyl
in an inert solvent in a base-induced olefination reaction with a protected 3-aminobenzoyl compound of the formula (XXV)

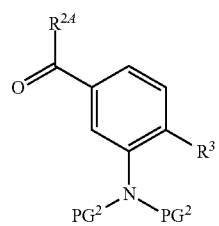

(XXV)

in which $R^{2A}$ and $R^3$ have the meanings given above
and
$PG^2$ represents benzyl or 4-methoxybenzyl as inert amino protective group, to give a compound of the formula (XXVI)

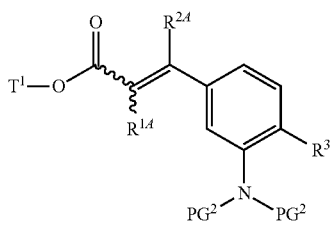
(XXVI)

in which PG², R¹ᴬ, R²ᴬ, R³ and T¹ have the meanings given above, then either (i) reducing with magnesium in methanol to give a compound of the formula (XXVII)

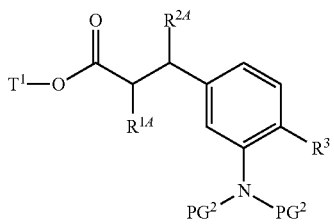
(XXVII)

in which PG², R¹ᴬ, R²ᴬ, R³ and T¹ have the meanings given above, and then removing the amino protective groups PG² by customary methods by hydrogenolysis or oxidatively affording the 3-(3-aminophenyl)propionic ester of the formula (III-A)

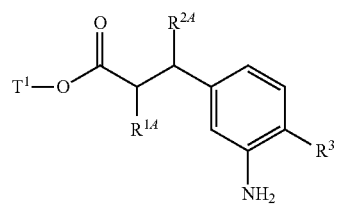
(III-A)

in which R¹ᴬ, R²ᴬ, R³ and T¹ have the meanings given above, or (ii) converting the compound of the formula (XXVI) in a one-step process by hydrogenation in the presence of a suitable palladium or platinum catalyst into the 3-(3-aminophenyl)propionic acid ester of the formula (III-A), or

[B] coupling an acrylic ester derivative of the formula (XXVIII)

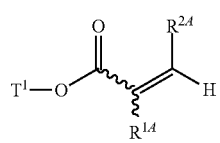
(XXVIII)

in which R¹ᴬ, R²ᴬ and T¹ have the meanings given above, in an inert solvent under palladium catalysis with a 3-amino- or 3-nitrophenyl bromide of the formula (XXIX)

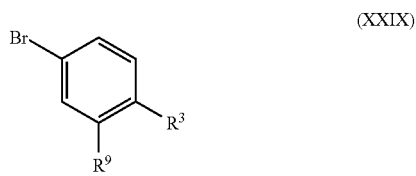
(XXIX)

in which R³ has the meaning given above and

R⁹ represents amino or nitro, to give a compound of the formula (XXX)

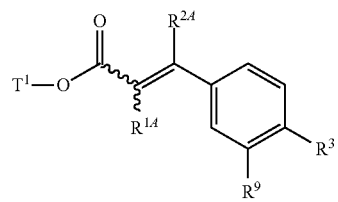
(XXX)

in which R¹ᴬ, R²ᴬ, R³, R⁹ and T¹ have the meanings given above, and then reducing this with hydrogen in the presence of a suitable palladium or platinum catalyst or in the case that R⁹ represents amino alternatively with magnesium in methanol to give the 3-(3-aminophenyl)propionic acid ester of the formula (III-A)

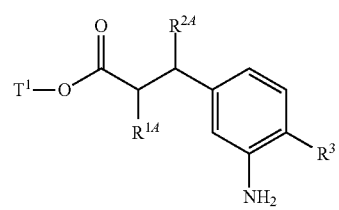
(III-A)

in which R¹ᴬ, R²ᴬ, R³ and T¹ have the meanings given above, or

[C] alkylating a carboxylic ester of the formula (XXXI)

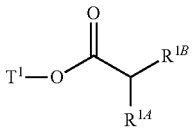
(XXXI)

in which R¹ᴬ, R¹ᴮ and T¹ have the meanings given above, in an inert solvent after α-deprotonation with a 3-bromobenzyl compound of the formula (XXXII)

(XXXII)

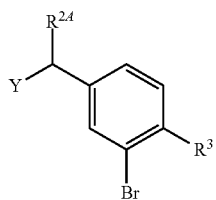

in which $R^{2A}$ and $R^3$ have the meanings given above
and
Y represents a suitable leaving group such as chlorine, bromine, iodine, mesylate, triflate or tosylate,
to give a compound of the formula (XXXIII)

(XXXIII)

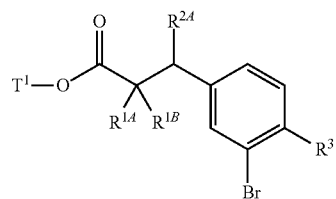

in which $R^{1A}$, $R^{1B}$, $R^{2A}$, $R^3$ and $T^1$ have the meanings given above,
subsequently reacting with benzylamine in the presence of a base and a palladium catalyst to give a compound of the formula (XXXIV)

(XXXIV)

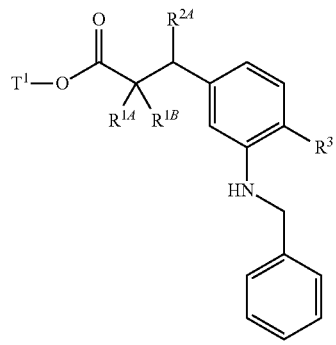

in which $R^{1A}$, $R^{1B}$, $R^{2A}$, $R^3$ and $T^1$ have the meanings given above,
and then removing the N-benzyl group by hydrogenolysis giving a 3-(3-aminophenyl)propionic acid ester of the formula (III-B)

(III-B)

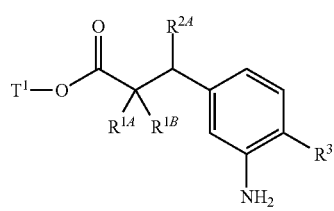

in which $R^{1A}$, $R^{1B}$, $R^{2A}$, $R^3$ and $T^1$ have the meanings given above, or

[D] reacting an acrylic acid ester of the formula (XXXV)

(XXXV)

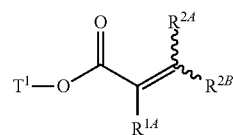

in which $R^{1A}$, $R^{2A}$, $R^{2B}$ and $T^1$ have the meanings given above
in an inert solvent either (i) with rhodium(I) catalysis with a phenylboronic acid of the formula (XXXVI)

(XXXVI)

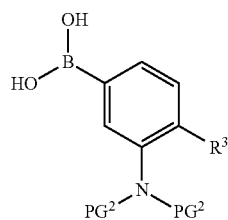

in which $R^3$ has the meaning given above
and
$PG^2$ represents benzyl or 4-methoxybenzyl as inert amino protective group,
or (ii) with copper(I) catalysis with a phenylmagnesium compound of the formula (XXXVII)

(XXXVII)

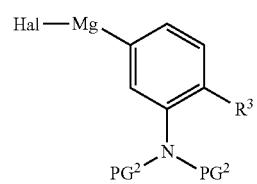

in which $PG^2$ and $R^3$ have the meanings given above
and
Hal represents chlorine or bromine,
to give a compound of the formula (XXXVIII)

(XXXVIII)

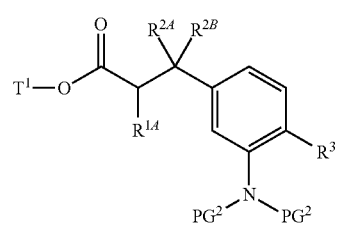

in which $PG^2$, $R^{1A}$, $R^{2A}$, $R^{2B}$, $R^3$ and $T^1$ have the meanings given above, and then removing the amino protective groups $PG^2$ by customary methods by hydrogenolysis or oxidatively affording a 3-(3-aminophenyl)propionic acid ester of the formula (III-C)

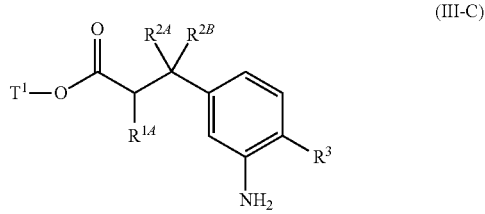

(III-C)

in which $R^{1A}$, $R^{2A}$, $R^{2B}$, $R^3$ and $T^1$ have the meanings given above.

Suitable for the deprotonation of the phosphono ester (XXII) in the olefination reactions (XXII)+(XXIII)→(XXIV) and (XXII)+(XXV)→(XXVI) [Horner-Wittig reaction] are in particular non-nucleophilic strong bases such as, for example, sodium hydride or potassium hydride, lithium bis (trimethylsilyl)amide, sodium bis(trimethylsilyl)amide or potassium bis(trimethylsilyl)amide or lithium diisopropylamide; preference is given to using sodium hydride. Preferred inert solvents employed in this reaction are ethers such as diethyl ether, diisopropyl ether, methyl tert-butyl ether, tetrahydrofuran, 1,2-dimethoxyethane or bis(2-methoxyethyl) ether, optionally as a mixture with N,N-dimethylformamide, dimethyl sulphoxide or hydrocarbons such as pentane, hexane or heptane. The reaction is generally carried out in a temperature range of from −20° C. to +40° C.

The hydrogenation in process steps (XXIV)→(III-A), (XXVI)→(III-A) and (XXX)→(III-A) is generally carried out under a stationary hydrogen atmosphere at standard pressure or elevated pressure. Here, preferred catalysts are palladium or platinum on activated carbon (as carrier material). The removal of the amino protective group(s) in the transformations (XXVII)→(III-A), (XXXIV)→(III-B) and (XXX-VIII)→(III-C) is usually carried out by hydrogenolysis according to the same procedure; in the case that $PG^2$ in (XXVII) or (XXXVIII) represents 4-methoxybenzyl, this may alternatively also be effected oxidatively, for example with the aid of 2,3-dichloro-5,6-dicyano-1,4-benzoquinone (DDQ) or ammonium cerium(IV) nitrate.

The palladium catalyst employed for the reaction (XX-VIII)+(XXIX)→(XXX) [Heck reaction] is preferably palladium(II) acetate or tris(dibenzylideneacetone)dipalladium (0), in each case in combination with a phosphine ligand such as, for example, tri-tert-butylphosphine, triphenylphosphine or tri-2-tolylphosphine.

Suitable for the α-deprotonation of the carboxylic acid ester (XXXI) in the alkylation reaction (XXXI)+(XXXII)→ (XXXIII) are in particular non-nucleophilic strong bases such as, for example, sodium tert-butoxide or potassium tert-butoxide, sodium hydride or potassium hydride, lithium diisopropylamide, lithium bis(trimethylsilyl)amide, sodium bis (trimethylsilyl)amide or potassium bis(trimethylsilyl)amide, or n-, sec- or tert-butyllithium; preference is given to using lithium diisopropylamide or n-butyllithium. Preferred inert solvents employed in this reaction are ethers such as diethyl ether, diisopropyl ether, methyl tert-butyl ether, tetrahydrofuran, 1,2-dimethoxyethane or bis(2-methoxyethyl) ether, optionally as a mixture with N,N-dimethylformamide or hydrocarbons such as pentane, hexane or heptane. The reaction is usually carried out in a temperature range of from −80° C. to +25° C.

For the transformation (XXXIII)→(XXXIV) [Buchwald-Hartwig coupling with benzylamine], preference is given to using tris(dibenzylideneacetone)dipalladium(0) as catalyst in combination with (±)-2,2'-bis(diphenylphosphino)-1,1'-binaphthyl as phosphine ligand and sodium or potassium tert-butoxide as base [cf., for example, J. P. Wolfe and S. L. Buchwald, Organic Syntheses, Coll. Vol. 10, 423 (2004), Vol. 78, 23 (2002)].

The coupling reactions (XXXV)+(XXXVI)→(XXXVIII) and (XXXV)+(XXXVII)→(XXXVIII) are carried out analogously to methods described in the literature [see, for example, N. Miyaura et al., Organometallics 16, 4229 (1997); T. Hayashi, Synlett, Special Issue 2001, 879-887; P. Knochel et al., Tetrahedron 56, 2727-2731 (2000), Angew. Chem. 120, 6907-6911 (2008)].

The reactions described above can be carried out at atmospheric, elevated or reduced pressure (for example in the range from 0.5 to 5 bar); in general, the reactions are each carried out at atmospheric pressure.

Separation of the compounds according to the invention into the corresponding enantiomers and/or diastereomers can, if expedient, also be carried out even at the stage of the compounds (II), (III), (IV), (V), (VII), (IX), (XI), (XIV), (XV), (XVI), (XXI), (XXVII), (XXXIII), (XXXIV) and/or (XXXVIII) which are then, in separated form, reacted further in accordance with the process sequences described above. Such a separation of stereoisomers can be carried out by customary methods known to the person skilled in the art. In the context of the present invention, preference is given to using chromatographic methods on achiral or chiral separation phases; in the case of carboxylic acids as intermediates or end products, separation may alternatively be effected via diastereomeric salts.

The compounds of the formulae (VI), (X), (XII), (XIII), (XVII), (XVIII), (XXII), (XXIII), (XXV), (XXVIII), (XXIX), (XXXI), (XXXII), (XXXV), (XXXVI) and (XXX-VII) are either commercially available or described as such in the literature, or they can be prepared by routes evident to the person skilled in the art analogously to methods published in the literature. Numerous detailed methods and literature information for preparation of the starting materials can also be found in the experimental part, in the section for preparation of the starting compounds and intermediates.

The preparation of the compounds according to the invention can be illustrated by way of example by the following reaction schemes:

Scheme 1

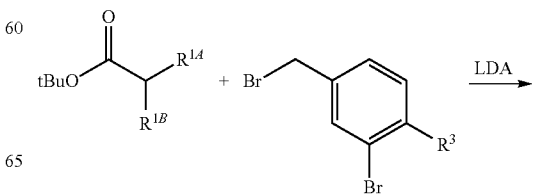

27
-continued
28
-continued
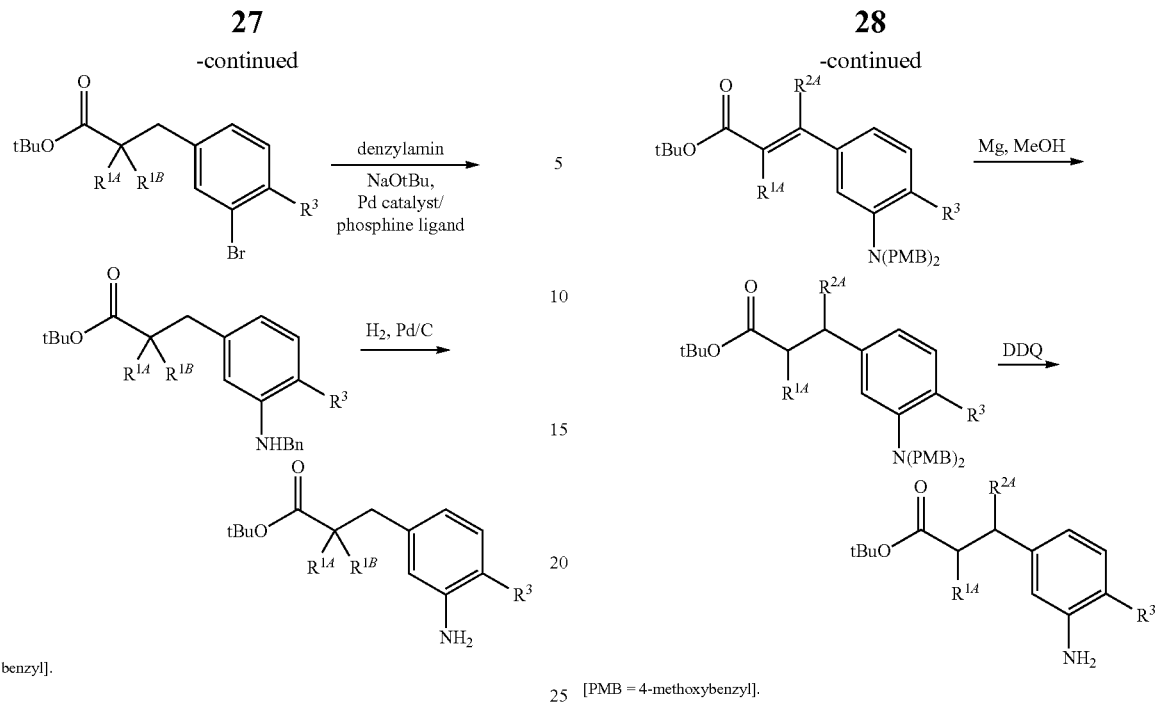
[Bn = benzyl].
[PMB = 4-methoxybenzyl].
Scheme 2a
Scheme 3
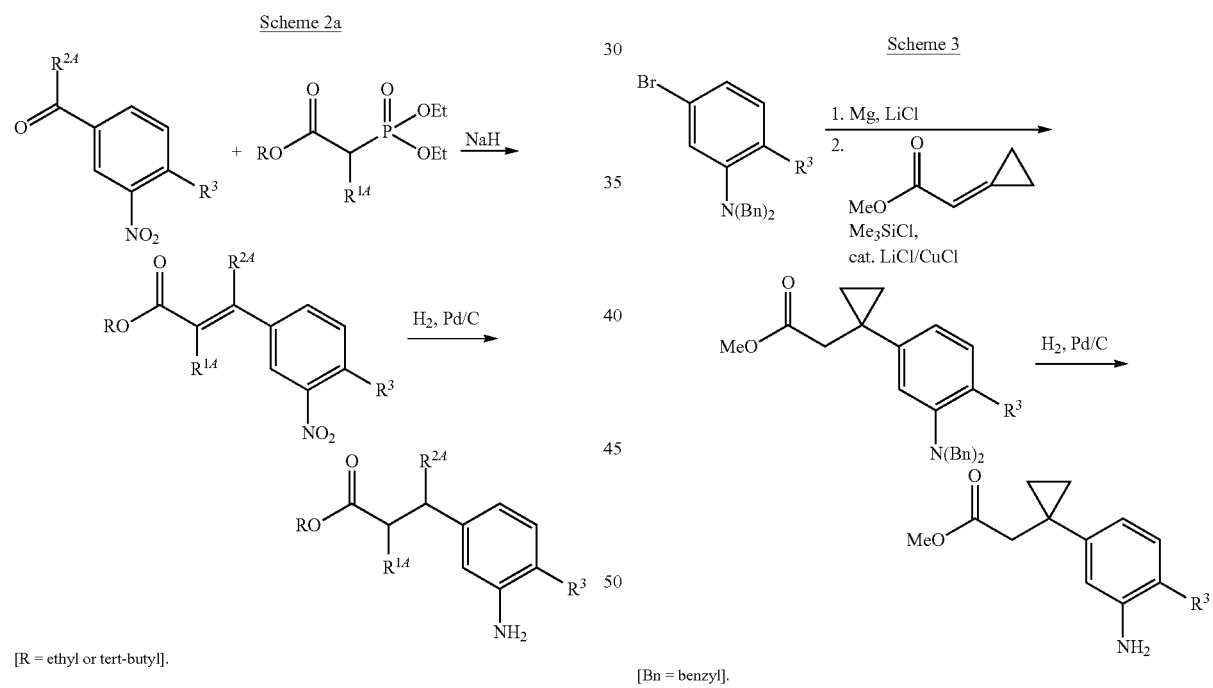
[R = ethyl or tert-butyl].
[Bn = benzyl].
Scheme 2b
Scheme 4
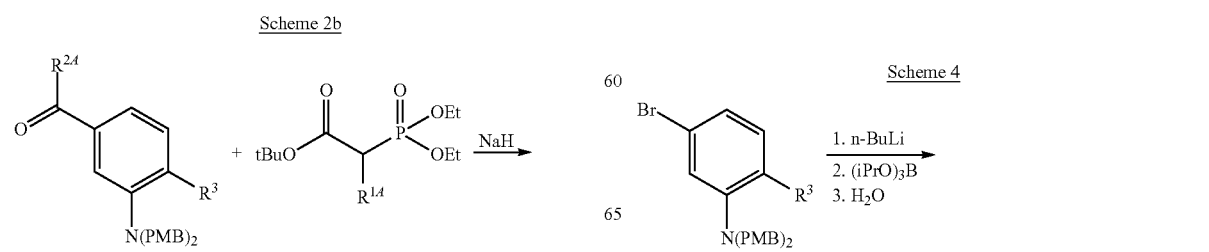

29
-continued
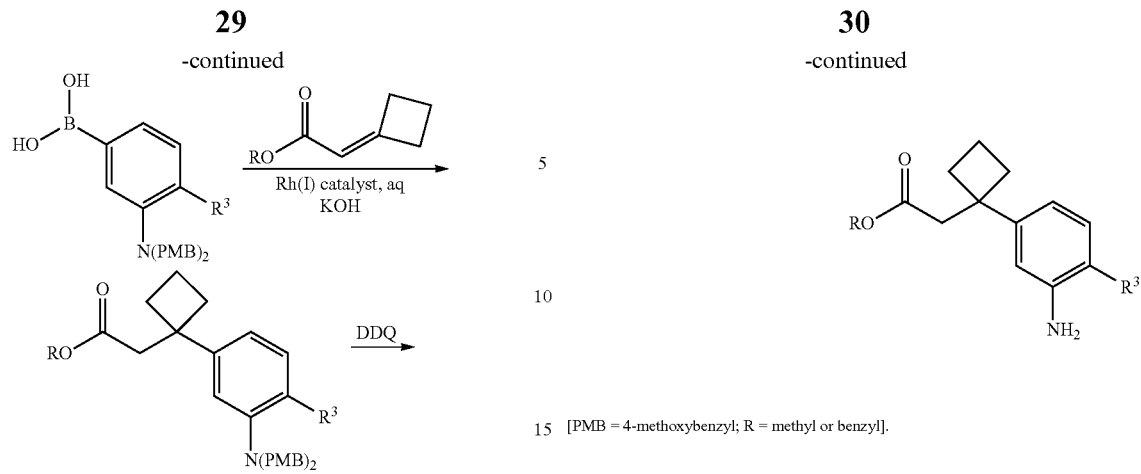
30
-continued
15 [PMB = 4-methoxybenzyl; R = methyl or benzyl].
Scheme 5
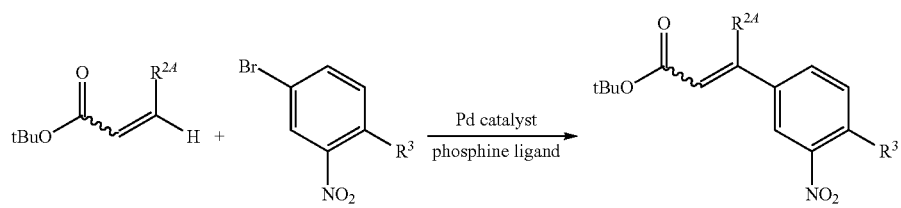
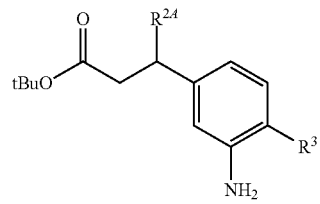
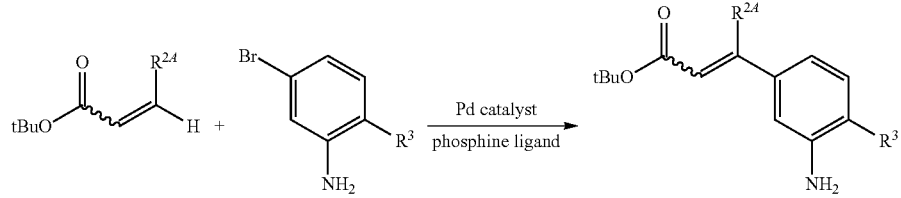

Scheme 6
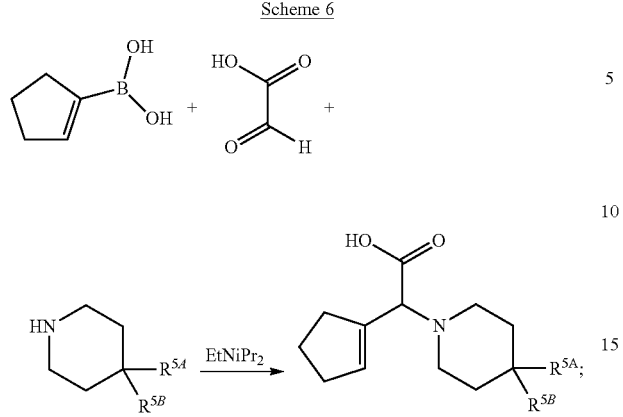
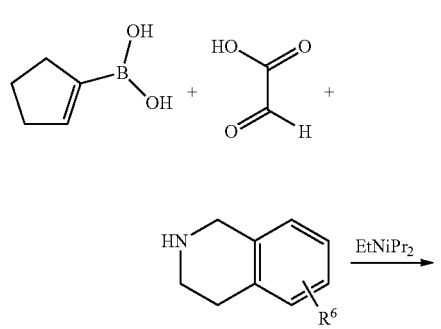
Scheme 7
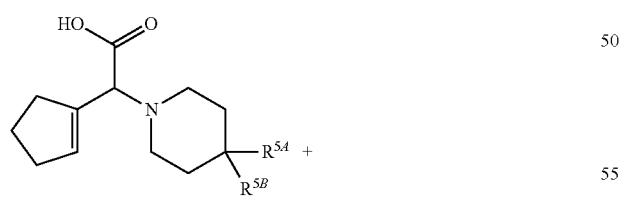
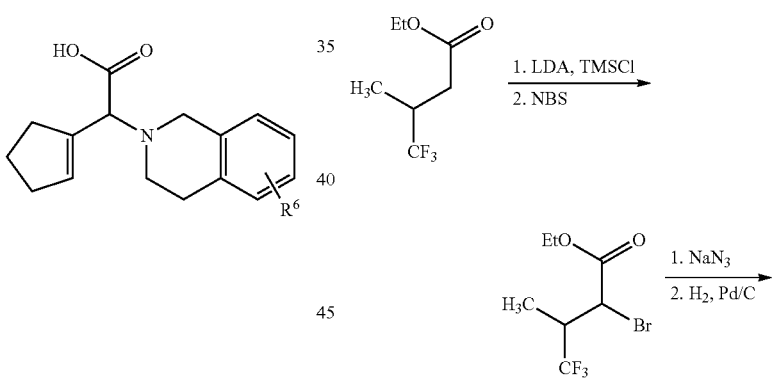
Scheme 8
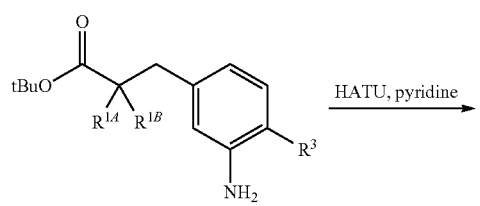
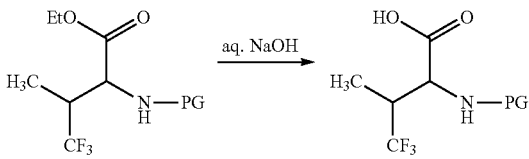
[PG = amino protective group, e.g. allyloxycarbonyl (Alloc) or benzyloxycarbonyl (Z)].

Scheme 9

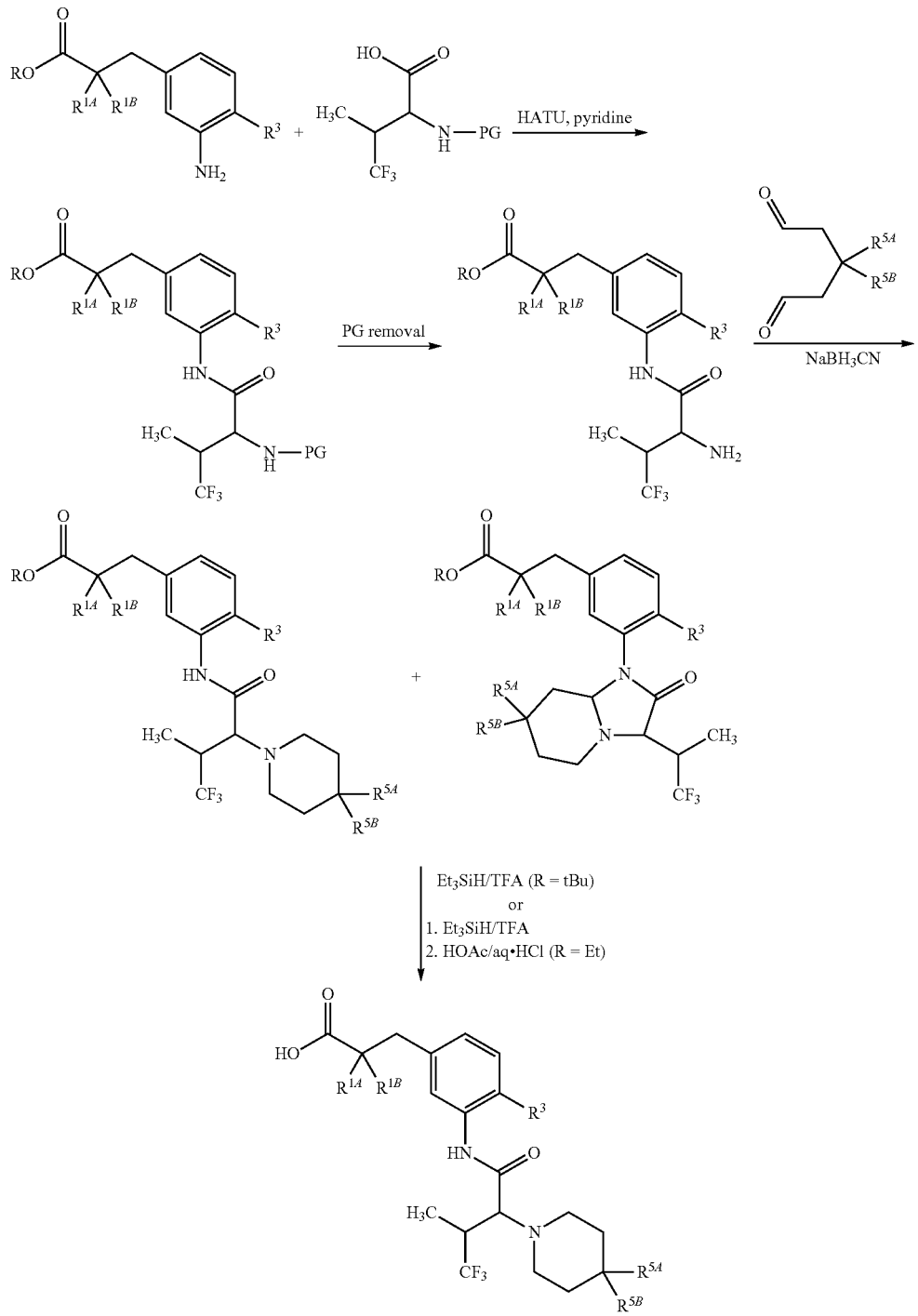

[PG = amino protective group, e.g. allyloxycarbonyl (Alloc) or benzyloxycarbonyl (Z); R = ethyl or tert-butyl].

The compounds according to the invention have valuable pharmacological properties and can be used for prevention and treatment of diseases in humans and animals.

The compounds according to the invention are potent activators of soluble guanylate cyclase. They lead to vascular relaxation, inhibition of platelet aggregation and lowering of blood pressure, and they also increase coronary blood flow. These effects are mediated by a direct, haem-independent activation of soluble guanylate cyclase and an intracellular rise in cGMP.

In addition, the compounds according to the invention have advantageous pharmacokinetic properties, in particular with regard to their bioavailability and/or duration of action following intravenous or oral administration.

The compounds according to the invention are especially suitable for treatment and/or prevention of cardiovascular, pulmonary, thromboembolic and fibrotic disorders.

Accordingly, the compounds according to the invention can be used in medicaments for the treatment and/or prevention of cardiovascular disorders such as, for example, high blood pressure (hypertension), heart failure, coronary heart disease, stable and unstable angina pectoris, pulmonary arterial hypertension (PAH) and other forms of pulmonary hypertension (PH), renal hypertension, peripheral and cardiac vascular disorders, arrhythmias, atrial and ventricular arrhythmias and impaired conduction such as, for example, atrioventricular blocks degrees I-III, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV junctional extrasystoles, sick sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

In addition, the compounds according to the invention can also be used for treatment and/or prevention of arteriosclerosis, impaired lipid metabolism, hypolipoproteinaemias, dyslipidaemias, hypertriglyceridaemias, hyperlipidaemias, combined hyperlipidaemias, hypercholesterolaemias, abetalipoproteinaemia, sitosterolaemia, xanthomatosis, Tangier disease, adiposity, obesity and metabolic syndrome.

The compounds according to the invention can additionally be used for treatment and/or prevention of primary and secondary Raynaud's phenomenon, microcirculation impairments, claudication, tinnitus, peripheral and autonomic neuropathies, diabetic microangiopathies, diabetic retinopathy, diabetic ulcers on the extremities, gangrene, CREST syndrome, erythematosis, onychomycosis and rheumatic disorders.

In addition, the compounds according to the invention can be employed for the prevention of ischaemia- and/or reperfusion-related damage to organs or tissues and as additive for perfusion and preservation solutions for organs, organ parts, tissues or tissue parts of human or animal origin, in particular for surgical interventions or in the field of transplantation medicine.

The compounds according to the invention are also suitable for the treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also comprises the use of the compounds according to the invention for the treatment and/or prevention of sequelae of renal insufficiency, for example hypertension, pulmonary oedema, heart failure, uraemia, anaemia, electrolyte disturbances (for example hyperkalaemia, hyponatraemia) and disturbances in bone and carbohydrate metabolism.

In addition, the compounds according to the invention are suitable for the treatment and/or prevention of disorders of the urogenital system such as, for example, benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence such as, for example, mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds according to the invention are also suitable for the treatment and/or prevention of asthmatic disorders, chronic-obstructive pulmonary diseases (COPD), acute respiratory distress syndrome (ARDS) and acute lung injury (ALI), alpha-1-antitrypsin deficiency (AATD), pulmonary fibrosis, pulmonary emphysema (for example cigarette smoke-induced pulmonary emphysema) and cystic fibrosis (CF) and also pulmonary arterial hypertension (PAH) and other forms of pulmonary hypertension (PH) including left-sided heart failure, HIV, sickle cell anaemia, thromboembolisms sarcoidosis, COPD or pulmonary fibrosis-associated pulmonary hypertension.

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for treatment and/or prevention of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraines. They are also suitable for the prophylaxis and control of sequelae of cerebral infarction (cerebral apoplexy) such as stroke, cerebral ischaemia and craniocerebral trauma. The compounds according to the invention can likewise be employed for controlling states of pain.

In addition, the compounds according to the invention have anti-inflammatory action and can therefore be used as anti-inflammatory agents for treatment and/or prevention of sepsis (SIRS), multiple organ failure (MODS, MOF), inflammatory disorders of the kidney, chronic intestinal inflammations (IBD, Crohn's disease, ulcerative colitis), pancreatitis, peritonitis, rheumatoid disorders, inflammatory skin disorders and inflammatory eye disorders.

Furthermore, the compounds according to the invention are suitable for treatment and/or prevention of fibrotic disorders of the internal organs, for example the lung, the heart, the kidney, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring, naevi, diabetic retinopathy, proliferative vitroretinopathy and disorders of the connective tissue (for example sarkoidosis). The compounds according to the invention can also be used for promoting wound healing, for controlling postoperative scarring, for example as a result of glaucoma operations and cosmetically for ageing or keratinized skin.

By virtue of their property profile, the compounds according to the invention are particularly suitable for the treatment and/or prevention of cardiovascular disorders such as heart failure, angina pectoris, hypertension and pulmonary hypertension, and also of thromboembolic disorders, ischaemias, vascular disorders, impaired microcirculation, renal insufficiency, fibrotic disorders and arteriosclerosis.

The present invention further provides for the use of the inventive compounds for treatment and/or prevention of disorders, especially the aforementioned disorders.

The present invention further provides for the use of the compounds according to the invention for producing a medicament for the treatment and/or prevention of disorders, in particular the disorders mentioned above.

The present invention furthermore provides for the use of the compounds according to the invention in a method for treatment and/or prevention of disorders, in particular the disorders mentioned above.

The present invention further provides a method for treatment and/or prevention of disorders, in particular the disorders mentioned above, using an effective amount of at least one of the compounds according to the invention.

The compounds according to the invention can be used alone or, if required, in combination with other active compounds. The present invention therefore further provides medicaments comprising at least one of the inventive compounds and one or more further active ingredients, especially for treatment and/or prevention of the aforementioned disorders. Preferred examples of active compounds suitable for combinations include:

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;

NO-independent but haem-dependent stimulators of guanylate cyclase, such as especially riociguat and the compounds described in WO 00/06568, WO 00/06569, WO 02/42301 and WO 03/095451;

antithrombotic agents, by way of example and with preference from the group of the platelet aggregation inhibitors, the anticoagulants or the profibrinolytic substances;

hypotensive active ingredients, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or active compounds which alter lipid metabolism, for example and with preference from the group of thyroid receptor agonists, cholesterol synthesis inhibitors, preferred examples being HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor, by way of example and with preference aspirin, clopidogrel, ticlopidin or dipyridamole.

In a preferred embodiment of the invention, the compounds according to the invention are administered in combination with a thrombin inhibitor, by way of example and with preference ximelagatran, melagatran, dabigatran, bivalirudin or clexane.

In a preferred embodiment of the invention, the compounds according to the invention are administered in combination with a GPIIb/IIIa antagonist such as, by way of example and with preference tirofiban or abciximab.

In a preferred embodiment of the invention, the compounds according to the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embusartan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a diuretic, by way of example and with preference furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds according to the invention are administered in combination with a CETP inhibitor, by way of example and with preference torcetrapib (CP-529 414), HT-705 or CETP vaccine (Avant).

In a preferred embodiment of the invention, the compounds according to the invention are administered in combination with a thyroid receptor agonist, by way of example and with preference D-thyroxin, 3,5,3'-triiodothyronin (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, by way of example and with preference orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, nontoxic, pharmaceutically suitable excipients, and the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in suitable administration forms for these administration routes.

Suitable administration forms for oral administration are those which work according to the prior art and release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral and intravenous administration.

The compounds according to the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of from about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary where appropriate to deviate from the stated amounts, specifically as a function of the body weight, route of administration, individual response to the active compound, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are in each case based on volume.

A. EXAMPLES

Abbreviations and Acronyms abs. absolute
Ac acetyl
Alloc allyloxycarbonyl
aq. aqueous, aqueous solution
ATP adenosine-5'-triphosphate
Bn benzyl
Boc tert-butoxycarbonyl
Brij® polyethylene glycol dodecyl ether
BSA bovine serum albumin
Ex. Example
Bu butyl
c concentration
cat. catalytic
CI chemical ionization (in MS)
d day(s)
TLC thin-layer chromatography
DCI direct chemical ionization (in MS)
DDQ 2,3-dichloro-5,6-dicyano-1,4-benzoquinone
de diastereomeric excess
DMF dimethylformamide
DMSO dimethyl sulphoxide
DTT dithiothreitol
ee enantiomeric excess
EI electron impact ionization (in MS)
ent enantiomerically pure, enantiomer
eq. equivalent(s)
ESI electrospray ionization (in MS)
Et ethyl
Fmoc 9-fluorenylmethoxycarbonyl
GC gas chromatography
sat. saturated
GTP guanosine-5'-triphosphate
h hour(s)
HATU O-(7-azabenzotriazol-1-yl)-N,N,N',N'-tetramethyluronium hexafluorophosphate
HOAc acetic acid
HOSu N-hydroxysuccinimide HPLC high-pressure high-performance liquid chromatography
iPr isopropyl
conc. concentrated
LC-MS liquid chromatography-coupled mass spectroscopy
LDA lithium diisopropylamide
Me methyl
min minute(s)
MS mass spectroscopy
NBS N-bromosuccinimide
NMR nuclear magnetic resonance spectroscopy
p para
Pd/C palladium on activated carbon
Ph phenyl
PMB p-methoxybenzyl(4-methoxybenzyl)
Pr propyl
rac racemic, racemate
$R_f$ retention index (in TLC)
RP reverse phase (in HPLC)
RT room temperature
$R_t$ retention time (in HPLC or GC)
tBu tert-butyl
TEA triethanolamine
TFA trifluoroacetic acid
THF tetrahydrofuran
TMS trimethylsilyl
UV ultraviolet spectroscopy
v/v ratio by volume (of a solution)
Z benzyloxycarbonyl
tog. together
GC-MS and LC-MS Methods:
Method 1 (GC-MS):
  Instrument: Micromass GCT, GC 6890; column: Restek RTX-35, 15 m×200 μm×0.33 μm; constant helium flow rate: 0.88 ml/min; oven: 70° C.; inlet: 250° C.; gradient: 70° C., 30° C./min 310° C. (maintained for 3 min)
Method 2 (LC-MS):
  Instrument: Waters Acquity SQD UPLC System; column: Waters Acquity UPLC HSS T3 1.8μ, 50 mm×1 mm; mobile phase A: 1 l of water+0.25 ml of 99% formic acid, eluent B: 1 l of acetonitrile+0.25 ml of 99% formic acid; gradient: 0.0 min 90% A→1.2 min 5% A→2.0 min 5% A; flow rate: 0.40 ml/min; oven: 50° C.; UV detection: 210-400 nm
Method 3 (LC-MS):
  Instrument: Micromass Quattro Premier with Waters UPLC Acquity; column: Thermo Hypersil GOLD 1.9μ, 50 mm×1 mm; mobile phase A: 1 l of water+0.5 ml of 50% strength formic acid, mobile phase B: 1 l of acetonitrile+0.5 ml of 50% formic acid; gradient: 0.0 min 90% A→0.1 min 90% A→1.5 min 10% A→2.2 min 10% A; flow rate: 0.33 ml/min; oven: 50° C.; UV detection: 210 nm
Method 4 (LC-MS):
  MS instrument type: Waters ZQ; HPLC instrument type: Agilent 1100 Series; UV DAD; column: Thermo Hypersil GOLD 3μ, 20 mm×4 mm; mobile phase A: 1 l of water+0.5 ml of 50% strength formic acid, mobile phase B: 1 l of acetonitrile+0.5 ml of 50% formic acid; gradient: 0.0 min 100% A→3.0 min 10% A→4.0 min 10% A→4.1 min 100% A (flow rate 2.5 ml/min); oven: 55° C.; flow rate: 2 ml/min; UV detection: 210 nm
Method 5 (LC-MS):
  MS instrument type: Waters (Micromass) Quattro Micro; HPLC instrument type: Agilent 1100 series; column: Thermo Hypersil GOLD 3μ, 20 mm×4 mm; mobile phase A: 1 l of water+0.5 ml of 50% strength formic acid, mobile phase B: 1 l of acetonitrile+0.5 ml of 50% formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Starting Materials and Intermediates:

Example 1A tert-Butyl 1-(3-bromo-4-fluorobenzyl)cyclopropanecarboxylate

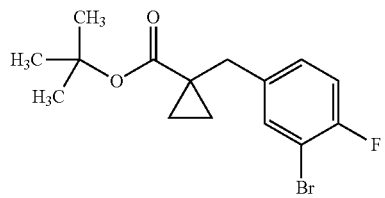 [SMILES: CC(C)(C)OC(=O)C1(Cc2ccc(F)c(Br)c2)CC1]

Under argon, 199.5 ml (1.42 mol) of diisopropylamine were initially charged in 1300 ml of dry THF and cooled to −50° C. 569.1 ml (1.42 mol) of n-butyllithium solution (2.5 M in hexane) were slowly added dropwise. The resulting mixture was warmed to 0° C. and then cooled to −70° C. A solution of 161.9 g (1.14 mol) of tert-butyl cyclopropanecarboxylate in 380 ml THF was added to the reaction solution, with the temperature being kept below −60° C. After 4 h of stirring at −78° C., a solution of 262 g (0.95 mol) of 2-bromo-4-(bromomethyl)-1-fluorobenzene in 480 ml of THF was added, the temperature again being kept below −60° C. The reaction mixture was then slowly warmed to RT overnight, after which 1.5 liters of saturated aqueous ammonium chloride solution and 3.0 liters of ethyl acetate were carefully added. After phase separation, the aqueous phase was extracted with ethyl acetate. The combined organic phases were washed with saturated sodium chloride solution, dried over magnesium sulphate and concentrated under reduced pressure. The crude product was purified by chromatography on 3 kg of silica gel (mobile phase cyclohexane/dichloromethane 9:1, then 5:1). 189.9 g (50.4% of theory) of the title compound were thus obtained.

$^1$H-NMR (400 MHz, DMSO-$d_6$): δ [ppm]=0.86-0.92 (m, 2H), 1.06-1.12 (m, 2H), 1.30 (s, 9H), 2.81 (s, 2H), 7.27-7.33 (m, 2H), 7.55-7.60 (m, 1H).

Example 2A tert-Butyl 1-[3-(benzylamino)-4-fluorobenzyl]cyclopropanecarboxylate

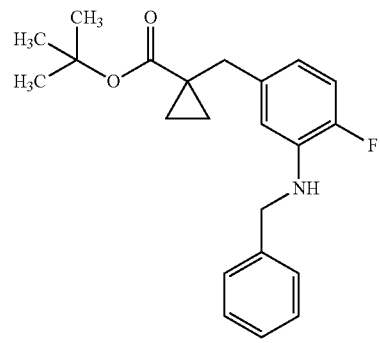 [SMILES: CC(C)(C)OC(=O)C1(Cc2ccc(F)c(NCc3ccccc3)c2)CC1]

Under argon and under dry conditions, 174.0 g (528.5 mmol) of tert-butyl 1-(3-bromo-4-fluorobenzyl)cyclopropanecarboxylate, 69.2 ml (634.2 mmol) of benzylamine, 4.84 g (5.29 mmol) of tris(dibenzylideneacetone)dipalladium, 60.95 g (634.2 mmol) of sodium tert-butoxide and 3.29 g (5.29 mmol) of (+/−)-2,2'-bis(diphenylphosphino)-1,1'-binaphthyl were suspended in 1218 ml of toluene. The reaction mixture was then stirred at 110° C. for 2.0 h. After cooling, 2.1 liters of ethyl acetate and 1.7 liters of semisaturated aqueous ammonium chloride solution were added to the reaction mixture. After phase separation, the organic phase was washed with a saturated ammonium chloride solution and saturated sodium chloride solution, dried over magnesium sulphate and concentrated under reduced pressure. The crude product was purified by chromatography on 3.7 kg of silica gel (mobile phase petroleum ether/ethyl acetate 20:1). 145.0 g (68.7% of theory) of the title compound were thus obtained.

$^1$H-NMR (400 MHz, DMSO-$d_6$): δ [ppm]=0.51-0.66 (m, 2H), 0.86-0.99 (m, 2H), 1.25 (m, 9H), 2.65 (s, 2H), 4.30 (d, 2H), 6.07 (t, 1H), 6.29-6.54 (m, 2H), 6.88 (dd, 1H), 7.15-7.25 (m, 1H), 7.25-7.42 (m, 4H).

Example 3A tert-Butyl 1-(3-amino-4-fluorobenzyl)cyclopropanecarboxylate

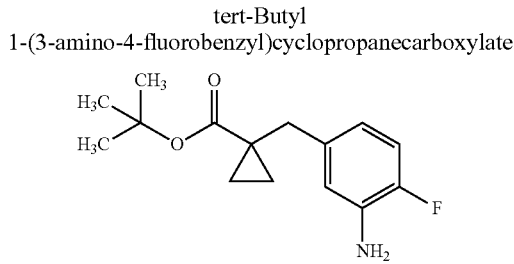

145.0 g (407.9 mmol) of tert-butyl 1-[3-(benzylamino)-4-fluorobenzyl]cyclopropanecarboxylate were dissolved in 1450 ml of ethanol, and 9.67 g of palladium hydroxide (20% on carbon) were added. The suspension was stirred at RT under a hydrogen atmosphere at standard pressure for 18 h. The reaction mixture was then filtered off with suction through kieselguhr, and the filtrate was concentrated. After drying under high vacuum, 500 ml of pentane were added to the residue, resulting in the precipitation of the product. The suspension was stirred in an ice bath for 1 h. The solid was then filtered off with suction, washed twice with pentane and dried under high vacuum. 88.5 g (73.6% of theory) of the title compound were thus obtained.

$^1$H-NMR (400 MHz, DMSO-$d_6$): δ [ppm]=0.70-0.80 (m, 2H), 1.00-1.10 (m, 2H), 1.30 (s, 9H), 2.68 (s, 2H), 4.98 (s, 2H), 6.28-6.45 (m, 1H), 6.63 (dd, 1H), 6.84 (dd, 1H).

Example 4A tert-Butyl (2E)-3-(4-fluoro-3-nitrophenyl)acrylate

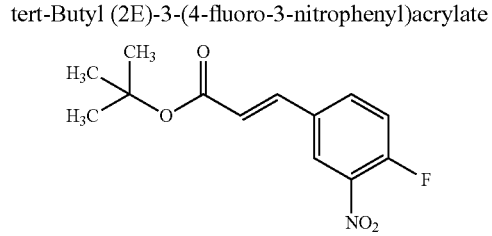

At RT and with slight cooling, 99.23 g (394 mmol) of tert-butyl diethylphosphonoacetate were added dropwise to a suspension of 15.74 g (394 mmol) of sodium hydride (60% in mineral oil) in 540 ml of THF. After the addition had ended, the mixture was stirred at RT for 30 min and, after cooling to 0° C., a solution of 60.5 g (358 mmol) of 4-fluoro-3-nitrobenzaldehyde in 324 ml of THF was added. The reaction mixture was stirred at RT overnight and then added to a 10% strength aqueous sodium chloride solution. The mixture was extracted twice with ethyl acetate. The combined organic phases were washed with sat. sodium chloride solution, dried over magnesium sulphate and concentrated under reduced pressure. The residue was purified by chromatography (twice) on silica gel (mobile phase petroleum ether/ethyl acetate 9:1). This gave 82.0 g (84.9% of theory) of the target product.

GC-MS (Method 1): $R_t$=6.47 min; m/z=211 (M-$C_4H_8$)$^+$.

$^1$H-NMR (400 MHz, DMSO-$d_6$): δ [ppm]=1.49 (s, 9H), 6.70 (d, 1H), 7.60-7.75 (m, 2H), 8.20 (ddd, 1H), 8.51 (dd, 1H).

Example 5A tert-Butyl 3-(3-amino-4-fluorophenyl)propanoate

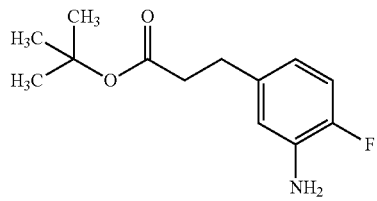 [SMILES: CC(C)(C)OC(=O)CCc1ccc(F)c(N)c1]

A solution of 81.0 g (303 mmol) of tert-butyl (2E)-3-(4-fluoro-3-nitrophenyl)acrylate in a mixture of 810 ml of THF and 810 ml of ethanol was inertized with argon, and 8.1 g of 10% palladium on carbon were added. The suspension was stirred at RT under a hydrogen atmosphere at standard pressure for 9 h. The reaction mixture was then filtered off with suction through kieselguhr, and the filtrate was concentrated. The crude product was purified by chromatography on silica gel (mobile phase petroleum ether/ethyl acetate 4:1). This gave 66.0 g (91% of theory) of the title compound.

$^1$H-NMR (400 MHz, DMSO-$d_6$): δ [ppm]=1.36 (s, 9H), 2.42 (t, 2H), 2.64 (t, 2H), 5.00 (s, 2H), 6.33 (ddd, 1H), 6.59 (dd, 1H), 6.84 (dd, 1H).

Example 6A tert-Butyl (2E)-3-(4-chloro-3-nitrophenyl)acrylate

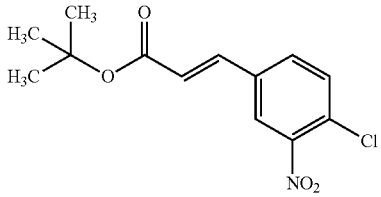 [SMILES: CC(C)(C)OC(=O)/C=C/c1ccc(Cl)c([N+](=O)[O-])c1]

At 0° C. and with cooling, 156.32 g (620 mmol) of tert-butyl diethylphosphonoacetate were added dropwise to a suspension of 23.71 g (593 mmol) of sodium hydride (60% in mineral oil) in 1.0 liters of THF. After the addition had ended, the mixture was stirred at 0° C. for 30 min and a solution of 100.0 g (539 mmol) of 4-chloro-3-nitrobenzaldehyde in 200 ml of THF was then added. The reaction mixture was heated at RT overnight, and water and ethyl acetate were then added. The organic phase was removed, dried with magnesium sulphate and concentrated under reduced pressure. The residue was recrystallized from isopropanol. Drying under high vacuum gave 144.0 g (94.2% of theory) of the target product.

LC-MS (Method 2): $R_t$=1.28 min; m/z=269 (M-14)$^+$.

Example 7A tert-Butyl 3-(3-amino-4-chlorophenyl)propanoate

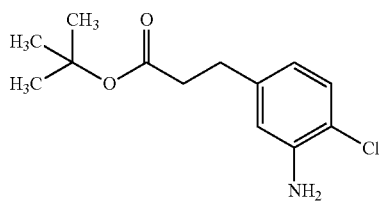 [SMILES: CC(C)(C)OC(=O)CCc1ccc(Cl)c(N)c1]

Under argon, 5.4 g of 10% palladium on carbon were added to a solution of 72.0 g (254 mmol) of tert-butyl (2E)-3-(4-chloro-3-nitrophenyl)acrylate in 1.0 liters of ethyl acetate. The suspension was stirred at RT under a hydrogen atmosphere at standard pressure for 7 h. The reaction mixture was then filtered off with suction through kieselguhr, and the filtrate was concentrated. The crude product was purified by chromatography on silica gel (mobile phase cyclohexane/ethyl acetate 9:1). This gave 38 g (58% of theory) of the title compound.

LC-MS (Method 2): $R_t$=1.14 min; m/z=256 (M+H)$^+$.

$^1$H-NMR (400 MHz, DMSO-d$_6$): δ [ppm]=1.36 (s, 9H), 2.43 (t, 2H), 2.65 (t, 2H), 5.21 (br. s, 2H), 6.39 (dd, 1H), 6.62 (d, 1H), 7.05 (d, 1H).

Example 8A

Ethyl (E/Z)-3-(4-fluoro-3-nitrophenyl)-2-methyl-prop-2-enoate

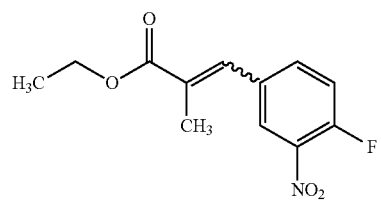

3.17 g of sodium hydride (60% suspension in mineral oil, 79.36 mmol) were suspended in 90 ml of a THF/DMF mixture (2:1). The mixture was cooled to 0° C., and a solution of 19.76 g (82.96 mmol) of triethyl 2-phosphonopropionate in 60 ml of THF/DMF (2:1) was added dropwise. After 30 min, a solution of 12.2 g (72.14 mmol) of 4-fluoro-3-nitrobenzaldehyde in 60 ml of THF/DMF (2:1) was added dropwise at 0° C. After the end of the addition, the reaction mixture was slowly warmed to RT and stirred at this temperature for 2 h. The reaction mixture was then added to water. The mixture was extracted three times with ethyl acetate, and the combined organic phases were concentrated under reduced pressure. The residue was purified by chromatography on silica gel (mobile phase cyclohexane/ethyl acetate 20:1). This gave 15.2 g (83.2% of theory) of the target product as an E/Z isomer mixture (E/Z 91:9).

LC-MS (Method 2): Z isomer: $R_t$=1.11 min; m/z=254 (M+H)$^+$; E isomer: $R_t$=1.14 min; m/z=254 (M+H)$^+$.

$^1$H-NMR (400 MHz, DMSO-d$_6$): E isomer: δ [ppm]=1.28 (t, 3H), 4.22 (q, 2H), 7.59-7.73 (m, 2H), 7.92 (ddd, 1H), 8.24 (dd, 1H).

Example 9A

Ethyl (+/−)-3-(3-amino-4-fluorophenyl)-2-methyl-propanoate

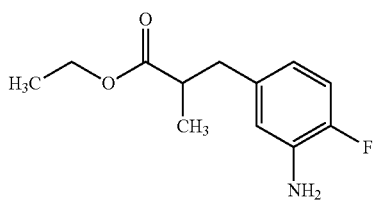 [SMILES: CCOC(=O)[C@@H](C)Cc1ccc(F)c(N)c1]

Palladium on carbon (10%) was added to 15.2 g (60.02 mmol) of ethyl (E/Z)-3-(4-fluoro-3-nitrophenyl)-2-methyl-prop-2-enoate (E/Z 91:9) in a mixture of 100 ml of ethanol and 100 ml of THF, and the mixture was stirred vigorously under an atmosphere of hydrogen at standard pressure overnight. The reaction mixture was then filtered through Celite, the residue was washed with ethanol/dichloromethane and the combined filtrates were concentrated under reduced pressure. The product was dried under high vacuum. This gave 13.34 g of the target product (98.7% of theory).

LC-MS (Method 2): $R_t$=0.98 min; m/z=226 (M+H)$^+$.

$^1$H-NMR (400 MHz, DMSO-d$_6$): δ [ppm]=1.04 (d, 3H), 1.12 (t, 3H), 2.46-2.50 (m, 1H), 2.55-2.66 (m, 1H), 2.66-2.78 (m, 1H), 4.01 (q, 2H), 5.00 (s, 2H), 6.18-6.35 (m, 1H), 6.55 (dd, 1H), 6.84 (dd, 1H).

The racemate obtained above was separated into the enantiomers by preparative HPLC on a chiral phase [column: Daicel Chiralpak AD-H, 5 μm, 250 mm×20 mm; injection volume: 0.15 ml; temperature: 30° C.; mobile phase: 90% isohexane/10% ethanol; flow rate: 15 ml/min; detection: 220 nm]. 7.25 g of racemate gave 3.43 g of enantiomer 1 (Example 10A) and 3.35 g of enantiomer 2 (Example 11A):

Example 10A

Ethyl (+)-(2S)-3-(3-amino-4-fluorophenyl)-2-methylpropanoate

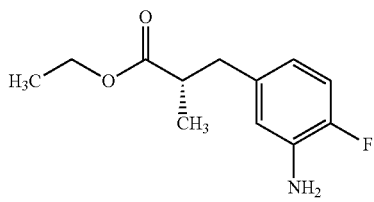

Yield: 3.43 g

LC-MS (Method 2): $R_t$=0.97 min; m/z=226 (M+H)$^+$.

$^1$H-NMR (400 MHz, DMSO-d$_6$): δ [ppm]=1.04 (d, 3H), 1.12 (t, 3H), 2.46-2.50 (m, 1H), 2.55-2.66 (m, 1H), 2.66-2.78 (m, 1H), 4.01 (q, 2H), 5.00 (s, 2H), 6.18-6.35 (m, 1H), 6.55 (dd, 1H), 6.84 (dd, 1H).

$[α]_D^{20}$=+18.3°, c=0.465, chloroform.

Example 11A

Ethyl (−)-(2R)-3-(3-amino-4-fluorophenyl)-2-methylpropanoate

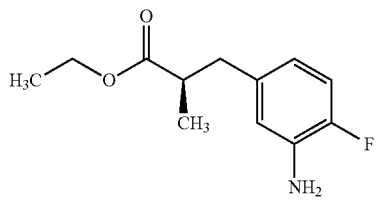 [SMILES: CCOC(=O)[C@H](C)Cc1ccc(F)c(N)c1]

Yield: 3.35 g

LC-MS (Method 2): $R_t$=0.97 min; m/z=226 (M+H)$^+$.

$^1$H-NMR (400 MHz, DMSO-d$_6$): δ [ppm]=1.04 (d, 3H), 1.12 (t, 3H), 2.46-2.50 (m, 1H), 2.55-2.66 (m, 1H), 2.68-2.79 (m, 1H), 4.01 (q, 2H), 5.00 (br. s, 2H), 6.30 (dd, 1H), 6.55 (dd, 1H), 6.84 (dd, 1H).

$[α]_D^{20}$=−31.4°, c=0.520, chloroform.

Example 12A

Ethyl (E/Z)-3-(4-chloro-3-nitrophenyl)-2-methylprop-2-enoate

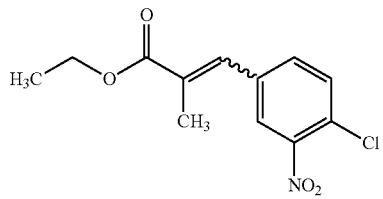 [SMILES: CCOC(=O)C(C)=Cc1ccc(Cl)c([N+](=O)[O-])c1]

4.74 g of sodium hydride (60% suspension in mineral oil, 118.56 mmol) were suspended in 93 ml of a THF/DMF mixture (1:1). The mixture was cooled to 0° C., and 26.6 ml (123.95 mmol) of triethyl 2-phosphonopropionate were added dropwise. After 30 min, 20.0 g (107.78 mmol) of 4-chloro-3-nitrobenzaldehyde were added at 0° C. After the end of the addition, the reaction mixture was slowly warmed to RT and stirred at this temperature for another 3 h. The reaction mixture was then added to water. The mixture was extracted three times with ethyl acetate, and the combined organic phases were concentrated under reduced pressure. The residue was purified by chromatography on silica gel (mobile phase cyclohexane/ethyl acetate 70:1→50:1). This gave 26.7 g (91.9% of theory) of the target product as an E/Z isomer mixture (E/Z 91:9).

LC-MS (Method 3): Z isomer: $R_t$=1.32 min; m/z=255; E isomer: $R_t$=1.36 min; m/z=270 (M+H)$^+$.

$^1$H-NMR (400 MHz, DMSO-d$_6$): E isomer: δ [ppm]=1.28 (t, 3H), 2.06 (d, 3H), 4.22 (q, 2H), 7.56-7.67 (m, 1H), 7.75-7.87 (m, 2H), 8.17 (d, 1H).

Example 13A

Ethyl (+/−)-3-(3-amino-4-chlorophenyl)-2-methylpropanoate

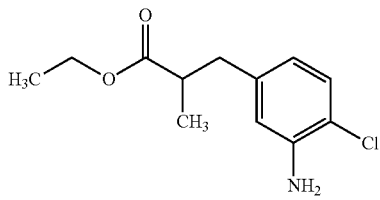 [SMILES: CCOC(=O)C(C)Cc1ccc(Cl)c(N)c1]

10.0 g (37.08 mmol) of ethyl (E/Z)-3-(4-chloro-3-nitrophenyl)-2-methylprop-2-enoate (E/Z 91:9) were dissolved in 25 ml of ethyl acetate and 25 ml of acetic acid, and palladium on carbon (10%) was added. The reaction mixture was stirred vigorously for a total of 6 h under an atmosphere of hydrogen at standard pressure, with another 25 ml of acetic acid and further portions of 10% palladium on carbon being added after 2 h. The mixture was then filtered through Celite and the residue was washed with ethanol/dichloromethane. The combined filtrates were washed with saturated sodium bicarbonate solution, dried over sodium sulphate and concentrated under reduced pressure. The crude product was purified by chromatography on silica gel (mobile phase cyclohexane/ethyl acetate 30:1→10:1). This gave 4.01 g of the target product (44.7% of theory).

LC-MS (Method 2): $R_t$=1.06 min; m/z=242 (M+H)$^+$.

$^1$H-NMR (400 MHz, DMSO-d$_6$): δ [ppm]=1.05 (d, 3H), 1.12 (t, 3H), 2.47-2.50 (m, 1H), 2.56-2.67 (m, 1H), 2.67-2.78 (m, 1H), 4.02 (q, 2H), 5.23 (s, 2H), 6.35 (dd, 1H), 6.58 (d, 1H), 7.05 (d, 1H).

The racemate obtained above was separated into the enantiomers by preparative HPLC on a chiral phase [column: Daicel Chiralpak OJ-H, 5 μm, 250 mm×20 mm; injection volume: 0.15 ml; temperature: 35° C.; mobile phase: 50% isohexane/50% isopropanol; flow rate: 15 ml/min; detection: 220 nm]. 10.3 g of racemate gave 4.0 g of enantiomer 1 (Example 14A) and 3.7 g of enantiomer 2 (Example 15A):

Example 14A

Ethyl (−)-(2R)-3-(3-amino-4-chlorophenyl)-2-methylpropanoate

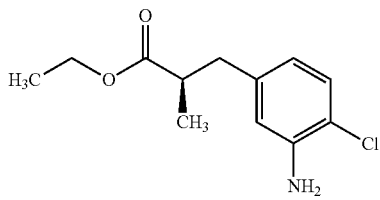 [SMILES: CCOC(=O)[C@H](C)Cc1ccc(Cl)c(N)c1]

Yield: 4.0 g

LC-MS (Method 4): $R_t$=2.27 min; m/z=196/198.

$^1$H-NMR (400 MHz, DMSO-$d_6$): δ [ppm]=1.05 (d, 3H), 1.12 (t, 3H), 2.47-2.50 (m, 1H), 2.54-2.66 (m, 2H), 2.68-2.80 (m, 1H), 4.02 (q, 2H), 5.23 (s, 2H), 6.35 (dd, 1H), 6.58 (d, 1H), 7.05 (d, 1H).

$[α]_D^{20}$=35.8°, c=0.560, chloroform.

Example 15A

Ethyl (+)-(2S)-3-(3-amino-4-chlorophenyl)-2-methylpropanoate

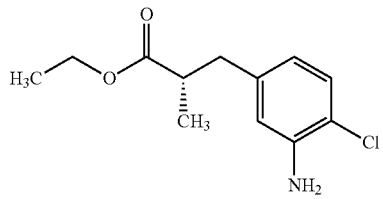 [SMILES: CCOC(=O)[C@@H](C)Cc1ccc(Cl)c(N)c1]

Yield: 3.7 g $^1$H-NMR (400 MHz, DMSO-$d_6$): δ [ppm]=1.05 (d, 3H), 1.12 (t, 3H), 2.47-2.50 (m, 1H), 2.56-2.67 (m, 1H), 2.67-2.81 (m, 1H), 4.02 (q, 2H), 5.23 (br. s, 2H), 6.35 (dd, 1H), 6.58 (d, 1H), 7.05 (d, 1H).

$[α]_D^{20}$=+35.1°, c=0.525, chloroform.

Example 16A tert-Butyl (2E/Z)-3-(4-chloro-3-nitrophenyl)but-2-enoate

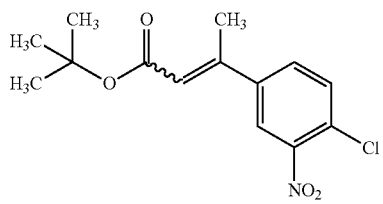 [SMILES: CC(=CC(=O)OC(C)(C)C)c1ccc(Cl)c([N+](=O)[O-])c1]

2.87 g of sodium hydride (60% suspension in mineral oil, 71.65 mmol) were suspended in 80 ml of THF. The mixture was cooled to 0° C., and 17.6 ml (74.9 mmol) of tert-butyl (diethoxyphosphoryl)acetate were added dropwise. After 30 min, 13.0 g (65.1 mmol) of 4-chloro-3-nitroacetophenone were added at 0° C. After the end of the addition, the reaction mixture was slowly warmed to RT and stirred at RT for another 1.5 h, and the mixture was then added to water. The mixture was extracted three times with ethyl acetate, and the combined organic phases were concentrated under reduced pressure. The residue was purified by chromatography on silica gel (mobile phase cyclohexane/ethyl acetate 20:1→10: 1). This gave 17.03 g (87.8% of theory) of the target product as an E/Z isomer mixture (E/Z about 1:1).

LC-MS (Method 5): Isomer 1: $R_t$=2.61 min; m/z=255; isomer 2: $R_t$=2.77 min; m/z=224.

Example 17A tert.-Butyl (+/−)-3-(3-amino-4-chlorophenyl)butanoate

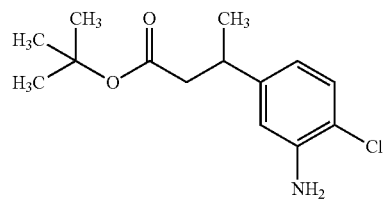 [SMILES: CC(CC(=O)OC(C)(C)C)c1ccc(Cl)c(N)c1]

11.5 g (38.62 mmol) of tert-butyl (2E/Z)-3-(4-chloro-3-nitrophenyl)but-2-enoate (E/Z about 1:1) were dissolved in 60 ml of ethyl acetate and 60 ml of acetic acid, and palladium on carbon (10%) was added. The reaction mixture was stirred vigorously at standard pressure under an atmosphere of hydrogen for 6 h. The mixture was filtered through Celite and the residue was washed with ethyl acetate. The combined filtrates were washed with saturated sodium bicarbonate solution, dried over sodium sulphate and concentrated under reduced pressure. The crude product was purified by chromatography on silica gel (mobile phase cyclohexane/ethyl acetate 30:1). This gave 3.90 g (37.4% of theory) of the target product.

$^1$H-NMR (400 MHz, DMSO-$d_6$): δ [ppm]=1.14 (d, 3H), 1.31 (s, 9H), 2.38 (dd, 2H), 2.95 (q, 1H), 5.21 (br. s, 2H), 6.42 (dd, 1H), 6.65 (d, 1H), 7.06 (d, 1H).

The racemate obtained above was separated into the enantiomers by preparative HPLC on a chiral phase [column: Daicel Chiralpak AD-H, 5 μm, 250 mm×20 mm; injection volume: 0.15 ml; temperature: 30° C.; mobile phase: 90% isohexane/10% ethanol; flow rate: 15 ml/min; detection: 220 nm]. 5.0 g of racemate gave 2.1 g of enantiomer 1 (Example 18A) and 1.8 g of enantiomer 2 (Example 19A):

Example 18A (+)-tert-Butyl (3R)-3-(3-amino-4-chlorophenyl)butanoate

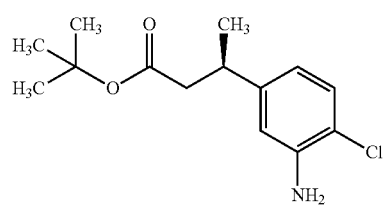 [SMILES: C[C@H](CC(=O)OC(C)(C)C)c1ccc(Cl)c(N)c1]

LC-MS (Method 3): $R_t$=1.34 min; m/z=270 (M+H)$^+$.

$^1$H-NMR (400 MHz, DMSO-d$_6$): δ [ppm]=1.14 (d, 3H), 1.31 (s, 9H), 2.19-2.45 (m, 2H), 2.95 (q, 1H), 5.20 (s, 2H), 6.42 (dd, 1H), 6.65 (d, 1H), 7.06 (d, 1H).

Example 19A (−)-tert-Butyl (3S)-3-(3-amino-4-chlorophenyl)butanoate

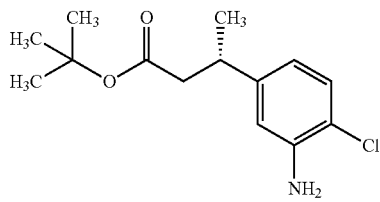

LC-MS (Method 3): $R_t$=1.34 min; m/z=214 (M+H-C$_4$H$_8$)$^+$.

$^1$H-NMR (400 MHz, DMSO-d$_6$): δ [ppm]=1.14 (d, 3H), 1.31 (s, 9H), 2.38 (dd, 2H), 2.95 (q, 1H), 5.20 (br. s, 2H), 6.42 (dd, 1H), 6.65 (d, 1H), 7.06 (d, 1H).

[α]$_D^{20}$=−24.1°, c=0.570, chloroform.

Example 20A

2-Bromo-4-(bromomethyl)-1-chlorobenzene

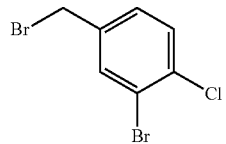

Step 1:

199.0 g (0.845 mol) of 3-bromo-4-chlorobenzoic acid were dissolved in 2.5 liters of THF, the solution was cooled to −10° C. and 1.69 liters (1.69 mol) of a 1 M solution of borane in THF were added at this temperature. The reaction mixture was warmed to RT overnight, and saturated aqueous ammonium chloride solution was then added. After addition of water, the mixture was extracted twice with ethyl acetate, and the combined organic phases were dried over magnesium sulphate and concentrated under reduced pressure. This gave, as a crude product, 206 g of (3-bromo-4-chlorophenyl)methanol which were used without further purification for the next step.

Step 2:

260 g (about 1.05 mol) of crude (3-bromo-4-chlorophenyl)methanol were dissolved in 2.86 liters of dichloromethane, the solution was cooled to −5° C. and 127.1 g (44.6 ml, 460 mmol) of phosphorus tribromide were added slowly. After the end of the addition, the mixture was stirred at −5° C. for another 1 h and then diluted with diluted with dichloromethane and water. The organic phase was removed, dried over magnesium sulphate and concentrated under reduced pressure. This gave, as a crude product, 280.5 g (about 84% of theory) of 2-bromo-4-(bromomethyl)-1-chlorobenzene.

GC-MS (Method 1): $R_t$=5.36 min; m/z=281/283/285 (M+H)$^+$.

$^1$H-NMR (400 MHz, DMSO-d$_6$): δ [ppm]=4.71 (s, 2H), 7.49 (dd, 1H), 7.63 (d, 1H), 7.89 (d, 1H).

Example 21A tert-Butyl 1-(3-bromo-4-chlorobenzyl)cyclopropanecarboxylate

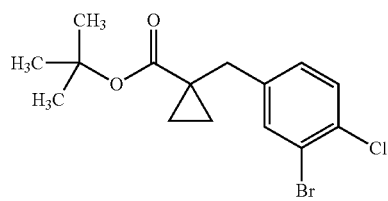 [SMILES: CC(C)(C)OC(=O)C1(Cc2ccc(Cl)c(Br)c2)CC1]

Under argon, 140.2 ml (1.0 mol) of diisopropylamine were dissolved in 1200 ml of dry THF and cooled to −30° C. 400 ml (1.0 mol) of n-butyllithium solution (2.5 M in hexane) were added dropwise. The resulting mixture was warmed to 0° C. and then cooled to −70° C. A solution of 94.8 g (0.667 mol) of tert-butyl cyclopropanecarboxylate in 750 ml THF was added to the reaction solution, with the temperature being kept below −60° C. After 4 h of stirring at −60° C., a solution of 208.6 g (0.733 mol) of 2-bromo-4-(bromomethyl)-1-chlorobenzene in 550 ml of THF was added, the temperature again being kept below −60° C. The reaction mixture was slowly warmed to RT overnight, and saturated aqueous ammonium chloride solution was then added carefully. After phase separation, the aqueous phase was extracted with ethyl acetate. The combined organic phases were dried over magnesium sulphate and concentrated under reduced pressure. The crude product was purified by chromatography on silica gel (mobile phase cyclohexane/dichloromethane 4:1). This gave 95.5 g (41.4% of theory) of the title compound.

GC-MS (Method 1): $R_t$=6.54 min; m/z=288/290 (M-C$_4$H$_8$)$^+$.

LC-MS (Method 3): $R_t$=1.65 min; m/z=288/290 (M-C$_4$H$_8$)$^+$.

Example 22A tert-Butyl 1-[3-(benzylamino)-4-chlorobenzyl]cyclopropanecarboxylate

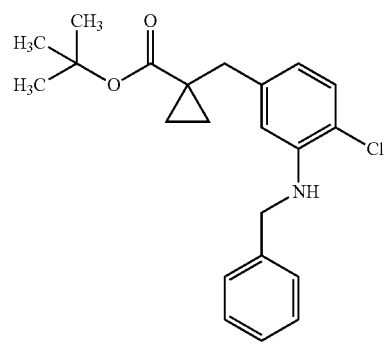 [SMILES: CC(C)(C)OC(=O)C1(Cc2ccc(Cl)c(NCc3ccccc3)c2)CC1]

Under argon, 95.0 g (274.8 mmol) of tert-butyl 1-(3-bromo-4-chlorobenzyl)cyclopropanecarboxylate, 36.0 ml (330.0 mmol) of benzylamine, 12.58 g (13.7 mmol) of tris (dibenzylideneacetone)dipalladium, 31.69 g (329.8 mmol) of sodium tert-butoxide and 6.85 g (5.29 mmol) of (+/−)-2,2′-bis(diphenylphosphino)-1,1′-binaphthyl were added successively to 633 ml of dry toluene. The reaction mixture was stirred at 110° C. for 3.0 h and then at RT overnight. The reaction mixture was then filtered off with suction through kieselguhr and the residue was washed thoroughly with toluene and ethyl acetate. The combined filtrates were concentrated under reduced pressure. The crude product was purified by chromatography on silica gel (mobile phase petroleum ether/ethyl acetate 10:1). This gave 50.0 g of the title compound (48.9% of theory).

LC-MS (Method 2): $R_t$=1.48 min; m/z=372 (M+H)$^+$.

Example 23A tert-Butyl 1-(3-amino-4-chlorobenzyl)cyclopropanecarboxylate

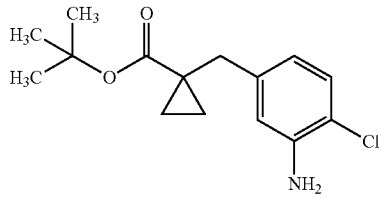 [SMILES: CC(C)(C)OC(=O)C1(Cc2ccc(Cl)c(N)c2)CC1]

50.0 g (134.4 mmol) of tert-butyl 1-[3-(benzylamino)-4-chlorobenzyl]cyclopropanecarboxylate were dissolved in 1.5 liters of ethyl acetate, and 1.43 g (1.34 mmol) of palladium (10% on carbon) were added. The reaction mixture was stirred at RT under a hydrogen atmosphere at standard pressure overnight. The reaction mixture was then filtered off with suction through kieselguhr, and the filtrate was concentrated. The crude product was purified by chromatography on silica gel (mobile phase petroleum ether/ethyl acetate 10:1). The resulting product was stirred in a methanol/water mixture (70:30) and the solid was isolated. 24.3 g (64.1% of theory) of the target compound were obtained.

LC-MS (Method 2): $R_t$=1.22 min; m/z=282 (M+H)$^+$.

$^1$H-NMR (400 MHz, DMSO-d$_6$): δ [ppm]=0.74-0.82 (m, 2H), 1.02-1.09 (m, 2H), 1.30 (s, 9H), 2.69 (s, 2H), 5.21 (br. s, 2H), 6.42 (dd, 1H), 6.67 (d, 1H), 7.05 (d, 1H).

Example 24A

N-[(Benzyloxy)carbonyl]-4,4,4-trifluorovaline (racemic diastereomer mixture)

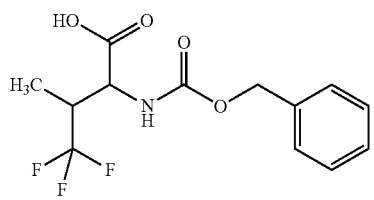 [SMILES: CC(C(NC(=O)OCc1ccccc1)C(=O)O)C(F)(F)F]

A little at a time, 15.0 g (72 mmol) of D,L-4,4,4-trifluorovaline hydrochloride were introduced into 160 ml of saturated aqueous sodium bicarbonate solution. At RT, a solution of 19.8 g (79 mmol) of N-(benzyloxycarbonyloxy)succinimide in 150 ml of dioxane was added to the mixture. The resulting reaction mixture was stirred vigorously for 2 h. Most of the dioxane was then removed under reduced pressure. The mixture was acidified to a pH of about 2 using 1 N hydrochloric acid and then extracted three times with dichloromethane, and the combined organic phases were dried over magnesium sulphate and concentrated under reduced pressure. The crude product was dried under high vacuum and used without further purification for subsequent reactions. This gave 26.0 g of the target product (purity about 80%, about 95% of theory).

LC-MS (Method 5): $R_t$=1.96 min; m/z=306 (M+H)$^+$.

$^1$H-NMR (400 MHz, DMSO-d$_6$): both diastereomers δ [ppm]=1.09/1.12 ((in each case d, tog. 3H), 2.82-3.05 (m, 1H), 4.30/4.59 (in each case dd, tog. 1H), 5.06/5.07 (in each case s, tog. 2H), 7.31-7.39 (m, 5H), 7.77/7.83 (in each case d, tog. 1H).

Example 25A

N-[(Allyloxy)carbonyl]-4,4,4-trifluorovaline (racemic diastereomer mixture)

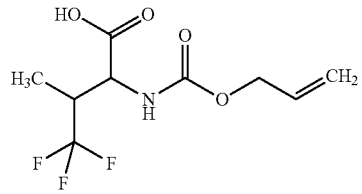 [SMILES: C=CCOC(=O)NC(C(=O)O)C(C)C(F)(F)F]

6.63 g (57.8 mmol) of succinimide were initially charged in 100 ml of THF, and 10.1 ml (72.6 mmol) of triethylamine were added at RT. After cooling to 0° C., a solution of 6.98 g (57.8 mmol) of allyl chloroformate in 10 ml of THF was added dropwise to the mixture. The mixture was stirred at 0° C. for 1 h, and 10.1 ml (72.6 mmol) of triethylamine and 10.0 g (48.2 mmol) of D,L-4,4,4-trifluorovaline hydrochloride were then added. After the addition had ended, the reaction mixture was, with vigorous stirring, slowly warmed to RT, and water was added after 2 h. The aqueous phase was acidified with 1 N hydrochloric acid to a pH of about 2 and then extracted three times with ethyl acetate The combined organic phases were dried over magnesium sulphate and concentrated under reduced pressure. The crude product was purified by chromatography on silica gel (mobile phase cyclohexane/ethyl acetate 4:1+1% acetic acid). This gave 9.15 g of the target product (74.4% of theory).

$^1$H-NMR (400 MHz, DMSO-d$_6$): both diastereomers δ [ppm]=1.09/1.12 ((in each case d, tog. 3H), 2.83-3.06 (m, 1H), 4.28/4.57 ((in each case dd, tog. 1H), 4.45-4.53 (m, 2H), 5.14-5.23 (m, 1H), 5.25-5.34 (m, 1H), 5.79-5.96 (m, 1H), 7.70/7.77 (in each case d, tog. 1H), 13.16 (br. s, 1H).

Example 26A

Ethyl (3R)-4,4,4-trifluoro-3-methylbutanoate

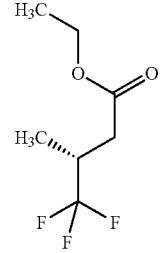

At room temperature, 133 ml (1.82 mol) of thionyl chloride were added slowly to 287 g (1.65 mol) of (3R)-4,4,4-trifluoro-3-methylbutanoic acid [A. Gerlach and U. Schulz, *Speciality Chemicals Magazine* 24 (4), 37-38 (2004); CAS Acc.-Nr. 142:179196] in 580 ml of ethanol. The reaction mixture was then heated to 80° C. and stirred at this temperature for 2 h. The mixture was then cooled to room temperature, 250 ml of water were added slowly and the mixture was extracted three times with 150 ml of tert-butyl methyl ether each time. The combined organic phases were dried over sodium sulphate. After filtration, the solvent was removed under reduced pressure at 30° C. and a pressure of 300 mbar. The crude product was then distilled at 100 mbar and a head temperature of 65° C. This gave 225.8 g (113 mol, 74% of theory) of the title compound as a colourless liquid.

$^1$H-NMR (400 MHz, DMSO-$d_6$): δ [ppm]=4.10 (2H, q), 2.88-2.72 (1H, m), 2.66-2.57 (1H, m), 2.46-2.36 (1H, m), 1.19 (3H, t), 1.11 (3H, d).

GC-MS (Method 1): $R_t$=1.19 min; m/z=184 (M)$^+$.

$[α]_D^{20}$=+16.1°, c=0.41, methanol.

Example 27A

Ethyl (3R)-4,4,4-trifluorovalinate (diastereomer mixture)

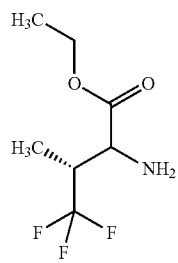

Step 1: Ethyl (3S)-2-bromo-4,4,4-trifluoro-3-methylbutanoate (diastereomer mixture)

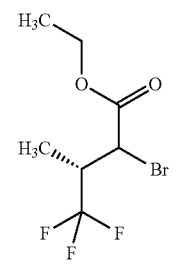

91.2 ml (228 mmol) of a 2.5 M solution of n-butyllithium solution in hexane were added to a solution, cooled to −40° C., of 32.0 ml (228 mmol) of diisopropylamine in 160 ml of abs. THF. The resulting LDA solution was stirred at −40° C. for 30 min and then cooled to −78° C., and 52.4 ml (413 mmol) of chlorotrimethylsilane were subsequently added dropwise. After 5 min, 40.0 g (217.2 mmol) of (+)-ethyl (3R)-4,4,4-trifluoro-3-methylbutanoate, dissolved in 40 ml of abs. THF, were added dropwise over a period of 1 h. At −78° C., in three portions a total of 40.59 g (228 mmol) of N-bromosuccinimide were added to the resulting suspension, and the mixture was then slowly warmed to RT overnight. Water was added carefully, and the reaction mixture was extracted with ethyl acetate. The organic phase was washed successively with 1 N hydrochloric acid, sat. sodium bicarbonate solution and sat. sodium chloride solution, dried over sodium sulphate and concentrated under reduced pressure without heating. 130 ml of diethyl ether were added to the resulting suspension, and the mixture was kept at 4° C. overnight. The undissolved solid formed was then filtered off and discarded. The filtrate was concentrated under reduced pressure without heating and the residue was briefly dried under high vacuum. This gave 48.5 g of ethyl (3S)-2-bromo-4,4,4-trifluoro-3-methylbutanoate (diastereomer mixture) as a crude product.

$^1$H-NMR (400 MHz, DMSO-$d_6$): both diastereomers δ [ppm]=1.18-1.29 (m, 6H), 3.15-3.29 (m, 1H), 4.15-4.25 (m, 2H), 4.84-4.90 (m, 1H).

Step 2: Ethyl (3R)-2-azido-4,4,4-trifluoro-3-methylbutanoate (diastereomer mixture)

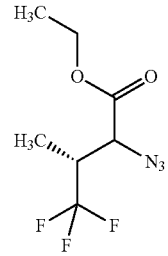

48.5 g of crude ethyl (3S)-2-bromo-4,4,4-trifluoro-3-methylbutanoate (diastereomer mixture) were dissolved in 130 ml of DMF, and 17.98 g (276.55 mmol) of sodium azide were added at RT. The reaction mixture was stirred vigorously at RT overnight. The mixture was then diluted with 600 ml of ethyl acetate and washed with a 1:1 mixture, adjusted to pH 8, of sat. sodium chloride solution and water. After phase separation, the aqueous phase was re-extracted with 200 ml of ethyl acetate. The combined organic phases were washed successively twice with in each case 100 ml and twice with in each case 50 ml of a 1:1 mixture of sat. sodium chloride solution and water, dried over sodium sulphate and concentrated under reduced pressure without heating. The residue was briefly dried under high vacuum (careful when venting). This gave 32.8 g of ethyl (3R)-2-azido-4,4,4-trifluoro-3-methylbutanoate (diastereomer mixture) as a crude product which was directly reacted further.

Step 3: Ethyl (3R)-4,4,4-trifluorovalinate (diastereomer mixture)

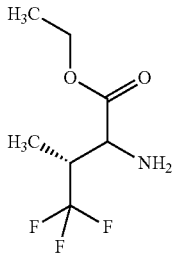

32.8 g of crude ethyl (3R)-2-azido-4,4,4-trifluoro-3-methylbutanoate (diastereomer mixture) were dissolved in 110 ml of ethanol and, after inertizing with argon, 6.98 g of palladium on carbon (5%) were added. The mixture was stirred overnight at standard pressure under an atmosphere of hydrogen, with the reaction vessel repeatedly being vented and filled with fresh hydrogen. The reaction mixture was then filtered off through Celite, the filter residue was washed with 50 ml of ethanol and the filtrate was concentrated under reduced pressure (up to about 20 mmHg). The slightly yellowish liquid that remained was briefly freed from residual solvent under high vacuum. This gave 23.5 g of the target compound as an about 70% pure crude product which was not purified any further (yield over three steps about 38% of theory).

GC-MS (Method 1): $R_t$=1.92 min and 2.01 min; in each case m/z=126 $(M-C_3H_5O_2)^+$.

$^1$H-NMR (400 MHz, DMSO-$d_6$): both diastereomers δ [ppm]=0.99-1.10 (m, 3H), 1.10-1.24 (m, 3H), 2.75-2.82 (m, 1H), 3.61/3.66 (in each case d, tog. 1H), 4.04-4.18 (m, 2H).

Example 28A

Ethyl (3R)—N-[(benzyloxy)carbonyl]-4,4,4-trifluorovalinate (diastereomer mixture)

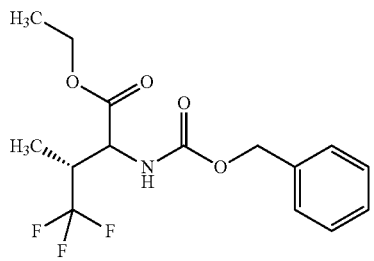 [SMILES: CCOC(=O)C(NC(=O)OCc1ccccc1)[C@@H](C)C(F)(F)F]

23.5 g of ethyl (3R)-4,4,4-trifluorovalinate (diastereomer mixture, crude product about 70%) and 18.1 ml (130 mmol) of triethylamine were dissolved in 235 ml of THF, and 32.3 g (130 mmol) of N-(benzyloxycarbonyloxy)succinimide were added. The reaction mixture was stirred at RT overnight and then diluted with ethyl acetate. The mixture was washed successively with sat. sodium bicarbonate solution, 1 N hydrochloric acid and sat. sodium chloride solution. The organic phase was dried over magnesium sulphate and concentrated under reduced pressure. The crude product was purified by chromatography on silica gel (mobile phase cyclohexane/ethyl acetate 6:1). This gave 22.1 g of the target product (about 80% of theory, diastereomer ratio about 2:1).

GC-MS (Method 1): $R_t$=6.02 min and 6.10 min; in each case m/z=333 (M)$^+$.

LC-MS (Method 2): $R_t$=1.13 min; m/z=334 (M+H)$^+$.

$^1$H-NMR (400 MHz, DMSO-$d_6$): both diastereomers δ [ppm]=1.10 (2d, tog. 3H), 1.15-1.23 (m, 3H), 2.80-3.07 (m, 1H), 4.08-4.21 (m, 2H), 4.38/4.62 (in each case dd, tog. 1H), 5.03-5.10 (m, 2H), 7.21-7.44 (m, 5H), 7.99 (2d, tog. 1H).

Example 29A (3R)—N-[(Benzyloxy)carbonyl]-4,4,4-trifluorovaline (diastereomer mixture)

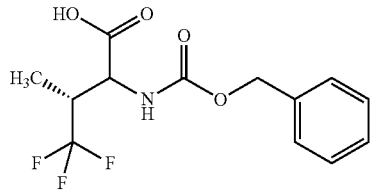 [SMILES: C[C@H](C(NC(=O)OCc1ccccc1)C(=O)O)C(F)(F)F]

2.15 g (6.45 mmol) of ethyl (3R)—N-[(benzyloxy)carbonyl]-4,4,4-trifluorovalinate (diastereomer mixture) were dissolved in a mixture of in each case 8 ml of THF, methanol and water, and 3.87 g (96.8 mmol) of sodium hydroxide were added at 0° C. Ice-cooling was removed and the reaction mixture was stirred at RT for 1 h. The mixture was then added to water, acidified with semiconcentrated hydrochloric acid and extracted with ethyl acetate. The organic phase was washed with sat. sodium chloride solution, dried over sodium sulphate and concentrated under reduced pressure. This gave 1.95 g of the target product which was not purified any further (99% of theory, diastereomer ratio about 2.8:1).

LC-MS (Method 5): $R_t$=2.01 min; m/z=306 (M+H)$^+$.

$^1$H-NMR (400 MHz, DMSO-$d_6$): both diastereomers δ [ppm]=1.09/1.11 (in each case d, tog. 3H), 2.79-3.06 (m, 1H), 4.31/4.61 (in each case dd, tog. 1H), 5.05-5.09 (m, 2H), 7.26-7.40 (m, about 5H), 7.76/7.83 (in each case d, tog. 1H), 12.63 (br. s, 1H).

Example 30A

Ethyl (3R)—N-[(allyloxy)carbonyl]-4,4,4-trifluorovalinate (diastereomer mixture)

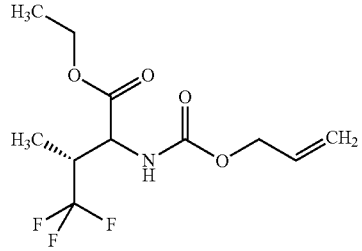 [SMILES: C=CCOC(=O)NC(C(=O)OCC)[C@@H](C)C(F)(F)F]

9.7 ml (69.3 mmol) of triethylamine were added dropwise to a solution of 6.38 g (55.4 mmol) of succinimide in 90 ml of abs. THF. The resulting suspension was cooled to 0° C., and a solution of 6.68 g (55.4 mmol) of allyl chloroformate in 10 ml of abs. THF was added dropwise. The mixture was stirred at 0° C. for 1 h, and three portions of in total 9.2 g (about 46 mmol) of ethyl (3R)-4,4,4-trifluorovalinate (diastereomer mixture, crude product) were added. The reaction mixture was warmed to RT overnight, then diluted with ethyl acetate, washed with sat. sodium bicarbonate solution and sat. sodium chloride solution, dried over sodium sulphate and concentrated under reduced pressure. The crude product was purified by chromatography on silica gel (mobile phase cyclohexane/ethyl acetate 10:1→4:1). This gave 6.50 g of the target product (about 50% of theory, diastereomer ratio about 2:1).

GC-MS (Method 1): $R_t$=3.96 min and 4.06 min; in each case m/z=210 $(M-C_3H_5O_2)^+$.

$^1$H-NMR (400 MHz, DMSO-$d_6$): both diastereomers δ [ppm]=1.07-1.13 (m, 3H), 1.17-1.23 (m, 3H), 2.82-3.05 (m, 1H), 4.10-4.18 (m, 2H), 4.36/4.60 (in each case dd, tog. 1H), 4.48-4.54 (m, 2H), 5.19 (d, 1H), 5.30 (d, 1H), 5.82-5.98 (m, 1H), 7.84-7.96 (m, 1H).

Example 31A (3R)—N-[(Allyloxy)carbonyl]-4,4,4-trifluorovaline (diastereomer mixture)

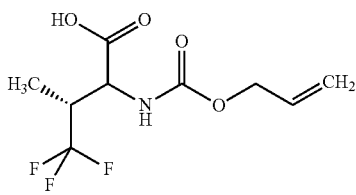 [SMILES: C=CCOC(=O)NC(C(=O)O)[C@@H](C)C(F)(F)F]

6.50 g (22.9 mmol) of ethyl (3R)—N-[(allyloxy)carbonyl]-4,4,4-trifluorovalinate (diastereomer mixture) were dissolved in a mixture of in each case 28 ml of THF, ethanol and water, and 13.77 g (344 mmol) of sodium hydroxide were added at 0° C. Ice-cooling was removed and the reaction mixture was stirred at RT overnight. The mixture was then added to water, acidified with semiconcentrated hydrochloric acid and extracted with ethyl acetate. The organic phase was washed with sat. sodium chloride solution, dried over sodium sulphate and concentrated under reduced pressure. This gave 4.39 g of the target product which was not purified any further (75% of theory, diastereomer ratio about 2.5:1).

MS (DCI): m/z=186 (M-CF$_3$)$^+$.

$^1$H-NMR (400 MHz, DMSO-d$_6$): both diastereomers δ [ppm]=1.07-1.11 (m, 3H), 2.83-3.03 (m, 1H), 4.28/4.57 (in each case dd, tog. 1H), 4.47-4.53 (m, 2H), 5.19 (d, 1H), 5.30 (d, 1H), 5.83-5.98 (m, 1H), 7.70/7.78 (in each case d, tog. 1H).

Example 32A tert-Butyl 1-[3-({N-[(benzyloxy)carbonyl]-4,4,4-trifluorovalyl}amino)-4-fluorobenzyl]cyclopropanecarboxylate (racemic diastereomer mixture)

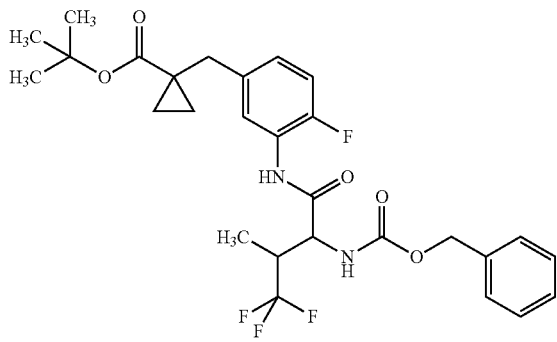 [SMILES: CC(C(NC(=O)OCc1ccccc1)C(=O)Nc1cc(CC2(C(=O)OC(C)(C)C)CC2)ccc1F)C(F)(F)F]

4.80 g (15.7 mmol) of N-[(benzyloxy)carbonyl]-4,4,4-trifluorovaline (racemic diastereomer mixture) and 5.01 g (18.9 mmol) of tert-butyl 1-(3-amino-4-fluorobenzyl)cyclopropanecarboxylate were dissolved in a mixture of 40 ml of DMF and 10 ml of pyridine, and 6.58 g (17.3 mmol) of HATU were added at RT. The reaction mixture was stirred at RT overnight and then added to water. The mixture was extracted three times with ethyl acetate, and the combined organic phases were then washed successively with sat. sodium bicarbonate solution, 1 N hydrochloric acid and sat. sodium chloride solution, dried over magnesium sulphate and concentrated under reduced pressure. The crude product was purified by chromatography on silica gel (mobile phase cyclohexane/ethyl acetate 20:1→10:1). This gave 5.34 g of the target product (61.5% of theory, diastereomer ratio about 2.5:1).

LC-MS (Method 5): R$_t$=2.84 min; m/z=497 (M-C$_4$H$_7$)$^+$.

$^1$H-NMR (400 MHz, DMSO-d$_6$): both diastereomers δ [ppm]=0.80-0.86 (m, 2H), 1.03-1.09 (m, 2H), 1.12 (d, 3H), 1.28/1.29 (in each case s, tog. 9H), 2.78-2.83 (m, 2H), 2.97-3.07 (m, 1H), 4.67/4.84 (t and dd, tog. 1H), 5.07/5.08 (in each case s, tog. 2H), 7.02-7.10 (m, 1H), 7.17 (dd, 1H), 7.28-7.40 (m, 5H), 7.62/7.67 (in each case dd, tog. 1H), 7.80-7.89 (m, 1H), 9.98/10.12 (in each case s, tog. 1H).

Example 33A tert-Butyl 3-[3-({N-[(benzyloxy)carbonyl]-4,4,4-trifluorovalyl}amino)-4-fluorophenyl]propanoate (racemic diastereomer mixture)

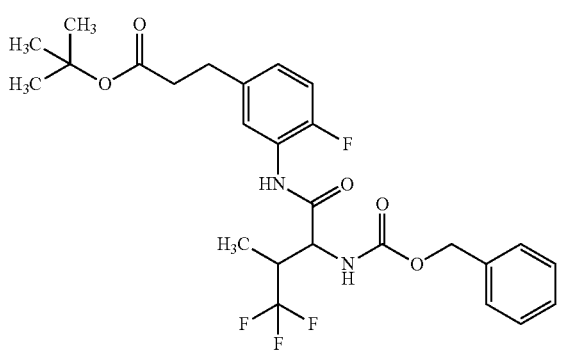 [SMILES: CC(C(NC(=O)OCc1ccccc1)C(=O)Nc1cc(CCC(=O)OC(C)(C)C)ccc1F)C(F)(F)F]

10.30 g (33.7 mmol) of N-[(benzyloxy)carbonyl]-4,4,4-trifluorovaline (racemic diastereomer mixture) and 9.69 g (40.5 mmol) of tert-butyl 3-(3-amino-4-fluorobenzyl)propanoate were dissolved in a mixture of 40 ml of DMF and 10 ml of pyridine, and 16.68 g (43.9 mmol) of HATU were added at RT. The reaction mixture was stirred at RT overnight and then diluted with ethyl acetate. The mixture was washed successively with sat. sodium bicarbonate solution, 1 N hydrochloric acid and sat. sodium chloride solution, dried over magnesium sulphate and concentrated under reduced pressure. The crude product was pre-purified by chromatography on silica gel (mobile phase cyclohexane/ethyl acetate 10:1). Product-containing fractions were concentrated under reduced pressure and the residue was stirred with cyclohexane/diethyl ether 5:1. The solid obtained was filtered off with suction and dried under high vacuum. This gave 12.29 g of the target product (69% of theory, diastereomer ratio about 2.5:1).

LC-MS (Method 2): R$_t$=1.29 min; m/z=471 (M-C$_4$H$_7$)$^+$.

$^1$H-NMR (400 MHz, DMSO-d$_6$): both diastereomers δ [ppm]=1.12 (d, 3H), 1.30-1.37 (m, 9H), 2.48 (t, about 2H), 2.78 (t, 2H), 2.95-3.08 (m, 1H), 4.67/4.84 (t and dd, tog. 1H), 5.07/5.08 (in each case s, tog. 2H), 7.00-7.08 (m, 1H), 7.16 (dd, 1H), 7.26-7.44 (m, 5H), 7.55-7.63 (m, 1H), 7.77-7.88 (m, 1H), 9.96/10.10 (in each case s, tog. 1H).

General Procedure 1: HATU-Mediated Amide Coupling of N-Protected 4,4,4-Trifluorovaline Derivatives with Anilines At RT, HATU (1.0 to 2.0 eq.) is added to a solution of the N-protected 4,4,4-trifluorovaline derivative in question (about 0.8 to 1.5 eq., 0.15 to 1.5 mol/l) and an aniline (about 0.8 to 1.5 eq., 0.15 to 1.5 mol/l) in a mixture of DMF and pyridine (mixing ratio about 3:1 to 1.5:1). Alternatively, instead of pyridine it is also possible to use N,N-diisopropylethylamine (2.0 to 5.0 eq.). The resulting mixture is stirred at a temperature of from RT to 60° C. for 4 h to 48 h. If appropriate, after 24 h a further portion of aniline component or of trifluorovaline derivative and HATU is added. After the reaction has ended, the crude product can, after removal of the solvent under reduced pressure, be purified by preparative RP-HPLC (mobile phase: acetonitrile/water gradient) or alternatively, following aqueous work-up of the reaction mixture, by chromatography on silica gel (mobile phases: cyclohexane/diethyl ether, petroleum ether/ethyl acetate, cyclohexane/ethyl acetate or dichloromethane/methanol mixtures).

The following examples were prepared according to General Procedure 1:

| Example | Name/Structure/Starting materials | Analytical data |
| --- | --- | --- |
| 34A | tert-butyl 3-[3-({N-[(benzyloxy)carbonyl]-4,4,4-trifluorovalyl}amino)-4-chlorophenyl]propanoate (racemic diastereomer mixture) 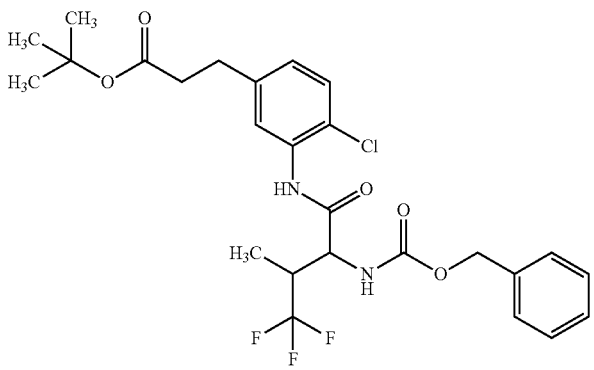 from N-[(benzyloxy)carbonyl]-4,4,4-trifluorovaline (racemic diastereomer mixture) and tert-butyl 3-(3-amino-4-chlorophenyl)propanoate | LC-MS (Method 3): $R_t$ = 1.52 min; m/z = 487 $(M - C_4H_7)^+$. $^1$H-NMR (400 MHz, DMSO-$d_6$): both diastereomers δ [ppm] = 1.15 (d, 3H), 1.35 (s, 9H), 2.79 (t, 2H), 3.02-3.18 (m, 1H), 4.65/4.85 (t and dd, tog. 1H), 5.03-5.16 (m, 2H), 7.10 (dd, 1H), 7.27-7.43 (m, 6H), 7.49 (s, 1H), 7.89 (d, 1H), 9.75/9.89 (in each case s, tog. 1H). Diastereomer ratio about 7:1 |
| 35A | tert-butyl 3-[3-({(3R)-N-[(benzyloxy)carbonyl]-4,4,4-trifluorovalyl}amino)-4-chlorophenyl]propanoate (diastereomer mixture) 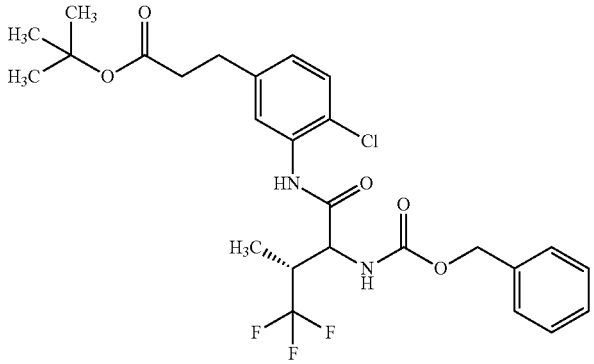 [SMILES: CC(C(NC(=O)OCc1ccccc1)C(=O)Nc1cc(CCC(=O)OC(C)(C)C)ccc1Cl)C(F)(F)F] from (3R)-N-[(benzyloxy)carbonyl]-4,4,4-trifluorovaline (diastereomer mixture) and tert-butyl-3-(3-amino-4-chlorophenyl)propanoate | LC-MS (Method 2): $R_t$ = 1.27 min; m/z = 487 $(M - C_4H_7)^+$. $^1$H-NMR (400 MHz, DMSO-$d_6$): main diastereomer δ [ppm] = 1.15 (d, 3H), 1.35 (s, 9H), 2.49 (t, obscured, about 2H), 2.79 (t, 2H), 4.85 (dd, 1H), 5.10 (d, 2H), 7.10 (dd, 1H), 7.27-7.44 (m, 7H), 7.49 (s, 1H), 7.89 (d, 1H), 9.75 (s, 1H). |

| Example | Name/Structure/Starting materials | Analytical data |
|---|---|---|
| 36A | ethyl (2S)-3-[3-({N-[(benzyloxy)carbonyl]-4,4,4-trifluorovalyl}amino)-4-fluorophenyl]-2-methylpropanoate (isomer mixture)<br>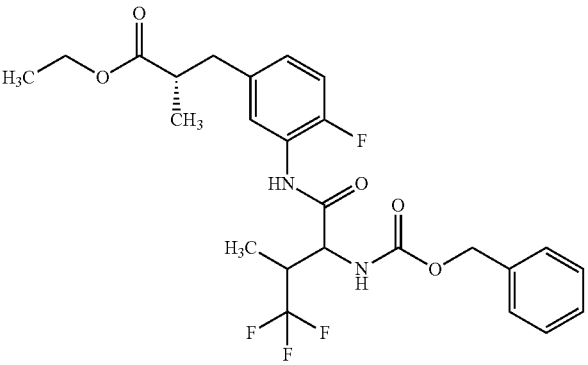<br>from N-[(benzyloxy)carbonyl]-4,4,4-trifluorovaline (racemic diastereomer mixture) and (+)-ethyl (2S)-3-(3-amino-4-fluorophenyl)-2-methylpropanoate | LC-MS (Method 3): $R_t$ = 1.40 min; m/z = 469 $(M - C_2H_3O)^+$. $^1$H-NMR (400 MHz, DMSO-$d_6$): both diastereomers δ (ppm) = 1.00-1.16 (m, 9H), 2.61-2.72 (m, 2H), 2.75-2.87 (m, 1H), 2.97-3.08 (m, 1H), 4.00 (q, 2H), 4.67/4.84 (t and dd, tog. 1H), 5.04-5.11 (m, 2H), 6.94-7.04 (m, 1H), 7.16 (dd, 1H), 7.27-7.41 (m, 5H), 7.49-7.59 (m, 1H), 7.82 (d, 1H), 9.97/10.11 (in each case s, tog. 1H). Diastereomer ratio about 3.8:1 |
| 37A | ethyl (2R)-3-[3-({N-(benzyloxy)carbonyl]-4,4,4-trifluorovalyl}amino)-4-fluorophenyl]-2-methylpropanoate (isomer mixture)<br>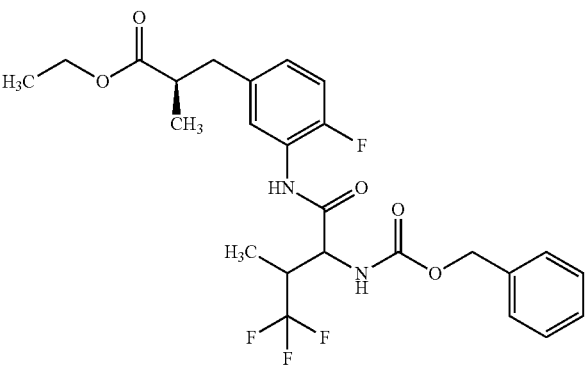 [SMILES: CCOC(=O)[C@H](C)Cc1ccc(F)c(NC(=O)C(NC(=O)OCc2ccccc2)C(C)C(F)(F)F)c1]<br>from N-[(benzyloxy)carbonyl]-4,4,4-trifluorovaline (racemic diastereomer mixture) and (−)-ethyl (2R)-3-(3-amino-4-fluorophenyl)-2-methylpropanoate | LC-MS (Method 2): $R_t$ = 1.24 min; m/z = 511 $(M - H)^-$. $^1$H-NMR (400 MHz, DMSO-$d_6$): both diastereomers δ [ppm] = 1.03-1.15 (m, 9H), 2.61-2.72 (m, 2H), 2.78-2.87 (m, 1H), 2.97-3.08 (m, 1H), 4.00 (q, 2H), 4.67/4.84 (t and dd, tog. 1H), 5.04-5.11 (m, 2H), 6.95-7.04 (m, 1H), 7.16 (dd, 1H), 7.27-7.41 (m, 5H), 7.49-7.59 (m, 1H), 7.82 (d, 1H), 9.97/10.11 (in each case s, tog. 1H). Diastereomer ratio about 4.5:1 |

| Example | Name/Structure/Starting materials | Analytical data |
|---|---|---|
| 38A | ethyl (2R)-3-[3-({N-[(allyloxy)carbonyl]-4,4,4-trifluorovalyl}amino)-4-chlorophenyl]-2-methylpropanoate (isomer mixture)<br><br>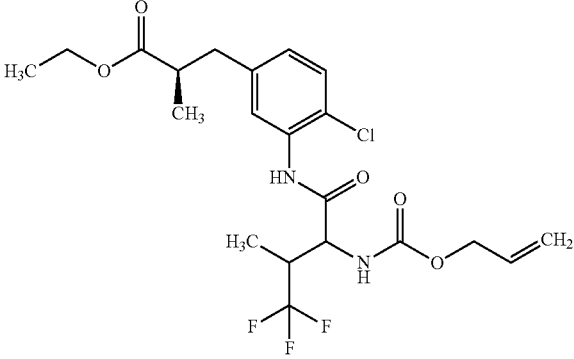 [SMILES: C=CCOC(=O)NC(C(=O)Nc1cc(C[C@@H](C)C(=O)OCC)ccc1Cl)C(C)C(F)(F)F]<br><br>from N-[(allyloxy)carbonyl]-4,4,4-trifluorovaline (racemic diastereomer mixture) and (−)-ethyl (2R)-3-(3-amino-4-chlorophenyl)-2-methylpropanoate | LC-MS (Method 2): $R_t$ = 1.24 min; m/z = 479 (M + H)⁺.<br>$^1$H-NMR (400 MHz, DMSO-$d_6$): both diastereomers δ [ppm] = 1.05-1.17 (m, 9H), 2.63-2.74 (m, 2H), 2.78-2.90 (m, 1H), 3.03-3.12 (m, 1H), 4.01 (q, 2H), 4.51-4.56 (m, 2H), 4.63/4.83 (t and dd, tog. 1H), 5.15-5.23 (m, 1H), 5.32 (dd, 1H), 5.92 (ddd, 1H), 7.02-7.09 (m, 1H), 7.37-7.49 (m, 2H), 7.75-7.82 (m, 1H), 9.76/9.89 (in each case s, tog. 1H).<br>Diastereomer ratio about 8:1 |
| 39A | ethyl (2S)-3-[3-({N-[(allyloxy)carbonyl]-4,4,4-trifluorovalyl}amino)-4-chlorophenyl]-2-methylpropanoate (isomer mixture)<br><br>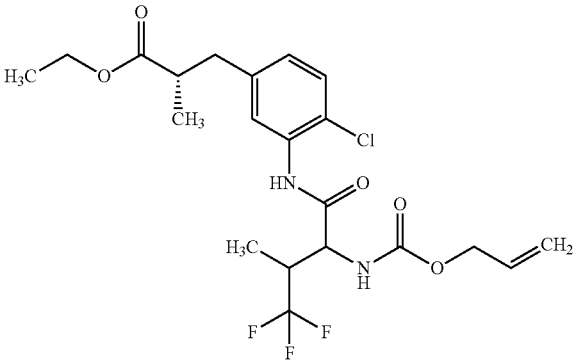 [SMILES: C=CCOC(=O)NC(C(=O)Nc1cc(C[C@H](C)C(=O)OCC)ccc1Cl)C(C)C(F)(F)F]<br><br>from N-[(allyloxy)carbonyl]-4,4,4-trifluorovaline (racemic diastereomer mixture) and (+)-ethyl (2S)-3-(3-amino-4-chlorophenyl)-2-methylpropanoate | LC-MS (Method 2): $R_t$ = 1.23 min; m/z = 479 (M + H)⁺.<br>$^1$H-NMR (400 MHz, DMSO-$d_6$): both diastereomers δ [ppm] = 1.04-1.18 (m, 9H), 2.64-2.74 (m, 2H), 2.79-2.89 (m, 1H), 2.95-3.14 (m, 1H), 4.01 (q, 2H), 4.47-4.57 (m, 2H), 4.67/4.83 (in each case dd, tog. 1H), 5.15-5.39 (m, 2H), 5.84-5.99 (m, 1H), 7.06 (dd, 1H), 7.35-7.48 (m, 2H), 7.82/7.97 (in each case d, tog. 1H), 9.76 (s, 1H).<br>Diastereomer ratio about 4.2:1 |

| Example | Name/Structure/Starting materials | Analytical data |
|---|---|---|
| 40A | tert-butyl (3R)-3-[3-({N-[(allyloxy)carbonyl]-4,4,4-trifluorovalyl}amino)-4-chlorophenyl]butanoate (isomer mixture)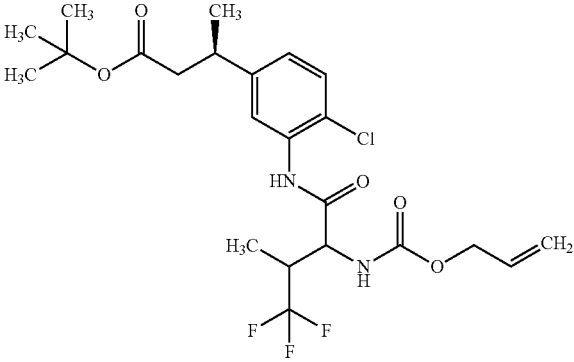 [SMILES: C=CCOC(=O)NC(C(=O)Nc1cc([C@H](C)CC(=O)OC(C)(C)C)ccc1Cl)C(C)C(F)(F)F]from N-[(allyloxy)carbonyl]-4,4,4-trifluorovaline (racemic diastereomer mixture) and (+)-tert-butyl (3R)-3-(3-amino-4-chlorophenyl)butanoate | LC-MS (Method 2): $R_t$ = 1.29 min; m/z = 507 (M + H)$^+$.<br>$^1$H-NMR (400 MHz, DMSO-$d_6$): main diastereomer $\delta$ [ppm] = 1.15 (d, 3H), 1.19 (d, 3H), 1.30 (s, 9H), 2.39-2.47 (m, about 2H), 3.03-3.15 (m, 2H), 4.54 (d, 2H), 4.84 (dd, 1H), 5.19 (d, 1H), 5.32 (d, 1H), 5.92 (ddd, 1H), 7.14 (d, 1H), 7.42 (d, 1H), 7.51 (s, 1H), 7.82 (d, 1H), 9.76 (s, 1H). |
| 41A | tert-butyl (3S)-3-[3-({N-[(allyloxy)carbonyl]-4,4,4-trifluorovalyl}amino)-4-chlorophenyl]butanoate (isomer mixture)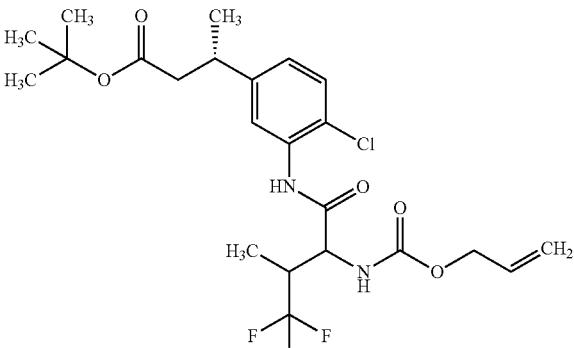from N-[(allyloxy)carbonyl]-4,4,4-trifluorovaline (racemic diastereomer mixture) and (−)-tert-butyl (3S)-3-(3-amino-4-chlorophenyl)butanoate | LC-MS (Method 2): $R_t$ = 1.33 min; m/z = 507 (M + H)$^+$.<br>1H-NMR (400 MHz, DMSO-$d_6$): main diastereomer $\delta$ [ppm] = 1.15 (d, 3H), 1.19 (d, 3H), 1.30 (s, 9H), 2.39-2.48 (m, about 2H), 3.03-3.15 (m, 2H), 4.54 (d, 2H), 4.84 (dd, 1H), 5.19 (dd, 1H), 5.32 (dd, 1H), 5.85-5.99 (m, 1H), 7.14 (d, 1H), 7.42 (d, 1H), 7.51 (s, 1H), 7.82 (d, 1H), 9.76 (s, 1H). |
| 42A | tert-Butyl (3S)-3-[3-({(3R)-N-[(allyloxy)carbonyl]-4,4,4-trifluorovalyl}amino)-4-chlorophenyl]butanoate (diastereomer mixture)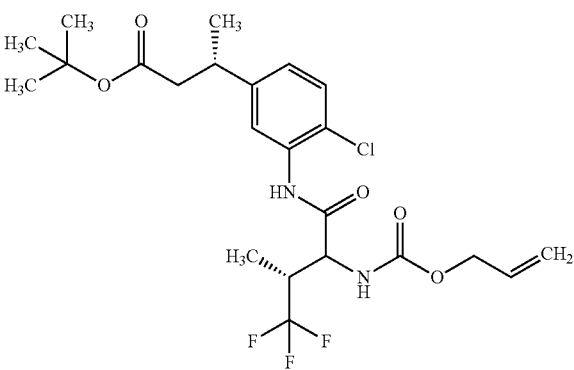 [SMILES: C=CCOC(=O)NC(C(=O)Nc1cc([C@@H](C)CC(=O)OC(C)(C)C)ccc1Cl)C(C)C(F)(F)F]from (3R)-N-[(allyloxy)carbonyl]-4,4,4-trifluorovaline (diastereomer mixture) and (−)-tert-butyl (3S)-3-(3-amino-4-chlorophenyl)butanoate | LC-MS (Method 2): $R_t$ = 1.30 min; m/z = 505 (M − H)$^-$.<br>$^1$H-NMR (400 MHz, DMSO-$d_6$): main diastereomer $\delta$ [ppm] = 1.14-1.21 (m, 6H), 1.30 (s, 9H), 2.39-2.48 (m, about 2H), 3.02-3.15 (m, 2H), 4.54 (d, 2H), 4.84 (dd, 1H), 5.19 (d, 1H), 5.28-5.36 (m, 1H), 5.83-5.99 (m, 1H), 7.14 (dd, 1H), 7.42 (d, 1H), 7.50 (s, 1H), 7.83 (d, 1H), 9.78 (s, 1H). |

Example 43A

Ethyl (2S)-3-[3-({(3R)—N-[(benzyloxy)carbonyl]-4,4,4-trifluorovalyl}amino)-4-fluorophenyl]-2-methyl-propanoate (diastereomer mixture)

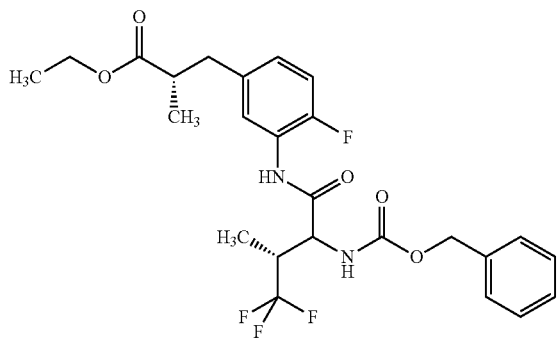 [SMILES: CCOC(=O)[C@@H](C)Cc1ccc(F)c(NC(=O)C(NC(=O)OCc2ccccc2)[C@@H](C)C(F)(F)F)c1]

0.87 g (2.85 mmol) of (3R)—N-[(benzyloxy)carbonyl]-4,4,4-trifluorovaline (diastereomer mixture) and 0.77 g (3.42 mmol) of (+)-ethyl (2S)-3-(3-amino-4-fluorophenyl)-2-methylpropanoate were dissolved in a mixture of 5 ml of DMF and 2.5 ml of pyridine, and 1.41 g (3.71 mmol) of HATU were added at RT. The reaction mixture was stirred at RT overnight and then diluted with ethyl acetate. The mixture was washed successively with 1 N hydrochloric acid, sat. sodium bicarbonate solution and sat. sodium chloride solution, dried over magnesium sulphate and concentrated under reduced pressure. The crude product was purified by chromatography on silica gel (mobile phase cyclohexane/ethyl acetate 6:1). This gave 1.27 g of the target product (87.2% of theory, diastereomer ratio about 4.8:1).

LC-MS (Method 3): $R_t$=1.41 min; m/z=513 (M+H)$^+$.

$^1$H-NMR (400 MHz, DMSO-d$_6$): both diastereomers δ [ppm]=1.04-1.15 (m, 9H), 2.62-2.72 (m, about 2H), 2.76-2.86 (m, 1H), 2.96-3.06 (m, 1H), 3.96-4.05 (m, 2H), 4.84 (dd, 1H), 5.07/5.08 (in each case s, tog. 2H), 7.01 (td, 1H), 7.17 (dd, 1H), 7.27-7.41 (m, 5H), 7.50-7.59 (m, 1H), 7.82-7.88 (m, 1H), 9.99/10.13 (in each case s, tog. 1H).

Example 44A

Ethyl (2S)-3-[3-({(3R)—N-[(benzyloxy)carbonyl]-4,4,4-trifluorovalyl}amino)-4-chlorophenyl]-2-methyl-propanoate (diastereomer mixture)

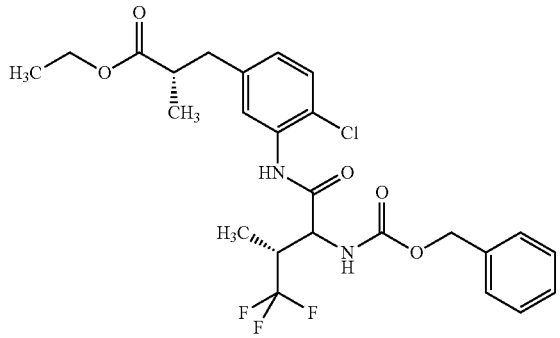 [SMILES: CCOC(=O)[C@@H](C)Cc1ccc(Cl)c(NC(=O)C(NC(=O)OCc2ccccc2)[C@@H](C)C(F)(F)F)c1]

1.26 g (purity 76%, about 3.14 mmol) of (3R)—N-[(benzyloxy)carbonyl]-4,4,4-trifluorovaline (diastereomer mixture) and 0.91 g (3.76 mmol) of (+)-ethyl (2S)-3-(3-amino-4-chlorophenyl)-2-methylpropanoate were dissolved in a mixture of 10 ml of DMF and 4 ml of pyridine, and 1.55 g (4.08 mmol) of HATU were added at RT. The reaction mixture was stirred at RT overnight and then added to water. The mixture was extracted three times with ethyl acetate, and the combined organic phases were then washed successively with sat. sodium bicarbonate solution, 1 N hydrochloric acid and sat. sodium chloride solution, dried over magnesium sulphate and concentrated under reduced pressure. The resulting solid was stirred in a mixture of cyclohexane and diethyl ether (about 3:1), filtered off with suction and dried under high vacuum. This gave 0.99 g of the target product (59.9% of theory, diastereomer ratio about 7:1).

LC-MS (Method 2): $R_t$=1.32 min; m/z=529 (M+H)$^+$.

$^1$H-NMR (400 MHz, DMSO-d$_6$): main diastereomer δ [ppm]=1.03-1.18 (m, 9H), 2.62-2.75 (m, 2H), 2.80-2.90 (m, 1H), 3.03-3.13 (m, 1H), 4.01 (q, 2H), 4.85 (dd, 1H), 5.04-5.16 (m, 2H), 7.06 (dd, 1H), 7.25-7.49 (m, about 7H), 7.89 (d, 1H), 9.75 (s, 1H).

Example 45A tert-Butyl 1-[3-({(3R)—N-[(allyloxy)carbonyl]-4,4,4-trifluorovalyl}amino)-4-chlorobenzyl]cyclopropanecarboxylate (diastereomer mixture)

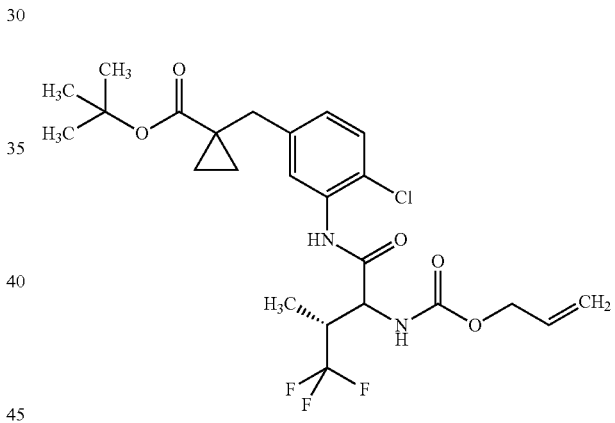

398.5 mg (1.56 mmol) of (3R)—N-[(allyloxy)carbonyl]-4,4,4-trifluorovaline (diastereomer mixture) and 400 mg (1.42 mmol) of tert-butyl 1-(3-amino-4-chlorobenzyl)cyclopropanecarboxylate were dissolved in a mixture of 4.7 ml of DMF and 1.6 ml of pyridine, and 647.8 mg (1.70 mmol) of HATU were added at RT. The reaction mixture was stirred at RT overnight. A further 400 mg (1.42 mmol) of tert-butyl 1-(3-amino-4-chlorobenzyl)cyclopropanecarboxylate and 647.8 mg (1.70 mmol) of HATU were added, and the reaction mixture was stirred at 50° C. for another 4 h. After dilution with ethyl acetate, the mixture was washed successively with sat. sodium bicarbonate solution, 1 N hydrochloric acid and sat. sodium chloride solution, dried over magnesium sulphate and concentrated under reduced pressure. The crude product was purified by preparative RP-HPLC (mobile phase: acetonitrile/water). This gave 453 mg of the target product (55.9% of theory, diastereomer ratio >8:1).

LC-MS (Method 2): $R_t$=1.31 min; m/z=519 (M+H)$^+$.

$^1$H-NMR (400 MHz, DMSO-d$_6$): δ [ppm]=0.84 (q, 2H), 1.04-1.09 (m, 2H), 1.15 (d, 3H), 1.30 (s, 9H), 2.83 (s, 2H), 3.02-3.11 (m, 1H), 4.54 (d, 2H), 4.79-4.86 (m, 1H), 5.19 (d, 1H), 5.28-5.35 (m, 1H), 5.84-5.99 (m, 1H), 7.12 (dd, 1H), 7.40-7.45 (m, 1H), 7.49-7.56 (m, 1H), 7.84 (d, 1H), 9.78 (s, 1H).

Example 46A and Example 47A (+/−)-tert-Butyl 1-{4-fluoro-3-[(4,4,4-trifluorovalyl)amino]benzyl}cyclopropanecarboxylate (diastereomer 1 and 2)

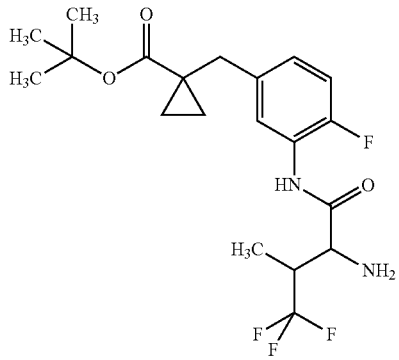 [SMILES: CC(C(N)C(=O)Nc1cc(CC2(C(=O)OC(C)(C)C)CC2)ccc1F)C(F)(F)F]

5.31 g (9.61 mmol) of tert-butyl 1-[3-({N-[(benzyloxy)carbonyl]-4,4,4-trifluorovalyl}amino)-4-fluorobenzyl]cyclopropanecarboxylate (Example 32A, racemic diastereomer mixture) were dissolved in a mixture of 100 ml of ethanol and 20 ml of THF. The solution was inertized with argon, and 511 mg of palladium on carbon (10%) were added. The reaction mixture was stirred vigorously at standard pressure under an atmosphere of hydrogen overnight. After filtration through kieselguhr and washing with ethanol/THF, the filtrate was concentrated under reduced pressure. The residue was purified by chromatography on silica gel (mobile phase cyclohexane/ethyl acetate 50:1→4:1) and the diastereomers were separated:

Example 46A

Diastereomer 1

Yield: 3.03 g (75.4% of theory)

LC-MS (Method 2): $R_t$=1.05 min; m/z=419 (M+H)$^+$.

$^1$H-NMR (400 MHz, DMSO-d$_6$): δ [ppm]=0.80-0.86 (m, 2H), 1.00-1.10 (m, 5H), 1.30 (s, 9H), 2.75-2.87 (m, 2H), 2.92-3.04 (m, 1H), 3.80 (br. s, 1H), 6.95-7.07 (m, 1H), 7.18 (dd, 1H), 7.99 (dd, 1H), 10.01 (br. s, about 1H).

Example 47A

Diastereomer 2

Yield: 0.88 g (21.9% of theory)

LC-MS (Method 2): $R_t$=0.96 min; m/z=419 (M+H)$^+$.

$^1$H-NMR (400 MHz, DMSO-d$_6$): δ [ppm]=0.79-0.85 (m, 2H), 1.04-1.10 (m, 2H), 1.18 (d, 3H), 1.30 (s, 9H), 2.81 (s, 2H), 2.86-2.97 (m, 1H), 3.61 (br. s, 1H), 6.93-7.04 (m, 1H), 7.17 (dd, 1H), 7.93 (dd, 1H), 9.89 (br. s, about 1H).

Example 48A and Example 49A (+/−)-tert-Butyl 3-{4-fluoro-3-[(4,4,4-trifluorovalyl)amino]phenyl}propanoate (diastereomers 1 and 2)

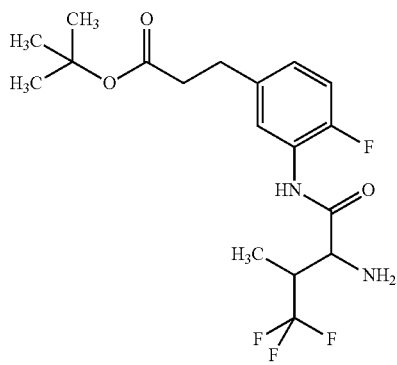 [SMILES: CC(C(N)C(=O)Nc1cc(CCC(=O)OC(C)(C)C)ccc1F)C(F)(F)F]

12.29 g (23.3 mmol) of tert-butyl 3-[3-({N-[(benzyloxy)carbonyl]-4,4,4-trifluorovalyl}amino)-4-fluorophenyl]propanoate (Example 33A, racemic diastereomer mixture) were dissolved in a mixture of 80 ml of ethanol and 20 ml of THF. The solution was inertized with argon, and 745 mg of palladium on carbon (10%) were added. The reaction mixture was stirred vigorously at standard pressure under an atmosphere of hydrogen overnight. After filtration through kieselguhr and washing with ethanol/THF, the filtrate was concentrated under reduced pressure. The residue was purified by chromatography on silica gel (mobile phase cyclohexane/ethyl acetate 20:1→4:1) and the diastereomers were separated:

Example 48A

Diastereomer 1

Yield: 5.72 g (62.5% of theory)

LC-MS (Method 2): $R_t$=0.92 min; m/z=393 (M+H)$^+$.

$^1$H-NMR (400 MHz, DMSO-d$_6$): δ [ppm]=1.04 (d, 3H), 1.35 (s, 9H), 2.49 (t, about 2H, obscured), 2.78 (t, 2H), 2.92-3.04 (m, 1H), 3.80 (br. s, 1H), 6.85-7.04 (m, 1H), 7.18 (dd, 1H), 7.92 (dd, 1H).

Example 49A

Diastereomer 2

Yield: 2.61 g (28.5% of theory)

LC-MS (Method 2): $R_t$=0.87 min; m/z=393 (M+H)$^+$.

$^1$H-NMR (400 MHz, DMSO-d$_6$): δ [ppm]=1.18 (d, 3H), 1.35 (s, 9H), 2.49 (t, about 2H, obscured), 2.78 (t, 2H), 2.84-2.97 (m, 1H), 3.55-3.66 (m, 1H), 7.00 (td, 1H), 7.17 (dd, 1H), 7.86 (dd, 1H).

Example 50A (+)-tert-Butyl 3-(4-fluoro-3-{[(3R)-4,4,4-trifluoro-D-valyl]amino}phenyl)propanoate

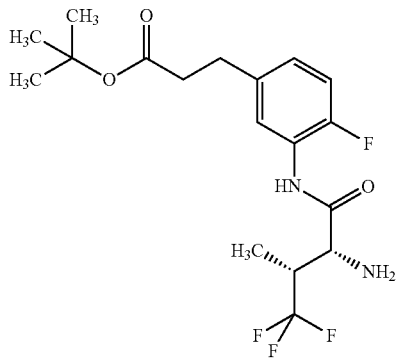 [SMILES: C[C@H]([C@@H](N)C(=O)Nc1cc(CCC(=O)OC(C)(C)C)ccc1F)C(F)(F)F]

The racemic diastereomer 1, obtained above, of tert-butyl 3-{4-fluoro-3-[(4,4,4-trifluorovalyl)amino]phenyl}propanoate (Example 48A) was separated into the enantiomers by preparative HPLC on a chiral phase [column: Daicel Chiralpak AD-H, 5 μm, 250 mm×20 mm; injection volume: 0.25 ml; temperature: 45° C.; mobile phase: 80% isohexane/20% ethanol (+0.2% diethylamine); flow rate: 15 ml/min; detection: 220 nm]. 5.70 g of racemate gave 2.59 g of the title compound (as enantiomer 2).

LC-MS (Method 2): $R_t$=0.93 min; m/z=393 (M+H)$^+$.

$^1$H-NMR (400 MHz, DMSO-d$_6$): δ [ppm]=1.04 (d, 3H), 1.35 (s, 9H), 2.49 (t, about 2H, obscured), 2.78 (t, 2H), 2.92-3.04 (m, 1H), 3.80 (br. s, 1H), 6.95-7.03 (m, 1H), 7.19 (dd, 1H), 7.92 (dd, 1H).

$[α]_D^{20}$=+24.2°, c=0.500, chloroform.

Example 51A and Example 52A (+/−)-tert-Butyl 3-{4-chloro-3-[(4,4,4-trifluorovalyl)amino]phenyl}propanoate (diastereomers 1 and 2)

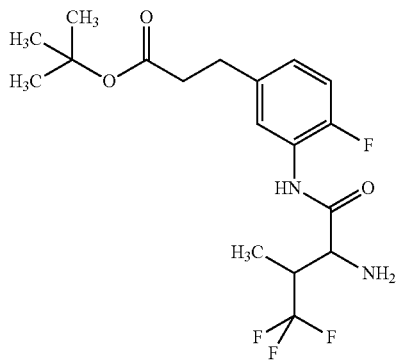 [SMILES: CC(C(N)C(=O)Nc1cc(CCC(=O)OC(C)(C)C)ccc1F)C(F)(F)F]

3.19 g (5.87 mmol) of tert-butyl 3-[3-({N-[(benzyloxy)carbonyl]-4,4,4-trifluorovalyl}amino)-4-chlorophenyl]propanoate (Example 34A, racemic diastereomer mixture) were dissolved in 50 ml of ethyl acetate. The solution was inertized with argon, and 125 mg of palladium on carbon (5%) were added. The reaction mixture was stirred vigorously at standard pressure under an atmosphere of hydrogen for 3 h. After filtration through kieselguhr, the filtrate was concentrated under reduced pressure. The residue was purified by chromatography on silica gel (mobile phase cyclohexane/ethyl acetate 50:1→3:1) and the diastereomers were separated:

Example 51A

Diastereomer 1

Yield: 1.73 g (72.1% of theory)

LC-MS (Method 2): $R_t$=1.09 min; m/z=409 (M+H)$^+$.

$^1$H-NMR (400 MHz, DMSO-d$_6$): δ [ppm]=1.04 (d, 3H), 1.35 (s, 9H), 2.48-2.53 (m, about 2H, obscured), 2.74-2.83 (m, 2H), 2.96-3.17 (m, 1H), 3.82 (br. s, 1H), 7.02 (dd, 1H), 7.42 (d, 1H), 8.00-8.16 (m, 1H).

Example 52A

Diastereomer 2

Yield: 0.193 g (8.0% of theory)

LC-MS (Method 2): $R_t$=0.99 min; m/z=409 (M+H)$^+$.

$^1$H-NMR (400 MHz, DMSO-d$_6$): δ [ppm]=1.22 (d, 3H), 1.35 (s, 9H), 2.48-2.52 (m, about 2H, obscured), 2.76-2.85 (m, 2H), 2.95-3.12 (m, 1H), 3.61 (br. s, 1H), 7.01 (dd, 1H), 7.41 (d, 1H), 8.05 (d, 1H).

Example 53A (+)-tert-Butyl 3-(4-chloro-3-{[(3R)-4,4,4-trifluoro-D-valyl]amino}phenyl)propanoate

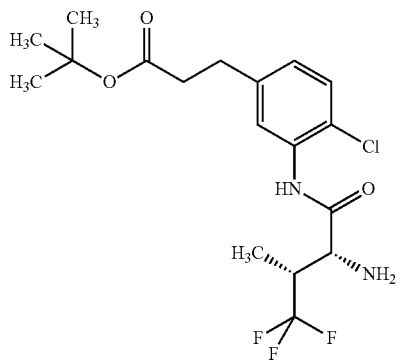 [SMILES: C[C@H]([C@@H](N)C(=O)Nc1cc(CCC(=O)OC(C)(C)C)ccc1Cl)C(F)(F)F]

1.17 g (2.16 mmol) of tert-butyl 3-[3-({(3R)—N-[(benzyloxy)carbonyl]-4,4,4-trifluorovalyl}amino)-4-chlorophenyl]propanoate (Example 35A, diastereomer mixture) were dissolved in 20 ml of ethyl acetate. The solution was inertized with argon, and 229 mg of palladium on carbon (5%) were added. The reaction mixture was stirred vigorously at standard pressure under an atmosphere of hydrogen for 8 h. After filtration through kieselguhr, the filtrate was concentrated under reduced pressure. The residue obtained was re-dissolved in 50 ml of ethyl acetate. After inertization of the solution with argon, another 230 mg of palladium on carbon (5%) were added, and the reaction mixture was stirred vigorously under standard hydrogen pressure for a further 4 h.

After filtration through kieselguhr, the filtrate was concentrated under reduced pressure and the residue was re-dissolved in 20 ml of THF. After inertization of the solution with argon, another 230 mg of palladium on carbon (5%) were added, and the reaction mixture was stirred vigorously under standard hydrogen pressure for a further 3 h. Following filtration through kieselguhr, the filtrate was concentrated under reduced pressure and the residue obtained was purified by chromatography on silica gel (mobile phase cyclohexane/ethyl acetate 40:1→5:1) and separated into the diastereomers. This gave 197 mg of the title compound (22.4% of theory).

LC-MS (Method 2): $R_t$=1.08 min; m/z=409 (M+H)$^+$.

$^1$H-NMR (400 MHz, DMSO-$d_6$): δ [ppm]=1.04 (d, 3H), 1.35 (s, 9H), 2.48-2.52 (m, about 2H, obscured), 2.76-2.84 (m, 2H), 3.02-3.12 (m, 1H), 3.80-3.86 (m, 1H), 7.02 (dd, 1H), 7.42 (d, 1H), 8.10-8.14 (m, 1H).

$[α]_D^{20}$=+15.6°, c=0.625, chloroform.

Example 54A

Ethyl (2S)-3-{4-fluoro-3-[(4,4,4-trifluorovalyl)amino]phenyl}-2-methylpropanoate (diastereomer mixture 1)

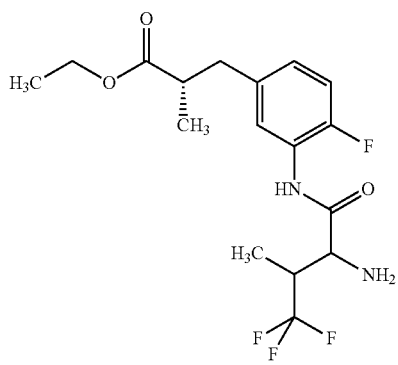 [SMILES: CCOC(=O)[C@@H](C)Cc1ccc(F)c(NC(=O)C(N)C(C)C(F)(F)F)c1]

2.60 g (5.07 mmol) of ethyl (2S)-3-[3-({N-[(benzyloxy)carbonyl]-4,4,4-trifluorovalyl}amino)-4-fluorophenyl]-2-methylpropanoate (Example 36A, mixture of 4 isomers) were dissolved in a mixture of 10.7 ml of ethanol and 10.7 ml of THF. The solution was inertized with argon, and 322 mg of palladium on carbon (10%) were added. The reaction mixture was stirred vigorously at standard pressure under an atmosphere of hydrogen overnight. After filtration through kieselguhr and washing with dichloromethane/methanol, the filtrate was concentrated under reduced pressure. The residue was purified by chromatography on silica gel (mobile phase cyclohexane/ethyl acetate 10:1→4:1) and separated. This gave 1.39 g of the title compound as diastereomer mixture 1 (72.4% of theory).

LC-MS (Method 5): $R_t$=1.60 min; m/z=379 (M+H)$^+$.

$^1$H-NMR (400 MHz, DMSO-$d_6$): δ [ppm]=1.01-1.15 (m, 9H), 2.62-2.72 (m, 2H), 2.78-2.88 (m, 1H), 2.90-3.06 (m, 1H), 3.81 (br. s, 1H), 4.01 (q, 2H), 6.90-7.00 (m, 1H), 7.18 (dd, 1H), 7.88 (d, 1H).

Example 55A (+)-Ethyl (2S)-3-(4-fluoro-3-{[(3R)-4,4,4-trifluoro-D-valyl]amino}phenyl)-2-methylpropanoate

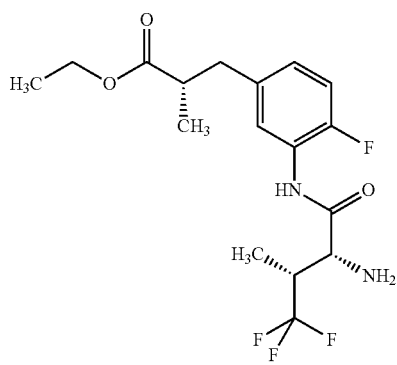 [SMILES: CCOC(=O)[C@@H](C)Cc1ccc(F)c(NC(=O)[C@H](N)[C@@H](C)C(F)(F)F)c1]

Process A:

The diastereomer mixture 1, obtained above, of ethyl (2S)-3-{4-fluoro-3-[(4,4,4-trifluorovalyl)amino]phenyl}-2-methylpropanoate (Example 54A) was separated further by preparative HPLC on a chiral phase [column: Daicel Chiralpak AD-H, 5 μm, 250 mm×20 mm; injection volume: 0.25 ml; temperature: 45° C.; mobile phase: 30% isohexane/70% ethanol (+0.2% diethylamine); flow rate: 15 ml/min; detection: 220 nm]. 1.39 g of diastereomer mixture gave 0.626 g of the title compound (as enantiomer 2).

LC-MS (Method 5): $R_t$=1.58 min; m/z=379 (M+H)$^+$.

$^1$H-NMR (400 MHz, DMSO-$d_6$): δ [ppm]=1.02-1.15 (m, 9H), 2.62-2.72 (m, 2H), 2.76-2.88 (m, 1H), 2.91-3.06 (m, 1H), 3.81 (br. s, 1H), 3.97-4.04 (m, 2H), 6.88-7.00 (m, 1H), 7.18 (dd, 1H), 7.88 (dd, 1H).

$[α]_D^{20}$=+54.1°, c=0.530, chloroform.

Process B:

1.274 g (2.49 mmol) of ethyl (2S)-3-[3-({(3R)—N-[(benzyloxy)carbonyl]-4,4,4-trifluorovalyl}amino)-4-fluorophenyl]-2-methylpropanoate (Example 43A, diastereomer mixture) were dissolved in a mixture of 10 ml of ethanol and 10 ml of THF. The solution was inertized with argon, and 132 mg of palladium on carbon (10%) were added. The reaction mixture was stirred vigorously at standard pressure under an atmosphere of hydrogen overnight. After filtration through kieselguhr and washing with dichloromethane/methanol, the filtrate was concentrated under reduced pressure. The residue was purified by chromatography on silica gel (mobile phase cyclohexane/ethyl acetate 5:1→2:1) and separated. This gave 713 mg of the title compound (75.9% of theory).

LC-MS (Method 3): $R_t$=0.93 min; m/z=379 (M+H)$^+$.

$^1$H-NMR (400 MHz, DMSO-$d_6$): δ [ppm]=1.02-1.14 (m, 9H), 2.63-2.72 (m, 2H), 2.78-2.88 (m, 1H), 2.91-3.07 (m, 1H), 3.81 (br. s, 1H), 3.94-4.05 (m, 2H), 6.91-6.99 (m, 1H), 7.18 (dd, 1H), 7.89 (dd, 1H).

$[α]_D^{20}$=+48.1°, c=0.525, chloroform.

Example 56A

Ethyl (2R)-3-{4-fluoro-3-[(4,4,4-trifluorovalyl)amino]phenyl}-2-methylpropanoate (diastereomer mixture 1)

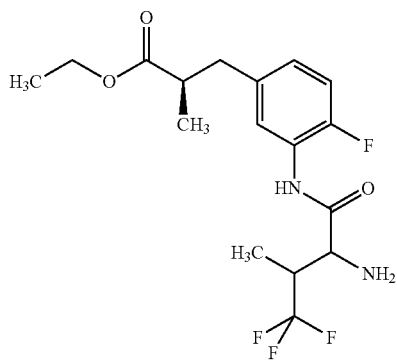 [SMILES: CCOC(=O)[C@H](C)Cc1ccc(F)c(NC(=O)C(N)C(C)C(F)(F)F)c1]

2.36 g (4.61 mmol) of ethyl (2R)-3-[3-({N-[(benzyloxy)carbonyl]-4,4,4-trifluorovalyl}amino)-4-fluorophenyl]-2-methylpropanoate (Example 37A, mixture of 4 isomers) were dissolved in a mixture of 9.8 ml of ethanol and 9.8 ml of THF. The solution was inertized with argon, and 293 mg of palladium on carbon (10%) were added. The reaction mixture was stirred vigorously at standard pressure under an atmosphere of hydrogen overnight. Following filtration through kieselguhr and washing with dichloromethane/methanol, the filtrate was concentrated under reduced pressure and the residue was purified by chromatography on silica gel (mobile phase cyclohexane/ethyl acetate 10:1→4:1) and separated. This gave 1.35 g of the target compound as diastereomer mixture 1 (77.2% of theory).

LC-MS (Method 5): $R_t$=1.54 min; m/z=379 (M+H)$^+$.

$^1$H-NMR (400 MHz, DMSO-d$_6$): δ [ppm]=1.05 (d, 3H), 1.07 (d, 3H), 1.11 (t, 3H), 2.61-2.72 (m, 2H), 2.77-2.88 (m, 1H), 2.91-3.06 (m, 1H), 3.81 (br. s, 1H), 4.01 (q, 2H), 6.92-7.00 (m, 1H), 7.18 (dd, 1H), 7.88 (d, 1H).

Example 57A (+)-Ethyl (2R)-3-(4-fluoro-3-{[(3R)-4,4,4-trifluoro-d-valyl]amino}phenyl)-2-methylpropanoate

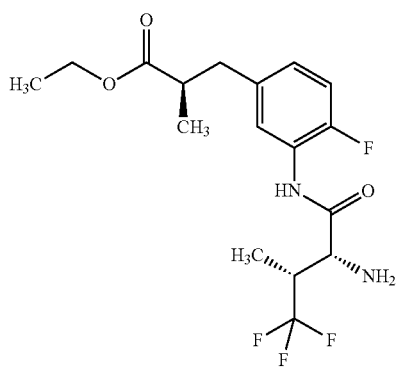

The diastereomer mixture 1, obtained above, of ethyl (2R)-3-{4-fluoro-3-[(4,4,4-trifluorovalyl)amino]phenyl}-2-methylpropanoate (Example 56A) was separated further by preparative HPLC on a chiral phase [column: Daicel Chiralpak AD-H, 5 μm, 250 mm×20 mm; injection volume: 0.4 ml; temperature: 45° C.; mobile phase: 80% isohexane/20% ethanol (+0.2% diethylamine); flow rate: 15 ml/min; detection: 220 nm]. 1.35 g of diastereomer mixture gave 0.635 g of the title compound (as diastereomer 2).

LC-MS (Method 2): $R_t$=0.85 min; m/z=379 (M+H)$^+$.

$^1$H-NMR (400 MHz, DMSO-d$_6$): δ [ppm]=1.05 (d, 3H), 1.07 (d, 3H), 1.11 (t, 3H), 2.64-2.70 (m, 2H), 2.77-2.88 (m, 1H), 2.91-3.04 (m, 1H), 3.81 (br. s, 1H), 4.01 (q, 2H), 6.89-6.99 (m, 1H), 7.18 (dd, 1H), 7.88 (dd, 1H).

$[α]_D^{20}$=+2.0°, c=0.640, chloroform.

Example 58A

Ethyl (2R)-3-{4-chloro-3-[(4,4,4-trifluorovalyl)amino]phenyl}-2-methylpropanoate (diastereomer mixture 1)

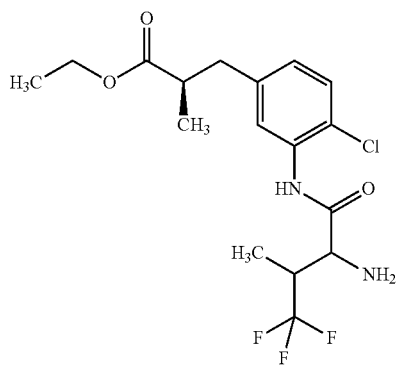 [SMILES: CCOC(=O)[C@H](C)Cc1ccc(Cl)c(NC(=O)C(N)C(C)C(F)(F)F)c1]

1.40 g (2.92 mmol) of ethyl (2R)-3-[3-({N-[(allyloxy)carbonyl]-4,4,4-trifluorovalyl}amino)-4-chlorophenyl]-2-methylpropanoate (Example 38A, mixture of 4 isomers) and 3.28 g (23.4 mmol) of dimedone were initially charged in 10 ml of abs. THF. At RT, the solution was deoxygenated by passing through argon for 30 min. Subsequently 67.6 mg (0.058 mmol) of tetrakis(triphenylphosphine)palladium(0) were added and the mixture was stirred at RT overnight. After dilution with ethyl acetate, the mixture was washed twice with sat. sodium bicarbonate solution and once with sat. sodium chloride solution. The organic phase was dried over magnesium sulphate and concentrated under reduced pressure. The residue was purified by chromatography on silica gel (mobile phase cyclohexane/ethyl acetate 40:1→20:1) and separated. This gave 844 mg of the target compound as diastereomer mixture 1 (73.1% of theory).

LC-MS (Method 2): $R_t$=0.99 min; m/z=395 (M+H)$^+$.

¹H-NMR (400 MHz, DMSO-d₆): δ [ppm]=1.00-1.15 (m, 9H), 2.62-2.75 (m, 2H), 2.79-2.90 (m, 1H), 2.99-3.13 (m, 1H), 3.83 (br. s, 1H), 4.01 (q, 2H), 6.98 (dd, 1H), 7.42 (d, 1H), 8.07 (t, 1H).

Example 59A

Ethyl (2R)-3-(4-chloro-3-{[(3R)-4,4,4-trifluoro-D-valyl]amino}phenyl)-2-methylpropanoate

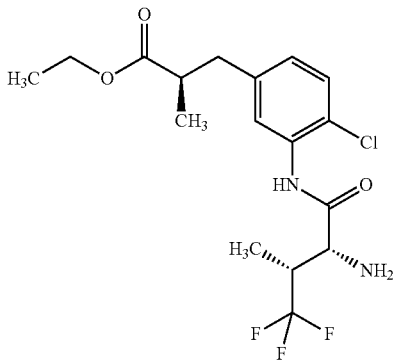 [SMILES: CCOC(=O)[C@H](C)Cc1ccc(Cl)c(NC(=O)[C@H](N)[C@@H](C)C(F)(F)F)c1]

The diastereomer mixture 1, obtained above, of ethyl (2R)-3-{4-chloro-3-[(4,4,4-trifluorovalyl)amino]phenyl}-2-methylpropanoate (Example 58A) was separated further by preparative HPLC on a chiral phase [column: Daicel Chiralpak AD-H, 5 μm, 250 mm×20 mm; injection volume: 0.40 ml; temperature: 45° C.; mobile phase: 80% isohexane/20% ethanol (+2% diethylamine); flow rate: 15 ml/min; detection: 220 nm]. 840 mg of diastereomer mixture gave 382 mg of the title compound (as diastereomer 2).

LC-MS (Method 3): $R_t$=1.05 min; m/z=395 (M+H)⁺.

¹H-NMR (400 MHz, DMSO-d₆): δ [ppm]=1.05 (d, 3H), 1.07 (d, 3H), 1.11 (t, 3H), 2.62-2.75 (m, 2H), 2.80-2.90 (m, 1H), 3.01-3.13 (m, 1H), 3.83 (br. s, 1H), 4.01 (q, 2H), 6.98 (dd, 1H), 7.42 (d, 1H), 8.07 (d, 1H).

$[\alpha]_D^{20}$=5.9°, c=0.500, chloroform.

Example 60A

Ethyl (2S)-3-{4-chloro-3-[(4,4,4-trifluorovalyl)amino]phenyl}-2-methylpropanoate (diastereomer mixture 1)

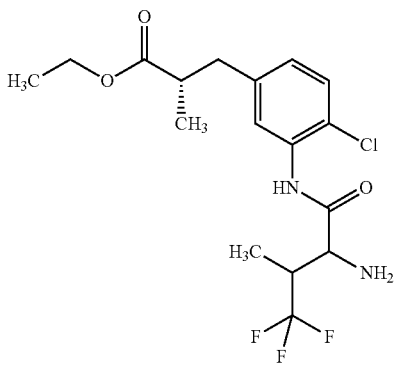 [SMILES: CCOC(=O)[C@@H](C)Cc1ccc(Cl)c(NC(=O)C(N)C(C)C(F)(F)F)c1]

2.24 g (4.68 mmol) of ethyl (2S)-3-[3-({N-[(allyloxy)carbonyl]-4,4,4-trifluorovalyl}amino)-4-chlorophenyl]-2-methylpropanoate (Example 39A, mixture of 4 isomers) and 5.25 g (37.4 mmol) of dimedone were initially charged in 25 ml of abs. THF. At RT, the solution was deoxygenated by passing through argon for 30 min Subsequently 108.1 mg (0.094 mmol) of tetrakis(triphenylphosphine)palladium(0) were added and the mixture was stirred at RT overnight. After dilution with ethyl acetate, the mixture was washed twice with sat. sodium bicarbonate solution and once with sat. sodium chloride solution. The organic phase was dried over magnesium sulphate and concentrated under reduced pressure. The residue was purified by chromatography on silica gel (mobile phase cyclohexane/ethyl acetate 40:1→20:1) and separated. This gave 1.65 g of the target compound as diastereomer mixture 1 (89.4% of theory).

LC-MS (Method 2): $R_t$=0.99 min; m/z=395 (M+H)⁺.

¹H-NMR (400 MHz, DMSO-d₆): δ [ppm]=1.05 (d, 3H), 1.07 (d, 3H), 1.11 (t, 3H), 2.64-2.75 (m, 2H), 2.80-2.90 (m, 1H), 3.02-3.12 (m, 1H), 3.83 (br. s, 1H), 4.01 (q, 2H), 6.98 (dd, 1H), 7.42 (d, 1H), 8.07 (d, 1H).

Example 61A (+)-Ethyl (2S)-3-(4-chloro-3-{[(3R)-4,4,4-trifluoro-D-valyl]amino}phenyl)-2-methylpropanoate

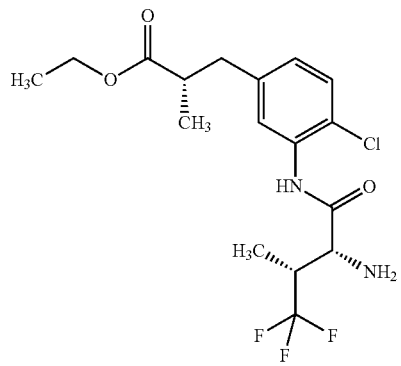 [SMILES: CCOC(=O)[C@@H](C)Cc1ccc(Cl)c(NC(=O)[C@H](N)[C@@H](C)C(F)(F)F)c1]

Process A:

The diastereomer mixture 1, obtained above, of ethyl (2S)-3-{4-chloro-3-[(4,4,4-trifluorovalyl)amino]phenyl}-2-methylpropanoate (Example 60A) was separated further by preparative HPLC on a chiral phase [column: Daicel Chiralpak AD-H, 5 μm, 250 mm×20 mm; injection volume: 0.25 ml; temperature: 45° C.; mobile phase: 80% isohexane/20% ethanol (+0.2% diethylamine); flow rate: 15 ml/min; detection: 220 nm]. 1.65 g of diastereomer mixture gave 0.78 g of the target compound.

LC-MS (Method 2): $R_t$=0.99 min; m/z=395 (M+H)⁺.

¹H-NMR (400 MHz, DMSO-d₆): δ [ppm]=1.04 (d, 3H), 1.08 (d, 3H), 1.10 (t, 3H), 2.64-2.74 (m, 2H), 2.80-2.88 (m, 1H), 3.01-3.12 (m, 1H), 3.83 (br. s, 1H), 3.97-4.05 (m, 2H), 6.98 (dd, 1H), 7.42 (d, 1H), 8.07 (d, 1H).

$[\alpha]_D^{20}$=+40.4°, c=0.565, chloroform.

Process B:

0.99 g (1.87 mmol) of ethyl (2S)-3-[3-({(3R)—N-[(benzyloxy)carbonyl]-4,4,4-trifluorovalyl}amino)-4-chlorophenyl]-2-methylpropanoate (Example 44A, diastereomer mixture) were dissolved in 50 ml of ethyl acetate. The solution was inertized with argon, and 40 mg of palladium on carbon (5%) were added. The reaction mixture was stirred vigorously at standard pressure under an atmosphere of hydrogen for 4 h. Following filtration through kieselguhr, the filtrate was concentrated under reduced pressure and the residue was purified by chromatography on silica gel (mobile phase cyclohexane/ethyl acetate 20:1→5:1) and separated. This gave 444 mg of the title compound (60.1% of theory).

LC-MS (Method 2): $R_t$=0.95 min; m/z=395 (M+H)$^+$.

$^1$H-NMR (400 MHz, DMSO-d$_6$): δ [ppm]=1.04 (d, 3H), 1.08 (d, 3H), 1.10 (t, 3H), 2.62-2.74 (m, 2H), 2.79-2.89 (m, 1H), 3.03-3.12 (m, 1H), 3.83 (br. s, 1H), 3.97-4.08 (m, 2H), 6.98 (dd, 1H), 7.42 (d, 1H), 8.08 (d, 1H).

$[α]_D^{20}$=+34.1°, c=0.525, chloroform.

Example 62A tert-Butyl (3R)-3-{4-chloro-3-[(4,4,4-trifluorovalyl)amino]phenyl}butanoate (diastereomer mixture 1)

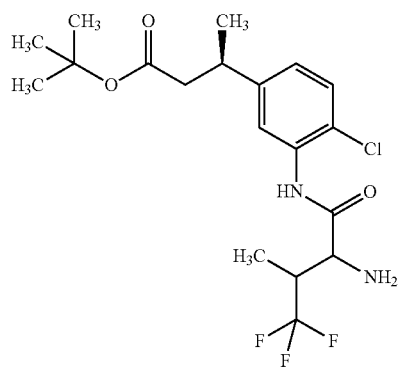 [SMILES: CC(C(N)C(=O)Nc1cc([C@H](C)CC(=O)OC(C)(C)C)ccc1Cl)C(F)(F)F]

630 mg (1.24 mmol) of tert-butyl (3R)-3-[3-({N-[(allyloxy)carbonyl]-4,4,4-trifluorovalyl}amino)-4-chlorophenyl]butanoate (Example 40A, mixture of 4 isomers) and 1.394 g (9.94 mmol) of dimedone were initially charged in 10 ml of abs. THF. At RT, the solution was deoxygenated by passing through argon for 30 min. Subsequently 28.7 mg (0.025 mmol) of tetrakis(triphenylphosphine)palladium(0) were added and the mixture was stirred at RT overnight. After dilution with ethyl acetate, the mixture was washed twice with sat. sodium bicarbonate solution and once with sat. sodium chloride solution. The organic phase was dried over magnesium sulphate and concentrated under reduced pressure. The residue was purified by chromatography on silica gel (mobile phase cyclohexane/ethyl acetate 40:1→20:1) and separated. This gave 420 mg of the target compound as diastereomer mixture 1 (79.9% of theory).

LC-MS (Method 2): $R_t$=1.14 min; m/z=423 (M+H)$^+$.

$^1$H-NMR (400 MHz, DMSO-d$_6$): both diastereomers δ [ppm]=1.04/1.05 (in each case d, tog. 3H), 1.19/1.20 (in each case d, tog. 3H), 1.29 (s, 9H), 2.35-2.48 (m, 2H), 2.97-3.16 (m, 2H), 3.83 (br. s, 1H), 7.06 (dt, 1H), 7.43 (dd, 1H), 8.16 (d, 1H).

Example 63A tert-Butyl (3S)-3-{4-chloro-3-[(4,4,4-trifluorovalyl)amino]phenyl}butanoate (diastereomer mixture 1)

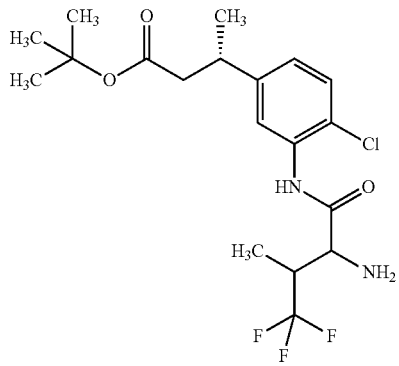 [SMILES: CC(C(N)C(=O)Nc1cc([C@@H](C)CC(=O)OC(C)(C)C)ccc1Cl)C(F)(F)F]

1.39 g (2.74 mmol) of tert-butyl (3S)-3-[3-({N-[(allyloxy)carbonyl]-4,4,4-trifluorovalyl}amino)-4-chlorophenyl]butanoate (Example 41A, mixture of 4 isomers) and 3.08 g (21.9 mmol) of dimedone were initially charged in 9.4 ml of abs. THF. At RT, the solution was deoxygenated by passing through argon for 30 min. Subsequently 63.4 mg (0.055 mmol) of tetrakis(triphenylphosphine)palladium(0) were added and the mixture was stirred at RT overnight. After dilution with ethyl acetate, the mixture was washed twice with sat. sodium bicarbonate solution and once with sat. sodium chloride solution. The organic phase was dried over magnesium sulphate and concentrated under reduced pressure. The residue was purified by chromatography on silica gel (mobile phase cyclohexane/ethyl acetate 40:1→20:1) and separated. This gave 950 mg of the target compound as diastereomer mixture 1 (81.9% of theory).

LC-MS (Method 2): $R_t$=1.15 min; m/z=423 (M+H)$^+$.

$^1$H-NMR (400 MHz, DMSO-d$_6$): both diastereomers δ [ppm]=1.04/1.05 (in each case d, tog. 3H), 1.19/1.20 (in each case d, tog. 3H), 1.29 (s, 9H), 2.29-2.48 (m, 2H), 2.99-3.16 (m, 2H), 3.83 (br. s, 1H), 7.06 (dt, 1H), 7.43 (dd, 1H), 8.16 (d, 1H).

Example 64A tert-Butyl (3S)-3-(4-chloro-3-{[(3R)-4,4,4-trifluoro-D-valyl]amino}phenyl)butanoate

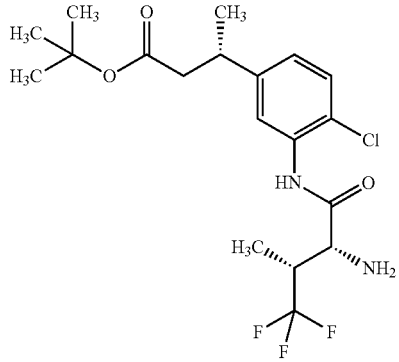

1.30 g (2.56 mmol) of tert-butyl (3S)-3-[3-({(3R)—N-[(allyloxy)carbonyl]-4,4,4-trifluorovalyl}amino)-4-chlorophenyl]butanoate (Example 42A, diastereomer mixture) and 2.88 g (20.5 mmol) of dimedone were initially charged in 8.7 ml of abs. THF. At RT, the solution was deoxygenated by passing through argon for 30 min. Subsequently 59.3 mg (0.051 mmol) of tetrakis(triphenylphosphine)palladium(0) were added and the mixture was stirred at RT overnight. After dilution with ethyl acetate, the mixture was washed twice with sat. sodium bicarbonate solution and once with sat. sodium chloride solution. The organic phase was dried over magnesium sulphate and concentrated under reduced pressure. The residue was purified by chromatography on silica gel (mobile phase cyclohexane/ethyl acetate 10:1) and separated. This gave 591 mg of the target compound (54.5% of theory).

LC-MS (Method 2): $R_t$=1.14 min; m/z=423 (M+H)$^+$.

$^1$H-NMR (400 MHz, DMSO-d$_6$): δ [ppm]=1.05 (d, 3H), 1.19 (d, 3H), 1.29 (s, 9H), 2.38-2.48 (m, 2H), 3.02-3.16 (m, 2H), 3.83 (d, 1H), 7.06 (dd, 1H), 7.43 (d, 1H), 8.16 (d, 1H).

Example 65A (+)-tert-Butyl 1-(4-chloro-3-{[(3R)-4,4,4-trifluoro-D-valyl]amino}benzyl)cyclopropanecarboxylate

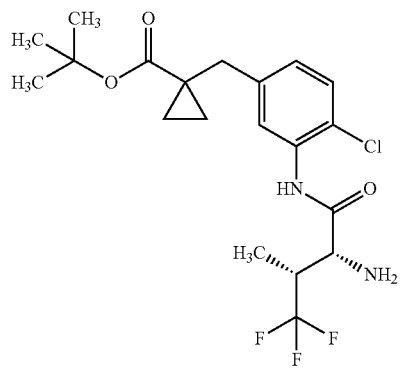 [SMILES: C[C@H]([C@@H](N)C(=O)Nc1cc(CC2(C(=O)OC(C)(C)C)CC2)ccc1Cl)C(F)(F)F]

450 mg (0.867 mmol) of tert-butyl 1-[3-({(3R)—N-[(allyloxy)carbonyl]-4,4,4-trifluorovalyl}amino)-4-chlorobenzyl] cyclopropanecarboxylate (Example 45A, diastereomer mixture) and 972.4 mg (6.94 mmol) of dimedone were initially charged in 3 ml of abs. THF. At RT, the solution was deoxygenated by passing through argon for 30 min. Subsequently 20.0 mg (0.017 mmol) of tetrakis(triphenylphosphine)palladium(0) were added and the mixture was stirred at RT overnight. After dilution with ethyl acetate, the mixture was washed twice with sat. sodium bicarbonate solution and once with sat. sodium chloride solution. The organic phase was dried over magnesium sulphate and concentrated under reduced pressure. The residue was purified by chromatography on silica gel (mobile phase cyclohexane/ethyl acetate 20:1) and separated. This gave 221.4 mg of the target compound (58.7% of theory).

LC-MS (Method 2): $R_t$=1.15 min; m/z=435 (M+H)$^+$.

$^1$H-NMR (400 MHz, DMSO-d$_6$): δ [ppm]=0.82-0.87 (m, 2H), 1.04 (d, 3H), 1.06-1.10 (m, 2H), 1.29 (s, 9H), 2.77-2.90 (m, 2H), 3.02-3.12 (m, 1H), 3.83 (br. s, 1H), 7.04 (dd, 1H), 7.42 (d, 1H), 8.12-8.23 (m, 1H).

$[α]_D^{20}$=+16.1°, c=0.425, chloroform.

Example 66A 3-(Trifluoromethyl)pentane-1,5-diol

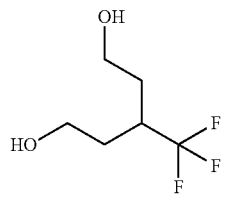 [SMILES: OCCC(CCO)C(F)(F)F]

12.0 g (59.97 mmol) of 3-(trifluoromethyl)pentanedioic acid were dissolved in 70 ml of abs. THF, and, after cooling to −10° C., 120 ml (120 mmol) of a 1 M solution of lithium aluminium hydride in THF were added dropwise. After the addition had ended, the reaction mixture was warmed to RT overnight. After cooling to 0° C., initially about 10 ml of isopropanol and then 20 ml of an isopropanol/water mixture (3:1) were carefully added dropwise. The resulting suspension was acidified by addition of 1 N hydrochloric acid and mixed with Celite. The mixture was filtered and the filtrate obtained was concentrated under reduced pressure. To remove residual water, acetonitrile was added to the oil obtained and the mixture was once more concentrated under reduced pressure. The crude product was purified by chromatography on silica gel (mobile phase cyclohexane/ethyl acetate 4:1→1:1). This gave 4.5 g of the target product (43.6% of theory).

GC-MS (Method 1): $R_t$=2.76 min; m/z=153 (M−H$_3$O)$^+$.

$^1$H-NMR (400 MHz, DMSO-d$_6$): δ [ppm]=1.49-1.57 (m, 2H), 1.67-1.75 (m, 2H), 2.30-2.48 (m, 1H), 3.47 (q, 4H), 4.61 (t, 2H).

Example 67A

3-Phenylpentane-1,5-diol

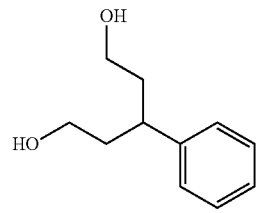 [SMILES: OCCC(CCO)c1ccccc1]

3.0 g (14.4 mmol) of 3-phenylglutaric acid were dissolved in 20 ml of abs. THF, the mixture was cooled to −10° C. and 31.7 ml (31.7 mmol) of a 1 M solution of lithium aluminium hydride in THF were added dropwise. During the addition, a further 50 ml of abs. THF were added. The resulting suspension was slowly warmed to RT and stirred at RT overnight. After cooling to 0° C., initially isopropanol and then a mixture of isopropanol and water (3:1) were carefully added dropwise. The resulting suspension was acidified by addition of 1 N hydrochloric acid and mixed with Celite. The mixture was filtered through Celite, the filter cake was washed with isopropanol and the filtrate obtained was concentrated under reduced pressure. The crude product was purified by chromatography on silica gel (mobile phase cyclohexane/ethyl acetate 2:1→1:1). This gave 1.9 g of the target product (73% of theory).

GC-MS (Method 1): $R_t$=5.53 min; m/z=163 (M-OH)$^+$.

$^1$H-NMR (400 MHz, DMSO-$d_6$): δ [ppm]=1.56-1.71 (m, 2H), 1.72-1.83 (m, 2H), 2.68-2.86 (m, 1H), 3.12-3.29 (m, 4H), 4.32 (t, 2H), 7.10-7.21 (m, 3H), 7.23-7.32 (m, 2H).

Further 3-substituted pentane-1,5-diols not commercially available can be prepared, for example, analogously to the following three-step sequence 68A-69A-70A:

Example 68A

Ethyl 3-cyclopropylacrylate

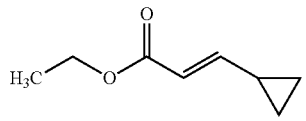

At 0° C., 13.0 ml (64.85 mmol) of ethyl diethylphosphonoacetate were added dropwise to a suspension of 2.59 g (64.85 mmol) of sodium hydride (60% in mineral oil) in 110 ml of abs. THF. After 30 min, the mixture was warmed to RT and, after cooling again to 0° C., 5.3 ml (71.34 mmol) of cyclopropanecarboxaldehyde were added dropwise. After the end of the addition, the reaction mixture was warmed to RT and diluted with 35 ml of DMF. The mixture was stirred at RT overnight and then added to water. The mixture was extracted three times with ethyl acetate. The combined organic phases were concentrated under reduced pressure and the crude product was purified by filtration through silica gel (mobile phase cyclohexane/ethyl acetate 10:1→6:1). This gave 8.53 g of the target product (93.8% of theory).

GC-MS (Method 1): $R_t$=2.83 min; m/z=112 (M-C$_2$H$_4$)$^+$.

$^1$H-NMR (400 MHz, DMSO-$d_6$): δ [ppm]=0.59-0.70 (m, 2H), 0.88-0.95 (m, 2H), 1.19 (t, 3H), 1.54-1.72 (m, 1H), 4.08 (q, 2H), 5.93 (d, 1H), 6.39 (dd, 1H).

Example 69A

Diethyl 3-cyclopropylpentanedioate

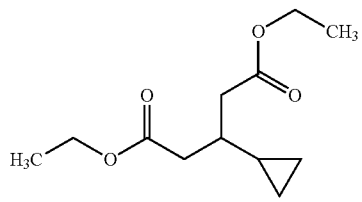 [SMILES: CCOC(=O)CC(CC(=O)OCC)C1CC1]

29.1 ml (72.8 mmol) of a 2.5 M solution of n-butyllithium in hexane were added dropwise to a solution, cooled to −40° C., of 10.2 ml (72.8 mmol) of diisopropylamine in 35 ml of abs. THF. After the end of the addition, the mixture was stirred at −40° C. for another 30 min and then cooled to −78° C., and a solution of 7.1 ml (72.8 mmol) of ethyl acetate in 10 ml of abs. THF was added dropwise. The reaction mixture was stirred at −78° C. for 30 min, and a solution of 8.50 g (60.54 mmol) of ethyl 3-cyclopropylacrylate in a little THF was then added dropwise. After 1 h at −78° C., the mixture was slowly warmed to −40° C., then to 0° C., and a saturated aqueous ammonium chloride solution was finally added. After extraction with ethyl acetate, the organic phase was washed with 1 N hydrochloric acid and sat. sodium chloride solution, dried over sodium sulphate and concentrated under reduced pressure. The crude product was purified by chromatography on silica gel (mobile phase cyclohexane/ethyl acetate 30:1→6:1). This gave 3.28 g of the target product (23.7% of theory).

GC-MS (Method 1): $R_t$=4.56 min; m/z=183 (M-C$_2$H$_5$O)$^+$.

$^1$H-NMR (400 MHz, DMSO-$d_6$): δ [ppm]=0.07-0.13 (m, 2H), 0.32-0.41 (m, 2H), 0.62-0.75 (m, 1H), 1.15-1.22 (m, 6H), 1.41-1.52 (m, 1H), 2.33-2.46 (m, 4H), 4.00-4.10 (m, 4H).

Example 70A

3-Cyclopropylpentane-1,5-diol

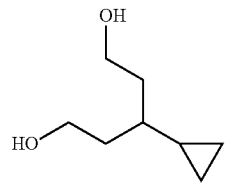

3.2 g (14.02 mmol) of diethyl 3-cyclopropylpentanedioate were dissolved in 24.7 ml of abs. THF, and, after cooling to −10° C., 25.2 ml (25.2 mmol) of a 1 M solution of lithium aluminium hydride in THF were added dropwise. The reaction mixture was stirred at RT overnight. After cooling to 0° C., 100 ml of isopropanol were carefully added dropwise. The mixture was acidified by addition of 1 N hydrochloric acid and mixed with Celite. After filtration through Celite and washing with ethyl acetate and water, the filtrate was saturated with sodium chloride and extracted three times with ethyl acetate. The combined organic phases were dried over magnesium sulphate and concentrated under reduced pressure. The crude product was purified by chromatography on silica gel (mobile phase cyclohexane/ethyl acetate 10:1→2:1). This gave 1.35 g of the target product (66.8% of theory).

GC-MS (Method 1): $R_t$=3.98 min; m/z=115 (M-C$_2$H$_5$)$^+$.

$^1$H-NMR (400 MHz, DMSO-$d_6$): δ [ppm]=0.01-0.07 (m, 2H), 0.32-0.40 (m, 2H), 0.41-0.52 (m, 1H), 0.69-0.82 (m, 1H), 1.49 (q, 4H), 3.41-3.54 (m, 4H), 4.24 (t, 2H).

Example 71A

3-Ethylpentane-1,5-diol

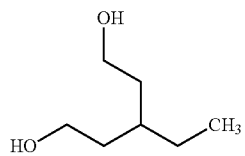

The title compound can be obtained analogously to the three-step process 68A-69A-70A described above.

GC-MS (Method 1): $R_t$=3.41 min; m/z=114 $(M-H_2O)^+$.

$^1$H-NMR (400 MHz, DMSO-$d_6$): δ [ppm]=0.81 (t, 3H), 1.16-1.31 (m, 2H), 1.31-1.52 (m, 5H), 3.34-3.48 (m, 4H), 4.29 (t, 2H).

General Procedure 2: Oxidation of 3-Substituted Pentane-1,5-Diols to Dialdehydes (or their Cyclic Acetals)

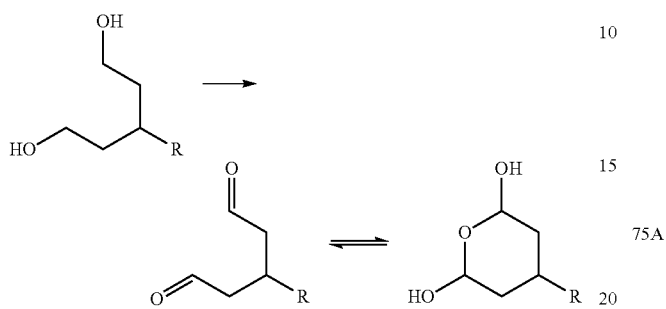

2.6 eq. of oxalyl chloride are dissolved in abs. dichloromethane (1.0 to 2.5 mol/l) and cooled to about −50° C., and a solution of 5 eq. of DMSO in abs. dichloromethane (about 5 mol/l) is added dropwise. After 10 min at about −50° C., a solution of the diol in question (1.0 eq.) in abs. dichloromethane (0.5 to 1.0 mol/l) is added dropwise. After a further 10 min, the reaction mixture is cooled to −78° C., and a mixture of triethylamine (about 10.5 eq.) and abs. dichloromethane (ratio by volume 1:1 to 1:2) is added dropwise. After the end of the addition, the reaction mixture is stirred at about −78° C. for another 30 min and then warmed slowly (to about −20° C., 0° C. or RT), diluted with dichloromethane, washed with sat. sodium bicarbonate solution, dried over sodium sulphate and concentrated under reduced pressure. The crude product obtained is not purified any further but can be employed directly for subsequent reactions.

The examples below were prepared in accordance with the General Procedure 2 and used without further purification (in general, the dialdehydes could be stored as crude product at −20° C. under argon):

| Example | Name/Structure/Starting material | Analytical data |
|---|---|---|
| 72A | 3-methylpentanedial<br>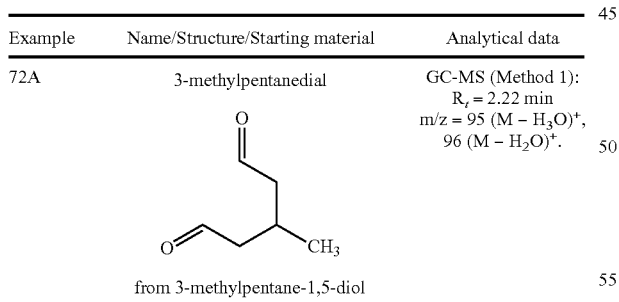<br>from 3-methylpentane-1,5-diol | GC-MS (Method 1):<br>$R_t$ = 2.22 min<br>m/z = 95 $(M - H_3O)^+$,<br>96 $(M - H_2O)^+$. |
| 73A | 3-ethylpentanedial<br>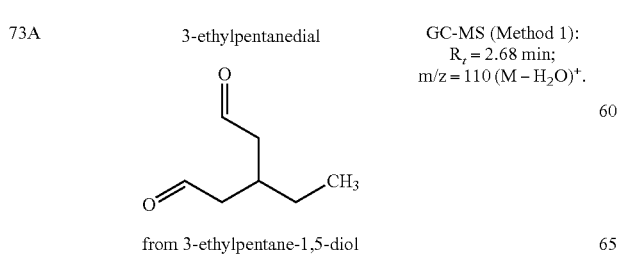<br>from 3-ethylpentane-1,5-diol | GC-MS (Method 1):<br>$R_t$ = 2.68 min;<br>m/z = 110 $(M - H_2O)^+$. |
| 74A | 3-(trifluoromethyl)pentanedial<br><br>from 3-(trifluoromethyl)pentane-1,5-diol | GC-MS (Method 1):<br>$R_t$ = 1.82 min;<br>m/z = 148 $(M - HF)^+$. |
| 75A | 3-cyclopropylpentanedial<br><br>from 3-cyclopropylpentane-1,5-diol | GC-MS (Method 1):<br>$R_t$ = 3.26 min;<br>m/z = 122 $(M - H_2O)^+$. |
| 76A | 3-phenylpentanedial<br><br>from 3-phenylpentane-1,5-diol | GC-MS (Method 1):<br>$R_t$ = 5.04 min<br>m/z = 176 $(M)^+$,<br>158 $(M - H_2O)^+$. |

Example 77A

Methyl Cyclopropylideneacetate

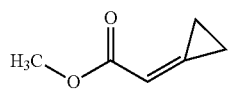

A suspension of 240 g (1.38 mol) of [(1-ethoxycyclopropyl)oxy](trimethyl)silane, 598 g (1.79 mol) of (methoxycarbonylmethylene)triphenylphosphorane and 21.9 g (0.179 mol) of benzoic acid in 3.94 liters of toluene was stirred at 85° C. overnight. After cooling, the reaction mixture was purified directly by chromatography on 4.8 kg of silica gel (mobile phase: petroleum ether/dichloromethane mixture from 1:1 to pure dichloromethane). The product fractions were combined and concentrated under slightly reduced pressure. This gave 159 g of the target product as a clear colourless oil (crude product still contained residual solvent).

GC-MS (Method 1): $R_t$=1.84 min; m/z=112 (M+H)$^+$.

$^1$H-NMR (400 MHz, DMSO-d$_6$): δ [ppm]=1.24-1.31 (m, 2H), 1.38-1.46 (m, 2H), 3.66 (s, 3H), 6.23-6.36 (m, about 1H).

Example 78A

Ethyl methyl 2,2'-cyclopropane-1,1-diyldiacetate

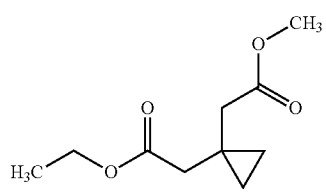

240 ml (1.70 mol) of diisopropylamine were dissolved in 700 ml of abs. THF, the mixture was cooled to −40° C. and 681 ml (1.7 mol) of a 2.5 M solution of n-butyllithium in hexane were added slowly. The solution was stirred at −40° C. for 30 min and then cooled to −78° C., and a solution of 166.6 ml (1.7 mol) of ethyl acetate p.a. in 200 ml of abs. THF was added. After the end of the addition, the mixture was stirred at −78° C. for another 30 min 159 g (crude product, about 1.42 mol) of methyl cyclopropylideneacetate, dissolved in a little abs. THF, were then added dropwise. The reaction mixture was stirred at −78° C. for 1 h and then, via −40° C., slowly warmed to about 0° C., and a saturated aqueous ammonium chloride solution was finally added. The mixture was extracted with ethyl acetate and the organic phase was washed with 1 N hydrochloric acid and sat. sodium chloride solution, dried over sodium sulphate and concentrated under reduced pressure. The residue was purified chromatographically on silica gel (mobile phase cyclohexane/ethyl acetate 9:1). This gave 109.5 g of the target compound which was contaminated by the diethyl ester derivative and was not purified any further.

GC-MS (Method 1): $R_t$=3.82 min; m/z=168 (M-CH$_4$O)$^+$.

Example 79A 2,2'-Cyclopropane-1,1-diyldiethanol

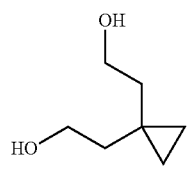

109.5 g (crude product, about 547 mmol) of ethyl methyl 2,2'-cyclopropane-1,1-diyldiacetate were dissolved in 750 ml of p.a. THF, and, at −20° C., 984 ml (984 mmol) of a 1 M solution of lithium aluminium hydride in THF were added dropwise. The reaction mixture was warmed to RT overnight and, after cooling again to −10° C., 500 ml of isopropanol were added carefully. The mixture was acidified with 1 N hydrochloric acid and filtered off with suction through Celite. The residue was washed with ethyl acetate and water. The filtrate was saturated with sodium chloride and extracted repeatedly with ethyl acetate. The combined organic phases were dried over sodium sulphate and concentrated under reduced pressure. The residue was recrystallized from acetonitrile. This gave 50.4 g of the target product (70.8% of theory).

GC-MS (Method 1): $R_t$=3.48 min; m/z=112 (M-H$_2$O)$^+$.

$^1$H-NMR (400 MHz, DMSO-d$_6$): δ [ppm]=0.21 (s, 4H), 1.37 (t, 4H), 3.46 (q, 4H), 4.28 (t, 2H).

Example 80A 2,2'-Cyclopropane-1,1-diyldiacetaldehyde

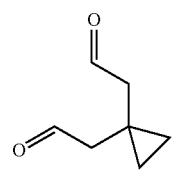

7.0 ml (79.9 mmol) of oxalyl chloride were dissolved in 45 ml of abs. dichloromethane, the mixture was cooled to −50° C. and a solution of 10.9 ml (163.6 mmol) of DMSO in 45 ml of abs. dichloromethane was added dropwise. After the end of the addition, the mixture was stirred at −50° C. for another 10 min, and 4.0 g (30.7 mmol) of 2,2'-cyclopropane-1,1-diyldiethanol, dissolved in 45 ml of abs. dichloromethane, were then added slowly. The resulting suspension was stirred at −50° C. for 10 min and then cooled to −78° C., and a solution of 44.5 ml (320 mmol) of triethylamine in 75 ml of abs. dichloromethane was added dropwise. After the end of the addition, the reaction mixture was stirred at −78° C. for 30 min and then slowly warmed to RT and subsequently washed with saturated aqueous sodium bisulphate solution. The organic phase was dried over sodium sulphate and concentrated under reduced pressure. This gave 5.10 g of the target product as an orange oil (crude product of a purity of about 70%, about 92% of theory).

GC-MS (Method 1): $R_t$=2.72 min; m/z=108 (M-H$_2$O)$^+$, 107 (M-H$_3$O)$^+$.

Example 81A tert-Butyl 3-(4-chloro-3-{[4,4,4-trifluoro-3-methyl-2-(4-methylpiperidin-1-yl)butanoyl]amino}phenyl)propanoate (racemic diastereomer mixture)

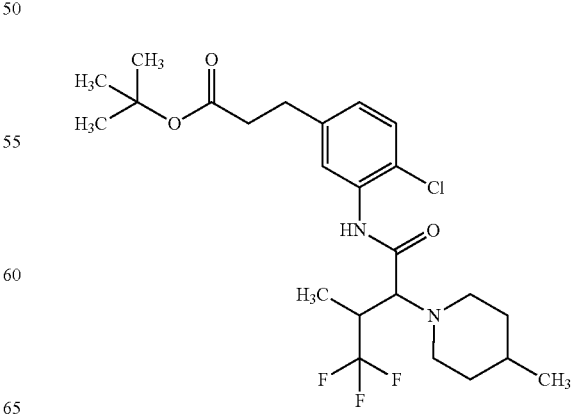

Step 1:

705 mg (2.89 mmol) of 1,5-dibromo-3-methylpentane and 7.2 ml of 1 N aqueous sodium hydroxide solution were added to 300 mg (1.45 mmol) of (+/−)-D,L-4,4,4-trifluorovaline hydrochloride in 6 ml of ethanol, and the mixture was stirred under reflux overnight. After addition of a further 1.0 eq. of 1,5-dibromo-3-methylpentane and 5.0 eq. of sodium hydroxide, the mixture was once more stirred under reflux for 8 h and then, after cooling, concentrated under reduced pressure. The residue was taken up in a little water and neutralized with 1 N hydrochloric acid. The aqueous phase was extracted repeatedly with ethyl acetate. The combined organic phases were dried over sodium sulphate and concentrated under reduced pressure. This gave, as crude product, 270 mg of 4,4,4-trifluoro-3-methyl-2-(4-methylpiperidin-1-yl)butanoic acid (racemic diastereomer mixture).

Step 2:

270 mg of 4,4,4-trifluoro-3-methyl-2-(4-methylpiperidin-1-yl)butanoic acid (crude product, racemic diastereomer mixture) were dissolved in 2.5 ml of pyridine and 4.9 ml of DMF, and 286 mg (1.12 mmol) of tert-butyl 3-(3-amino-4-chlorophenyl)propanoate and 527 mg (1.37 mmol) of HATU were added at RT. The mixture was stirred at 40° C. overnight. A further 0.5 eq. of HATU and 2 ml of N,N-diisopropylethylamine were added, and the reaction mixture was once more stirred at 50° C. for 5 h and then added to water. The mixture was extracted three times with ethyl acetate and the combined organic phases were washed with a little 1 N hydrochloric acid, dried over magnesium sulphate and concentrated under reduced pressure. The crude product was purified by preparative RP-HPLC (mobile phase acetonitrile/water). This gave 50 mg of the target product (9.6% of theory) as a diastereomer mixture (about 3:2).

LC-MS (Method 2): $R_t$=1.53 min and 1.57 min; in each case m/z=491 (M+H)$^+$.

$^1$H-NMR (400 MHz, DMSO-d$_6$): both diastereomers δ [ppm]=0.86/0.87 (in each case d, tog. 3H), 0.96-1.05 (m, 1H), 1.07/1.10 (in each case d, tog. 3H), 1.12-1.24 (m, 1H), 1.24-1.34 (m, 1H), 1.35/1.36 (in each case s, tog. 9H), 1.51-1.65 (m, 2H), 2.00-2.17 (m, 1H), 2.43-2.48 (m, 1H), 2.64 (d, 1H), 2.76-2.83 (m, 2H), 2.84-3.10 (m, 3H), 3.52/3.59 (in each case d, tog. 1H), 7.04-7.12 (m, 1H), 7.41 (dd, 1H), 7.47/7.55 (in each case d, tog. 1H), 9.58/9.68 (in each case s, tog. 1H).

General Procedure 3: Preparation of Substituted Piperidinoacetanilides from Aminoacetanilides According to the Reaction Scheme Below:

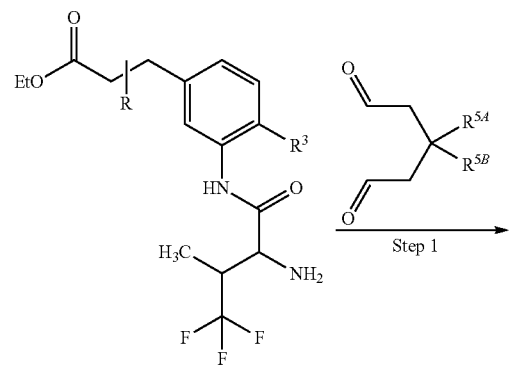

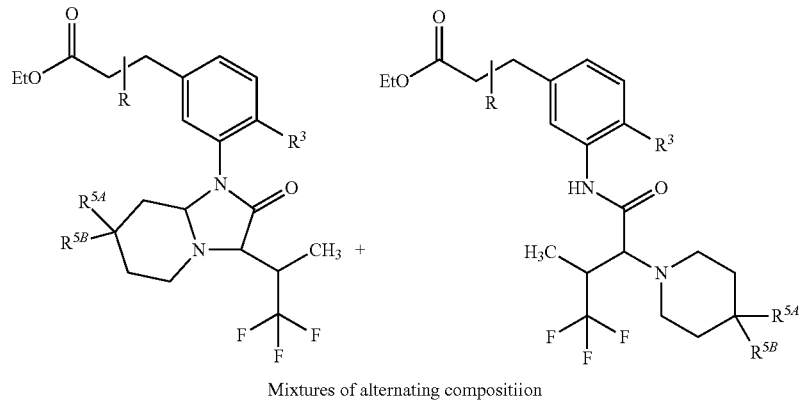

Mixtures of alternating compositiion

Step 2

-continued

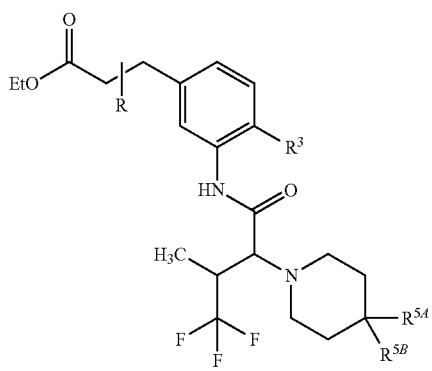

Step 1:

At RT, triethylamine (1.5 to 2.0 eq.), 1 N hydrochloric acid (about 0.25 to 0.5 eq.), the dialdehyde in question (or its cyclic acetal form, as a crude mixture, about 2.0 to 4.0 eq.) and, after about 5 to 15 min, sodium cyanoborohydride (2.0 bis 4.0 eq.) are added to a solution of the aminoacetanilide component in question (1.0 eq.) in methanol (about 0.05 mol/l to 1 mol/l). The mixture is stirred at RT for about 12 to 72 hours, and during this time further quantities of triethylamine, 1 N hydrochloric acid, dialdehyde and/or sodium cyanoborohydride are added if required. After the reaction has ended, the reaction mixture is added to water. The aqueous phase is extracted three times with ethyl acetate, and the combined organic phases are concentrated under reduced pressure. The crude product mixture obtained can be employed directly in the next step or is (preferably) purified beforehand by preparative RP-HPLC (mobile phase acetonitrile/water gradient).

Step 2:

At 0° C. or RT, the respective intermediate mixture from step 1 (crude or purified) is dissolved in trifluoroacetic acid (concentration about 0.1 to 2.0 mol/l) and a large excess of triethylsilane (6 to 15 eq.) is then added dropwise at 0° C. to RT. The mixture is stirred at RT for 4 to 24 h; if required, the mixture is heated at 40° C. until complete conversion is achieved. The reaction mixture is then concentrated under reduced pressure. The residue is taken up in ethyl acetate and washed with water and sodium bicarbonate solution until about neutral (pH 6-7). After concentration under reduced pressure, the crude product can be purified by preparative RP-HPLC (mobile phase acetonitrile/water or methanol/water), by chromatography on silica gel (mobile phase cyclohexane/ethyl acetate or dichloromethane/methanol mixtures) or by a combination of these methods, or it is directly reacted further without purification.

The following examples were prepared according to General Procedure 3:

| Example | Name/Structure/Starting materials | Analytical data |
| --- | --- | --- |
| 82A | ethyl (2S)-3-(3-{[2-(6-azaspiro[2.5]oct-6-yl)-4,4,4-trifluoro-3-methylbutanoyl]amino}-4-chlorophenyl)-2-methylpropanoate (diastereomer mixture 1)<br><br>from ethyl (2S)-3-{4-chloro-3-[(4,4,4-trifluorovalyl)amino]phenyl}-2-methylpropanoate (diastereomer mixture 1) and 2,2'-cyclopropane-1,1-diyldiacetaldehyde | LC-MS (Method 5): $R_t$ = 3.02 min; m/z = 489 (M + H)$^+$.<br>$^1$H-NMR (400 MHz, DMSO-$d_6$): δ [ppm] = 0.21 (s, 4H), 1.06-1.15 (m, 9H), 1.32 (br. s, 4H), 2.60-2.76 (m, 4H), 2.53-2.58 (m, about 2H), 2.78-2.88 (m, 1H), 3.07 (dd, 1H), 3.56 (d, 1H), 4.01 (q, 2H), 7.04 (dt, 1H) 7.41 (d, 1H), 7.44 (t, 1H), 9.60 (s, 1H). |

-continued

| Example | Name/Structure/Starting materials | Analytical data |
|---|---|---|
| 83A | ethyl (2S)-3-(4-chloro-3-{[(2R,3R)-4,4,4-trifluoro-3-methyl-2-(4-methylpiperidin-1-yl)butanoyl]amino}phenyl)-2-methylpropanoate<br><br>*[chemical structure]*<br><br>from (+)-ethyl (2S)-3-(4-chloro-3-{[(3R)-4,4,4-trifluoro-D-valyl]amino}phenyl)-2-methylpropanoate and 3-methylpentanedial | LC-MS (Method 2): $R_t$ = 1.48 min; m/z = 477 (M + H)$^+$.<br>$^1$H-NMR (400 MHz, DMSO-$d_6$): δ [ppm] = 0.87-0.95 (m, about 3H), 1.01-1.31 (m, about 13H), 1.53-1.63 (m, 2H), 2.05 (t, 1H), 2.59-2.76 (m, 3H), 2.76-2.96 (m, 2H), 2.99-3.07 (m, 1H), 3.51 (d, 1H), 3.95-4.05 (m, 2H), 7.03 (dd, 1H), 7.37-7.44 (m, 2H), 9.60 (s, 1H). |
| 84A | Ethyl (2S)-3-(3-{[(2R,3R)-2-(6-azaspiro[2.5]oct-6-yl)-4,4,4-trifluoro-3-methylbutanoyl]amino}-4-fluorophenyl)-2-methylpropanoate<br><br>*[chemical structure]*<br><br>from (+)-ethyl (2S)-3-(4-fluoro-3-{[(3R)-4,4,4-trifluoro-D-valyl]amino}phenyl)-2-methylpropanoate and 2,2'-cyclopropane-1,1-diyldiacetaldehyde | LC-MS (Method 2): $R_t$ = 1.42 min; m/z = 473 (M + H)$^+$.<br>$^1$H-NMR (400 MHz, DMSO-$d_6$): δ [ppm] = 0.16-0.23 (m, 4H), 1.05-1.16 (m, 9H), 1.29 (br. s, 4H), 2.52-2.61 (m, about 4H), 2.61-2.74 (m, 2H), 2.75-2.86 (m, 1H), 3.05 (dd, 1H), 3.55 (d, 1H), 3.95-4.04 (m, 2H), 6.94-7.02 (m, 1H), 7.16 (dd, 1H), 7.63 (dd, 1H), 9.73 (s, 1H). |
| 85A | ethyl (2R)-3-(4-fluoro-3-{[(2R,3R)-4,4,4-trifluoro-3-methyl-2-(4-methylpiperidin-1-yl)butanoyl]amino}phenyl)-2-methylpropanoate<br><br>*[chemical structure]*<br><br>from (+)-ethyl (2R)-3-(4-fluoro-3-{[(3R)-4,4,4-trifluoro-D-valyl]amino}phenyl)-2-methylpropanoate and 3-methylpentanedial | LC-MS (Method 5): $R_t$ = 2.76 min; m/z = 461 (M + H)$^+$.<br>$^1$H-NMR (400 MHz, DMSO-$d_6$): δ [ppm] = 0.86 (d, 3H), 0.96-1.05 (m, 1H), 1.05-1.13 (m, 9H), 1.13-1.36 (m, 2H), 1.57 (t, 2H), 1.96-2.07 (m, 1H), 2.35-2.45 (m, 1H), 2.59-2.73 (m, 3H), 2.76-2.83 (m, 1H), 2.89 (d, 1H), 2.97-3.08 (m, 1H), 3.49 (d, 1H), 3.96-4.04 (m, 2H), 6.88-7.03 (m, 1H), 7.15 (dd, 1H), 7.57 (dd, 1H), 9.71 (s, 1H). |

-continued

| Example | Name/Structure/Starting materials | Analytical data |
| --- | --- | --- |
| 86A | ethyl (2R)-3-(3-{[(2R,3R)-2-(6-azaspiro[2.5]oct-6-yl)-4,4,4-trifluoro-3-methylbutanoyl]amino}-4-chlorophenyl)-2-methylpropanoate<br><br>from (−)-ethyl (2R)-3-(4-chloro-3-{[(3R)-4,4,4-trifluoro-D-valyl]amino}phenyl)-2-methylpropanoate and 2,2′-cyclopropane-1,1-diyldiacetaldehyde | LC-MS (Method 2): $R_t$ = 1.47 min; m/z = 489 (M + H)$^+$.<br>$^1$H-NMR (400 MHz, DMSO-$d_6$): δ [ppm] = 0.21 (br. s, 4H), 1.06-1.16 (m, 9H), 1.23-1.42 (m, 4H), 2.50-2.58 (m, about 2H, obscured), 2.61-2.75 (m, 4H), 2.78-2.88 (m, 1H), 3.02-3.12 (m, 1H), 3.56 (d, 1H), 4.01 (q, 2H), 7.04 (dd, 1H), 7.35-7.47 (m, 2H), 9.61 (s, 1H). |
| 87A | ethyl (2S)-3-(4-fluoro-3-{[(2R,3R)-4,4,4-trifluoro-3-methyl-2-(4-methylpiperidin-1-yl)butanoyl]amino}phenyl)-2-methylpropanoate<br><br>from (+)-ethyl (2S)-3-(4-fluoro-3-{[(3R)-4,4,4-trifluoro-D-valyl]amino}phenyl)-2-methylpropanoate and 3-methylpentanedial | LC-MS (Method 2): $R_t$ = 1.39 min; m/z = 461 (M + H)$^+$.<br>$^1$H-NMR (400 MHz, DMSO-$d_6$): δ [ppm] = 0.87 (d, 3H), 0.97-1.05 (m, 1H), 1.05-1.13 (m, 9H), 1.13-1.35 (m, 2H), 1.57 (t, 2H), 2.02 (t, 1H), 2.39 (t, 1H), 2.59-2.73 (m, 3H), 2.75-2.93 (m, 2H), 2.95-3.10 (m, 1H), 3.49 (d, 1H), 3.93-4.06 (m, 2H), 6.98 (td, 1H), 7.15 (dd, 1H), 7.58 (dd, 1H), 9.70 (s, 1H). |
| 88A | ethyl (2R)-3-(4-chloro-3-{[(2R,3R)-4,4,4-trifluoro-3-methyl-2-(4-methylpiperidin-1-yl)butanoyl]amino}phenyl)-2-methylpropanoate<br><br>from (−)-ethyl (2R)-3-(4-chloro-3-{[(3R)-4,4,4-trifluoro-D-valyl]amino}phenyl)-2-methylpropanoate and 3-methylpentanedial | LC-MS (Method 2): $R_t$ = 1.48 min; m/z = 477 (M + H)$^+$.<br>$^1$H-NMR (400 MHz, DMSO-$d_6$): δ [ppm] = 0.87 (d, 3H), 0.97-1.05 (m, 1H), 1.08-1.13 (m, 9H), 1.14-1.35 (m, 2H), 1.51-1.68 (m, 2H), 2.05 (t, 1H), 2.50-2.57 (m, about 1H, obscured), 2.60-2.74 (m, 3H), 2.77-2.96 (m, 2H), 2.98-3.07 (m, 1H), 3.51 (d, 1H), 4.01 (q, 2H), 7.03 (dd, 1H), 7.34-7.52 (m, 2H), 9.60 (s, 1H). |

| Example | Name/Structure/Starting materials | Analytical data |
|---|---|---|
| 89A | ethyl (2R)-3-(3-{[(2R,3R)-2-(6-azaspiro[2.5]oct-6-yl)-4,4,4-trifluoro-3-methylbutanoyl]amino}-4-fluorophenyl)-2-methylpropanoate<br><br>from (+)-ethyl (2R)-3-(4-fluoro-3-{[(3R)-4,4,4-trifluoro-D-valyl]amino}phenyl)-2-methylpropanoate and 2,2'-cyclopropane-1,1-diyldiacetaldehyde | LC-MS (Method 2): $R_t$ = 1.40 min; m/z = 473 (M + H)$^+$.<br>$^1$H-NMR (400 MHz, DMSO-$d_6$): δ [ppm] = 0.20 (br. s, 4H), 1.03-1.17 (m, 9H), 1.30 (br. s, 4H), 2.52-2.62 (m, about 4H, obscured), 2.63-2.74 (m, 2H), 2.77-2.87 (m, 1H), 3.00-3.10 (m, 1H), 3.54 (d, 1H), 4.01 (q, 2H), 6.99 (td, 1H), 7.16 (dd, 1H), 7.61 (dd, 1H), 9.72 (s, 1H).<br>$[α]_D^{20}$ = +5.0°, c = 0.450, chloroform. |
| 90A | ethyl (2S)-3-[4-chloro-3-({(2R,3R)-4,4,4-trifluoro-3-methyl-2-[4-(trifluoromethyl)piperidin-1-yl]butanoyl}amino)phenyl]-2-methylpropanoate<br><br>from (+)-ethyl (2S)-3-(4-chloro-3-{[(3R)-4,4,4-trifluoro-D-valyl]amino}phenyl)-2-methylpropanoate and 3-(trifluoromethyl)pentanedial | LC-MS (Method 3): $R_t$ = 1.62 min; m/z = 531 (M + H)$^+$.<br>$^1$H-NMR (400 MHz, DMSO-$d_6$): δ [ppm] = 1.04-1.15 (m, 9H), 1.30-1.40 (m, 1H), 1.44-1.58 (m, 1H), 1.72-1.87 (m, 2H), 2.11 (t, 1H), 2.20-2.30 (m, 1H), 2.55-2.64 (m, 1H), 2.65-2.74 (m, 2H), 2.75-2.89 (m, 2H), 3.06 (d, 2H), 3.57 (d, 1H), 4.01 (q, 2H), 7.04 (dd, 1H), 7.37-7.46 (m, 2H), 9.67 (s, 1H). |

Example 91A rac-Cyclopent-1-en-1-yl(4-methoxypiperidin-1-yl)acetic acid

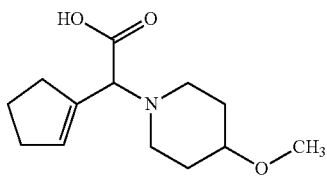 [SMILES: COC1CCN(C(C(=O)O)C2=CCCC2)CC1]

50 mg (0.45 mmol) of cyclopent-1-en-1-ylboronic acid, 51 mg (0.45 mmol) of 4-methoxypiperidine and 41 mg (0.45 mmol) of glyoxalic acid monohydrate were initially charged in 2 ml of dichloromethane, and 78 µl (57 mg, 0.45 mmol) of N,N-diisopropylethylamine were added. The mixture was stirred at RT for 2 d and then concentrated under reduced pressure. The residue was purified by preparative HPLC (RP18 column; acetonitrile/water gradient with addition of 0.1% TFA, 10:90→95:5; run time 38 min). This gave 31 mg (29% of theory) of the title compound.

LC-MS (Method 5): $R_t$=0.95 min; m/z=240 (M+H)$^+$.

Example 92A rac-Cyclopent-1-en-1-yl(3,4-dihydroisoquinolin-2(1H)-yl)acetic acid

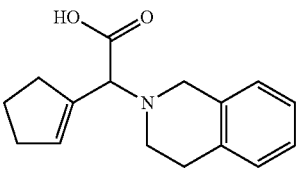 [SMILES: O=C(O)C(C1=CCCC1)N1CCc2ccccc2C1]

50 mg (0.45 mmol) of cyclopent-1-en-1-ylboronic acid, 59.5 mg (0.45 mmol) of 1,2,3,4-tetrahydroisoquinoline and 41 mg (0.45 mmol) of glyoxalic acid monohydrate were initially charged in 2 ml of dichloromethane, and 78 μl (57 mg, 0.45 mmol) of N,N-diisopropylethylamine were added. The mixture was stirred at RT for overnight and then concentrated under reduced pressure. The residue was purified by preparative HPLC (RP18 column; acetonitrile/water gradient with addition of 0.1% TFA, 10:90→95:5; run time 38 min) 101 mg (91% purity, 80% of theory) of the title compound were obtained.

LC-MS (Method 5): $R_t$=1.22 min; m/z=258 (M+H)$^+$.

Example 93A rac-tert-Butyl 1-(3-{[cyclopent-1-en-1-yl(4-methoxypiperidin-1-yl)acetyl]amino}-4-fluorobenzyl)cyclopropanecarboxylate

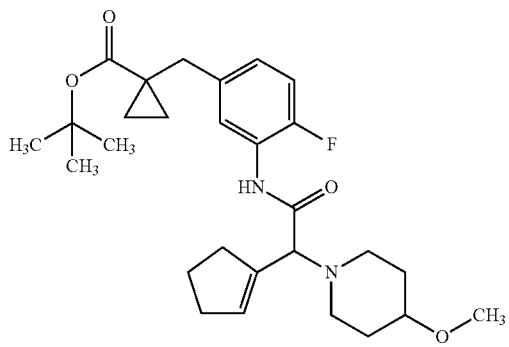 [SMILES: COC1CCN(C(C(=O)Nc2cc(CC3(C(=O)OC(C)(C)C)CC3)ccc2F)C2=CCCC2)CC1]

30.9 mg (0.13 mmol) of rac-cyclopent-1-en-1-yl(4-methoxypiperidin-1-yl)acetic acid were initially charged in 0.87 ml of DMF/pyridine (3:1), 63.8 mg (0.17 mmol) of HATU were added and the mixture was stirred at RT for 30 min 34.3 mg (0.13 mmol) of tert-butyl 1-(3-amino-4-fluorobenzyl)cyclopropanecarboxylate were then added, and the reaction mixture was stirred at RT overnight. The mixture was then diluted with ethyl acetate, washed repeatedly with saturated sodium chloride solution, dried over magnesium sulphate and concentrated under reduced pressure. The residue was purified by preparative HPLC (RP18 column; acetonitrile/water gradient with addition of 0.1% TFA, 10:90→95:5; run time 38 min). This gave 20.7 mg (33% of theory) of the title compound.

LC-MS (Method 5): $R_t$=1.85 min; m/z=487.4 (M+H)$^+$.

Example 94A rac-tert-Butyl 1-(3-{[cyclopent-1-en-1-yl(3,4-dihydroisoquinolin-2(1H)-yl)acetyl]amino}-4-fluorobenzyl)cyclopropanecarboxylate

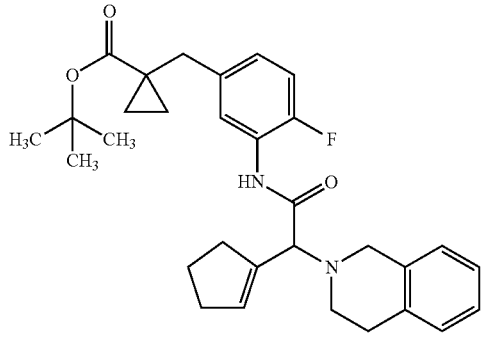 [SMILES: CC(C)(C)OC(=O)C1(Cc2ccc(F)c(NC(=O)C(C3=CCCC3)N3CCc4ccccc4C3)c2)CC1]

100 mg (0.39 mmol) of rac-cyclopent-1-en-1-yl(3,4-dihydroisoquinolin-2(1H)-yl)acetic acid were initially charged in 2.6 ml of DMF/pyridine (3:1), 192 mg (0.51 mmol) of HATU were added and the mixture was stirred at RT for 30 min. 103 mg (0.39 mmol) of tert-butyl 1-(3-amino-4-fluorobenzyl)cyclopropanecarboxylate were then added, and the reaction mixture was stirred at RT overnight. The mixture was then purified directly by preparative HPLC (RP18 column; acetonitrile/water gradient with addition of 0.1% TFA, 10:90→95:5; run time 38 min). The product obtained in this manner was taken up in ethyl acetate and washed repeatedly with 1 N hydrochloric acid. The organic phase was dried over magnesium sulphate and concentrated under reduced pressure. This gave 103 mg (purity 72%, 37% of theory) of the title compound which was reacted without further purification.

LC-MS (Method 5): $R_t$=2.26 min; m/z=505.3 (M+H)$^+$.

Example 95A rac-tert-Butyl 1-(3-{[cyclopentyl(4-methoxypiperidin-1-yl)acetyl]amino}-4-fluorobenzyl)cyclopropanecarboxylate

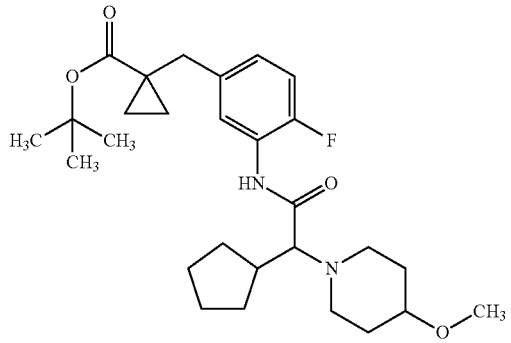 [SMILES: COC1CCN(C(C(=O)Nc2cc(CC3(C(=O)OC(C)(C)C)CC3)ccc2F)C2CCCC2)CC1]

20.7 mg (0.04 mmol) of rac-tert-Butyl 1-(3-{[cyclopent-1-en-1-yl(4-methoxypiperidin-1-yl)acetyl]amino}-4-fluorobenzyl)cyclopropanecarboxylate were initially charged in 3 ml of methanol, 3 mg (0.01 mmol) of platinum(IV) oxide were added and the mixture was hydrogenated at RT and standard pressure for 5 h. The mixture was then filtered through kieselguhr, the residue was washed thoroughly with methanol and the filtrate was concentrated under reduced pressure. 19.5 mg (100% purity, 94% of theory) of the title compound were obtained.

LC-MS (Method 5): $R_t$=1.92 min; m/z=489.4 (M+H)$^+$.

Example 96A rac-tert-Butyl 1-(3-{[cyclopentyl(3,4-dihydroisoquinolin-2(1H)-yl)acetyl]amino}-4-fluorobenzyl)cyclopropanecarboxylate

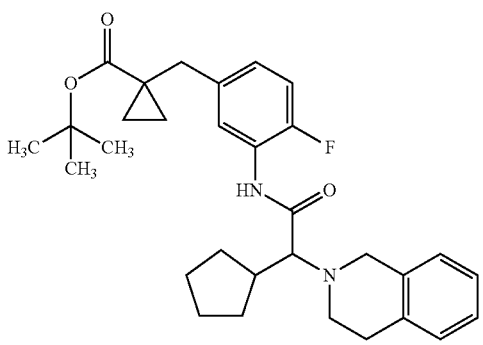 [SMILES: CC(C)(C)OC(=O)C1(Cc2ccc(F)c(NC(=O)C(C3CCCC3)N3CCc4ccccc4C3)c2)CC1]

102 mg (0.2 mmol, purity 72%) of rac-tert-butyl 1-(3-{[cyclopent-1-en-1-yl(3,4-dihydroisoquinolin-2(1H)-yl)acetyl]amino}-4-fluorobenzyl)cyclopropanecarboxylate were initially charged in 14.4 ml of methanol, 14.4 mg (0.06 mmol) of platinum(IV) oxide were added and the mixture was hydrogenated at RT and standard pressure for 5 h. The mixture was then filtered through kieselguhr, the residue was washed thoroughly with methanol and the filtrate was concentrated under reduced pressure. This gave 102 mg (purity 36%) of the title compound which was reacted further without purification.

LC-MS (Method 5): $R_t$=1.34 min; m/z=507.2 (M+H)$^+$.

Working Examples

Example 1

3-(4-Chloro-3-{[4,4,4-trifluoro-3-methyl-2-(4-methylpiperidin-1-yl)butanoyl]amino}phenyl)propanoic acid (racemic diastereomer mixture)

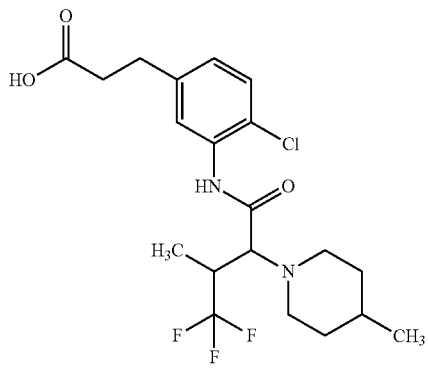 [SMILES: CC1CCN(C(C(=O)Nc2cc(CCC(=O)O)ccc2Cl)C(C)C(F)(F)F)CC1]

45.0 mg (0.092 mmol) of tert-butyl 3-(4-chloro-3-{[4,4,4-trifluoro-3-methyl-2-(4-methylpiperidin-1-yl)butanoyl]amino}phenyl)propanoate (racemic diastereomer mixture) were dissolved in 0.1 ml of dichloromethane, and 0.35 ml of trifluoroacetic acid was added at RT. The reaction mixture was stirred at RT overnight and then concentrated under reduced pressure. The crude product was purified by preparative RP-HPLC (mobile phase acetonitrile/water). This gave 39.0 mg of the target product as a diastereomer mixture (97.9% of theory).

LC-MS (Method 2): $R_t$=1.10 min and 1.21 min; in each case m/z=435 (M+H)$^+$.

$^1$H-NMR (400 MHz, DMSO-d$_6$): both diastereomers δ [ppm]=0.86/0.87 (in each case dd, tog. 3H), 0.94-1.05 (m, 1H), 1.07/1.10 (in each case dd, tog. 3H), 1.13-1.35 (m, 2H), 1.49-1.65 (m, 2H), 2.00-2.16 (m, 1H), 2.56-2.68 (m, about 1H), 2.77-2.99 (m, about 5H), 3.51/3.59 (in each case d, tog. 1H), 7.05-7.15 (m, 1H), 7.40/7.42 (in each case d, tog. 1H), 7.45/7.54 (in each case d, tog. 1H), 9.61/9.71 (in each case s, tog. 1H), 12.16 (s, 1H).

General Procedure 4: Preparation of Substituted Piperidinoacetanilides from Aminoacetanilides According to the Reaction Scheme Below:

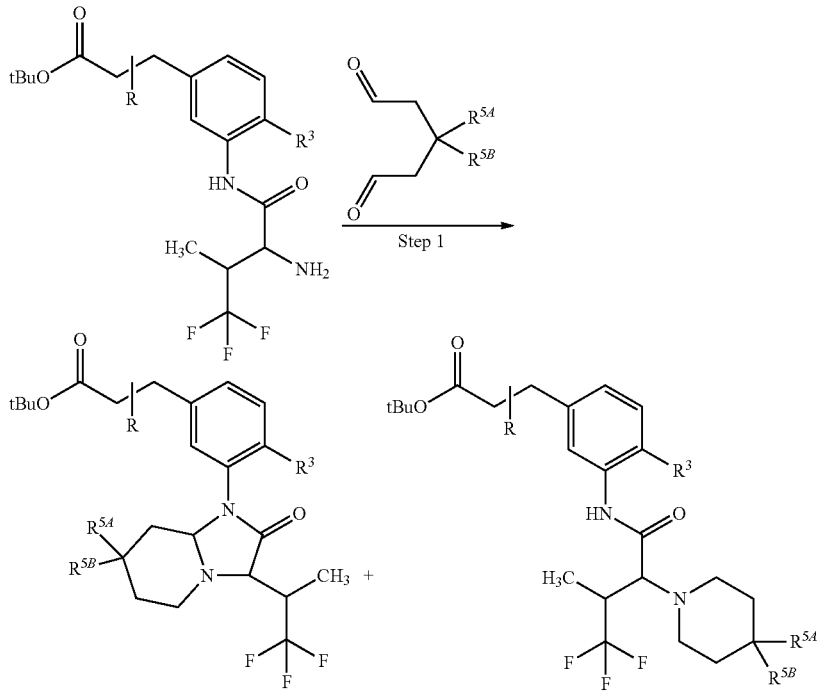

Mixtures of alternating compositiion

Step 2

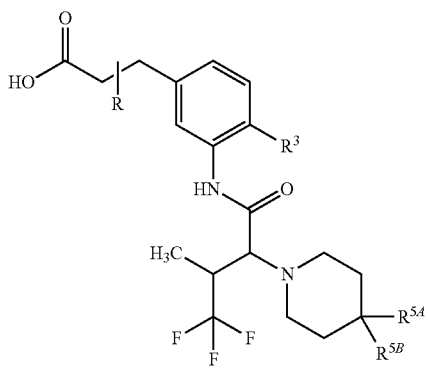

Step 1:

At RT, triethylamine (1.5 to 2.0 eq.), 1 N hydrochloric acid (about 0.25 to 0.5 eq.), the dialdehyde in question (or its cyclic acetal form, as a crude mixture, about 2.0 to 4.0 eq.) and, after about 5 to 15 min, sodium cyanoborohydride (2.0 bis 4.0 eq.) are added to a solution of the aminoacetanilide component in question (1.0 eq.) in methanol (about 0.05 mol/l to 1 mol/l). The mixture is stirred at RT for about 12 to 72 hours, and during this time further quantities of triethylamine, 1 N hydrochloric acid, dialdehyde and/or sodium cyanoborohydride are added if required. After the reaction has ended, the reaction mixture is added to water. The aqueous phase is extracted three times with ethyl acetate, and the combined organic phases are concentrated under reduced pressure. The crude product mixture obtained can be employed directly in the next step or is (preferably) purified beforehand by preparative RP-HPLC (mobile phase acetonitrile/water gradient).

Step 2:

At 0° C. or RT, the respective intermediate mixture from step 1 (crude or purified) is dissolved in trifluoroacetic acid (concentration about 0.1 to 2.0 mol/l) and a large excess of triethylsilane (10 to 20 eq.) is then added dropwise at 0° C. to RT. The mixture is stirred at RT for 4 to 24 h; if required, the mixture is heated at 40° C. until complete conversion is achieved. The reaction mixture is then concentrated under reduced pressure. The residue is taken up in ethyl acetate and washed with water (adjusted to almost neutral (pH 6-7) by addition of a little sat. sodium bicarbonate solution). After concentration under reduced pressure, the crude product can be purified by preparative RP-HPLC (mobile phase acetonitrile/water or methanol/water gradient), by crystallization from acetonitrile or water/acetonitrile mixtures or by a combination of these methods.

The following examples were prepared according to General Procedure 4:

| Example | Name/Structure/Starting materials | Analytical data |
|---|---|---|
| 2 | (+/−)-1-(4-fluoro-3-{[4,4,4-trifluoro-3-methyl-2-(piperidin-1-yl)butanoyl]amino}benzyl)cyclopropanecarboxylic acid (diastereomer 1)<br><br>from (+/−)-tert-butyl-1-{4-fluoro-3-[(4,4,4-trifluorovalyl)amino]benzyl}cyclopropanecarboxylate (diastereomer 1) and glutardialdehyde (as a 50% strength solution in water) | LC-MS (Method 2): $R_t$ = 1.07 min; m/z = 431 (M + H)$^+$.<br>$^1$H-NMR (400 MHz, DMSO-$d_6$): δ [ppm] = 0.77-0.85 (m, 2H), 1.06-1.15 (m, 5H), 1.37 (d, 2H), 1.41-1.59 (m, 4H), 2.40-2.55 (m, about 4H, obscured), 2.84 (s, 2H), 2.98-3.08 (m, 1H), 3.45 (d, 1H), 7.00-7.09 (m, 1H), 7.10-7.20 (m, 1H), 7.63 (dd, 1H), 9.70 (s, 1H), 12.16 (br. s, 1H). |

| Example | Name/Structure/Starting materials | Analytical data |
|---|---|---|
| 3 | (+/-)-1-(4-fluoro-3-{[4,4,4-trifluoro-3-methyl-2-(piperidin-1-yl)butanoyl]amino}benzyl)cyclopropanecarboxylic acid (diastereomer 2)<br><br>from (+/-)-tert-butyl-1-{4-fluoro-3-[(4,4,4-trifluorovalyl)amino]benzyl}cyclopropanecarboxylate (diastereomer 2) and glutardialdehyde (as a 50% strength solution in water) | LC-MS (Method 2): $R_t$ = 0.95 min; m/z = 431 (M + H)$^+$.<br>$^1$H-NMR (400 MHz, DMSO-$d_6$): δ [ppm] = 0.79-0.86 (m, 2H), 1.02 (d, 3H), 1.09-1.14 (m, 2H), 1.31-1.52 (m, 6H), 2.40-2.48 (m, 2H), 2.56-2.66 (m, 2H), 2.85 (s, 2H), 2.95 (dd, 1H), 3.55 (d, 1H), 7.05-7.21 (m, 2H), 7.64 (d, 1H), 9.76 (s, 1H), 12.16 (s, 1H). |
| 4 | (+/-)-1-(4-fluoro-3-{[4,4,4-trifluoro-3-methyl-2-(4-methylpiperidin-1-yl)butanoyl]amino}benzyl)cyclopropanecarboxylic acid (diastereomer 1)<br><br>from (+/-)-tert-butyl-1-{4-fluoro-3-[(4,4,4-trifluorovalyl)amino]benzyl}cyclopropanecarboxylate (diastereomer 1) and 3-methylpentanedial | LC-MS (Method 2): $R_t$ = 1.18 min; m/z = 445 (M + H)$^+$.<br>$^1$H-NMR (400 MHz, DMSO-$d_6$): δ [ppm] = 0.78-0.84 (m, 2H), 0.87 (d, 3H), 0.95-1.05 (m, 1H), 1.06-1.13 (m, 5H), 1.13-1.22 (m, 1H), 1.22-1.33 (m, 1H), 1.58 (t, 2H), 2.02 (t, 1H), 2.36-2.46 (m, 1H), 2.59-2.67 (m, 1H), 2.84 (s, 2H), 2.85-2.92 (m, 1H), 2.98-3.08 (m, 1H), 3.47 (d, 1H), 7.01-7.09 (m, 1H), 7.10-7.19 (m, 1H), 7.58-7.68 (m, 1H), 9.70 (s, 1H), 12.15 (br. s, 1H). |
| 5 | (+/-)-3-(4-fluoro-3-{[4,4,4-trifluoro-3-methyl-2-(4-methylpiperidin-1-yl)butanoyl]amino}phenyl)propanoic acid (diastereomer 1)<br><br>from (+/-)-tert-butyl 3-{4-fluoro-3-[(4,4,4-trifluorovalyl)amino]phenyl}propanoate (diastereomer 1) and 3-methylpentanedial | LC-MS (Method 2): $R_t$ = 1.11 min; m/z = 419 (M + H)$^+$.<br>$^1$H-NMR (400 MHz, DMSO-$d_6$): δ [ppm] = 0.87 (d, 3H), 0.95-1.06 (m, 1H), 1.10 (d, 3H), 1.12-1.22 (m, 1H), 1.22-1.33 (m, 1H), 1.57 (t, 2H), 2.03 (t, 1H), 2.37-2.46 (m, 1H), 2.49-2.53 (m, about 2H, obscured), 2.63 (d, 1H), 2.79 (t, 2H), 2.89 (d, 1H), 2.97-3.08 (m, 1H), 3.49 (d, 1H), 6.98-7.08 (m, 1H), 7.15 (dd, 1H), 7.60 (dd, 1H), 9.70 (s, 1H), 12.12 (s, 1H). |

| Example | Name/Structure/Starting materials | Analytical data |
|---|---|---|
| 6 | (+/−)-3-(4-fluoro-3-{[4,4,4-trifluoro-3-methyl-2-(4-methylpiperidin-1-yl)butanoyl]amino}phenyl)propanoic acid (diastereomer 2)<br>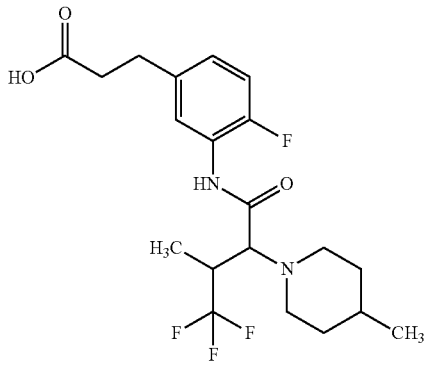<br>from (+/−)-tert-butyl 3-{4-fluoro-3-[(4,4,4-trifluorovalyl)amino]phenyl}propanoate (diastereomer 2) and 3-methylpentanedial | LC-MS (Method 2): $R_t$ = 0.97 min; m/z = 419 (M + H)$^+$.<br>$^1$H-NMR (400 MHz, DMSO-d$_6$): δ [ppm] = 0.86 (d, 3H), 0.94-1.02 (m, 1H), 1.03 (d, 3H), 1.05-1.18 (m, 1H), 1.20-1.34 (m, 1H), 1.56 (t, 2H), 2.04 (t, 1H), 2.30-2.41 (m, 1H), 2.79 (t, 2H), 2.87 (d, 2H), 2.89-2.99 (m, 1H), 3.58 (d, 1H), 7.01-7.09 (m, 1H), 7.17 (dd, 1H), 7.61 (dd, 1H), 9.77 (s, 1H), 12.14 (s, 1H). |
| 7 | (+)-3-(4-fluoro-3-{[(2R,3R)-4,4,4-trifluoro-3-methyl-2-(4-methylpiperidin-1-yl)butanoyl]amino}phenyl)propanoic acid<br>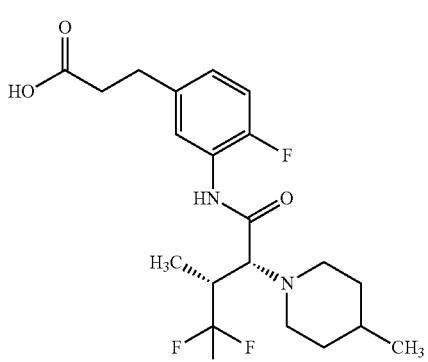<br>from (+)-tert-butyl 3-(4-fluoro-3-{[(3R)-4,4,4-trifluoro-D-valyl]amino}phenyl)propanoate and 3-methylpentanedial | LC-MS (Method 2): $R_t$ = 1.11 min; m/z = 419 (M + H)$^+$.<br>$^1$H-NMR (400 MHz, DMSO-d$_6$): δ [ppm] = 0.86 (d, 3H), 0.95-1.07 (m, 1H), 1.09 (d, 3H), 1.11-1.21 (m, 1H), 1.21-1.36 (m, 1H), 1.57 (t, 2H), 1.95-2.07 (m, 1H), 2.44 (t, about 2H), 2.63 (d, 1H), 2.77 (t, 2H), 2.88 (d, 1H), 2.97-3.08 (m, 2H), 3.49 (d, 2H), 6.96-7.07 (m, 1H), 7.13 (dd, 1H), 7.58 (dd, 1H), 9.70 (s, 1H).<br>$[α]_D^{20}$ = +27.5°, c = 0.430, chloroform. |
| 8 | (+/−)-1-(3-{[2-(4-ethylpiperidin-1-yl)-4,4,4-trifluoro-3-methylbutanoyl]amino}-4-fluorobenzyl)cyclopropanecarboxylic acid (diastereomer 1)<br>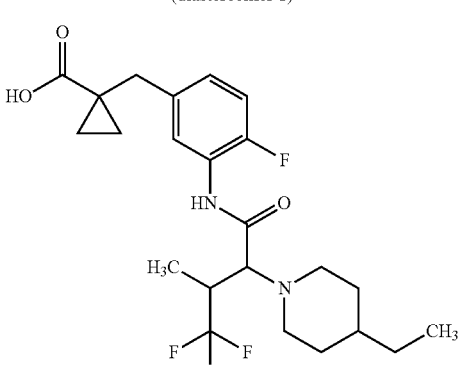<br>from (+/−)-tert-butyl-1-{4-fluoro-3-[(4,4,4-trifluorovalyl)amino]benzyl}cyclopropanecarboxylate (diastereomer 1) and 3-ethylpentanedial | LC-MS (Method 2): $R_t$ = 1.26 min; m/z = 459 (M + H)$^+$.<br>$^1$H-NMR (400 MHz, DMSO-d$_6$): δ [ppm] = 0.79-0.86 (m, 5H), 0.94-1.24 (m, 10H), 1.63 (t, 2H), 2.01 (t, 1H), 2.36-2.45 (m, 1H), 2.65 (d, 1H), 2.84 (s, 2H), 2.91 (d, 1H), 2.98-3.09 (m, 1H), 3.47 (d, 1H), 7.01-7.09 (m, 1H), 7.10-7.20 (m, 1H), 7.61 (dd, 1H), 9.68 (s, 1H), 12.13 (br. s, 1H). |

-continued

| Example | Name/Structure/Starting materials | Analytical data |
|---|---|---|
| 9 | (+/-)-3-(3-{[2-(4-ethylpiperidin-1-yl)-4,4,4-trifluoro-3-methylbutanoyl]amino}-4-fluorophenyl)propanoic acid (diastereomer 1)<br />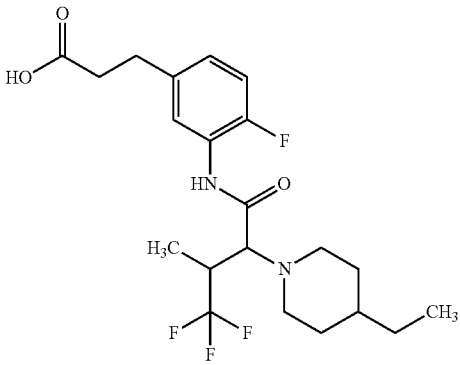<br />from (+/-)-tert-butyl 3-{4-fluoro-3-[(4,4,4-trifluorovalyl)amino]phenyl}propanoate (diastereomer 1) and 3-ethylpentanedial | LC-MS (Method 2): $R_t$ = 1.15 min; m/z = 433 (M + H)$^+$. $^1$H-NMR (400 MHz, DMSO-$d_6$): δ [ppm] = 0.83 (t, 3H), 0.94-1.24 (m, 8H), 1.63 (t, 2H), 1.96-2.06 (m, 1H), 2.35-2.46 (m, 1H), 2.52-2.56 (m, about 2H, obscured), 2.65 (d, 1H), 2.79 (t, 2H), 2.91 (d, 1H), 2.97-3.08 (m, 1H), 3.49 (d, 1H), 6.98-7.07 (m, 1H), 7.15 (dd, 1H), 7.59 (dd, 1H), 9.70 (s, 1H), 12.13 (br. s, 1H). |
| 10 | (+/-)-3-(3-{[2-(4-ethylpiperidin-1-yl)-4,4,4-trifluoro-3-methylbutanoyl]amino}-4-fluorophenyl)propanoic acid (diastereomer 2)<br />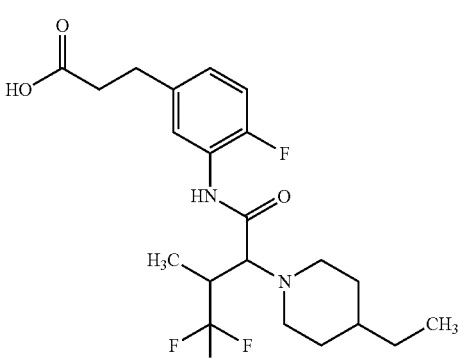<br />from (+/-)-tert-butyl 3-{4-fluoro-3-[(4,4,4-trifluorovalyl)amino]phenyl}propanoate (diastereomer 2) and 3-ethylpentanedial | LC-MS (Method 2): $R_t$ = 1.01 min; m/z = 433 (M + H)$^+$. $^1$H-NMR (400 MHz, DMSO-$d_6$): δ [ppm] = 0.83 (t, 3H), 0.94-1.23 (m, 8H), 1.53-1.69 (m, 2H), 2.04 (t, 1H), 2.36 (t, 1H), 2.80 (t, 2H), 2.84-3.04 (m, 3H), 3.58 (d, 1H), 6.99-7.10 (m, 1H), 7.17 (dd, 1H), 7.58-7.71 (m, 1H), 9.76 (s, 1H), 12.15 (br. s, about 1H). |
| 11 | (+/-)-3-(3-(4-chloro-3-{[2-(4-ethylpiperidin-1-yl)-4,4,4-trifluoro-3-methylbutanoyl]amino}phenyl)propanoic acid (diastereomer 1)<br />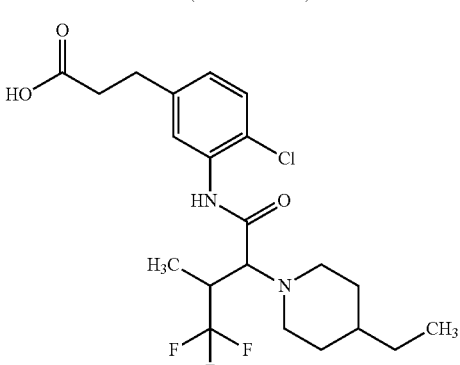<br />from (+/-)-tert-butyl 3-{4-chloro-3-[(4,4,4-trifluorovalyl)amino]phenyl}propanoate (diastereomer 1) and 3-ethylpentanedial | LC-MS (Method 2): $R_t$ = 1.29 min; m/z = 449 (M + H)$^+$. $^1$H-NMR (400 MHz, DMSO-$d_6$): δ [ppm] = 0.83 (t, 3H), 0.95-1.05 (m, 1H), 1.07-1.28 (m, 7H), 1.64 (dd, 2H), 2.00-2.14 (m, 1H), 2.39 (t, 2H), 2.53-2.57 (m, about 1H, obscured), 2.66 (d, 1H), 2.76 (t, 2H), 2.94 (d, 1H), 2.99-3.09 (m, 1H), 3.51 (d, 1H), 7.07 (dd, 1H), 7.37 (d, 1H), 7.40-7.52 (m, 1H), 9.60 (s, 1H). |

| Example | Name/Structure/Starting materials | Analytical data |
|---------|-----------------------------------|-----------------|
| 12 | (+/-)-3-(4-chloro-3-{[2-(4-ethylpiperidin-1-yl)-4,4,4-trifluoro-3-methylbutanoyl]amino}phenyl)propanoic acid (diastereomer 2)<br>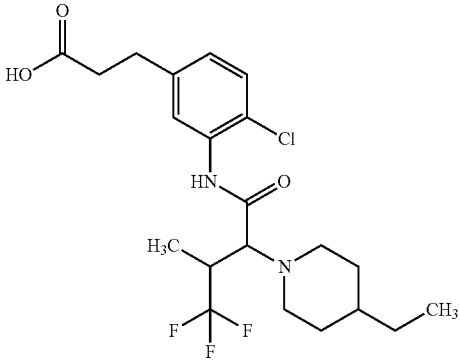<br>from (+/-)-tert-butyl 3-{4-chloro-3-[(4,4,4-trifluorovalyl)amino]phenyl}propanoate (diastereomer 2) and 3-ethylpentanedial | LC-MS (Method 2): $R_t$ = 1.20 min; m/z = 449 (M + H)$^+$.<br>$^1$H-NMR (400 MHz, DMSO-$d_6$): δ [ppm] = 0.83 (t, 3H), 0.94-1.24 (m, 8H), 1.58-1.66 (m, 2H), 2.09 (t, 1H), 2.39-2.48 (m, 1H), 2.81 (t, 2H), 2.84-3.03 (m, 3H), 3.59 (d, 1H), 7.10 (dd, 1H), 7.41 (d, 1H), 7.51-7.67 (m, 1H), 9.70 (s, 1H), 12.20 (br. s, about 1H). |
| 13 | (+/-)-3-(4-chloro-3-{[4,4,4-trifluoro-3-methyl-2-(4-methylpiperidin-1-yl)butanoyl]amino}phenyl)propanoic acid (diastereomer 1)<br>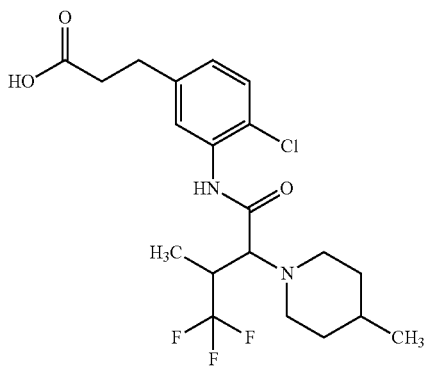<br>from (+/-)-tert-butyl 3-{4-chloro-3-[(4,4,4-trifluorovalyl)amino]phenyl}propanoate (diastereomer 1) and 3-methylpentanedial | LC-MS (Method 2): $R_t$ = 1.21 min; m/z = 435 (M + H)$^+$.<br>$^1$H-NMR (400 MHz, DMSO-$d_6$): δ [ppm] = 0.87 (d, 3H), 0.96-1.08 (m, 1H), 1.10 (d, 3H), 1.12-1.23 (m, 1H), 1.23-1.38 (m, 1H), 1.49-1.66 (m, 2H), 2.02-2.12 (m, 1H), 2.23 (t, 2H), 2.54-2.68 (m, about 2H), 2.73 (t, 2H), 2.91 (d, 1H), 2.99-3.09 (m, 1H), 3.50 (d, 1H), 7.06 (dd, 1H), 7.34 (d, 1H), 7.38-7.50 (m, 1H), 9.61 (s, 1H). |
| 14 | (+/-)-3-[4-chloro-3-({4,4,4-trifluoro-3-methyl-2-[4-(trifluoromethyl)piperidin-1-yl]butanoyl}amino)phenyl]propanoic acid (diastereomer 1)<br>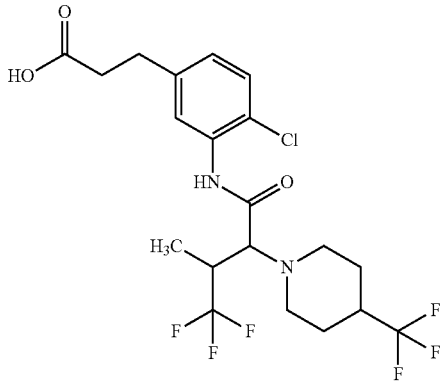<br>from (+/-)-tert-butyl 3-{4-chloro-3-[(4,4,4-trifluorovalyl)amino]phenyl}propanoate (diastereomer 1) and 3-(trifluoromethyl)pentanedial | LC-MS (Method 2): $R_t$ = 1.23 min; m/z = 489 (M + H)$^+$.<br>$^1$H-NMR (400 MHz, DMSO-$d_6$): δ [ppm] = 1.11 (d, 3H), 1.30-1.40 (m, 1H), 1.46-1.55 (m, 1H), 1.69-1.88 (m, 2H), 2.05-2.18 (m, 1H), 2.20-2.35 (m, 1H), 2.56-2.65 (m, 1H), 2.74-2.85 (m, 3H), 3.05 (d, 2H), 3.56 (d, 1H), 7.09 (dd, 1H), 7.41 (d, 1H), 7.47 (d, 1H), 9.67 (s, 1H), 12.16 (br. s, 1H). |

| Example | Name/Structure/Starting materials | Analytical data |
|---|---|---|
| 15 | (+/-)-3-(3-{[2-(6-azaspiro[2.5]oct-6-yl)-4,4,4-trifluoro-3-methylbutanoyl]amino}-4-fluorophenyl)propanoic acid (diastereomer 1)<br>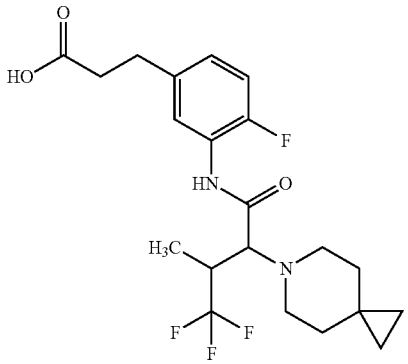<br>from (+/-)-tert-butyl 3-{4-fluoro-3-[(4,4,4-trifluorovalyl)amino]phenyl}propanoate (diastereomer 1) and 2,2'-cyclopropane-1,1-diyldiacetaldehyde | LC-MS (Method 3): $R_t$ = 1.26 min; m/z = 431 (M + H)$^+$.<br>$^1$H-NMR (400 MHz, DMSO-$d_6$): δ [ppm] = 0.20 (s, 4H), 1.14 (d, 3H), 1.30 (br. s, 4H), 2.50-2.63 (m, about 6H, obscured), 2.78 (t, 2H), 3.02-3.13 (m, 1H), 3.55 (d, 1H), 7.02-7.08 (m, 1H), 7.18 (t, 1H), 7.65 (d, 1H), 9.75 (s, 1H), 12.14 (br. s, 1H). |
| 16 | (+)-3-(3-{[(2R,3R)-2-(6-azaspiro[2.5]oct-6-yl)-4,4,4-trifluoro-3-methylbutanoyl]amino}-4-fluorophenyl)propanoic acid<br>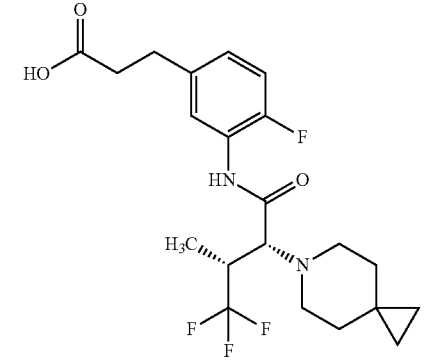<br>from (+)-tert-butyl 3-(4-fluoro-3-{[(3R)-4,4,4-trifluoro-D-valyl]amino}phenyl)propanoate and 2,2'-cyclopropane-1,1-diyldiacetaldehyde | LC-MS (Method 2): $R_t$ = 1.14 min; m/z = 431 (M + H)$^+$.<br>$^1$H-NMR (400 MHz, DMSO-$d_6$): δ [ppm] = 0.20 (s, 4H), 1.13 (d, 3H), 1.21-1.41 (m, 4H), 2.31 (t, 2H), 2.52-2.63 (m, about 4H, obscured), 2.74 (t, 2H), 3.00-3.10 (m, 1H), 3.53 (d, 1H), 6.95-7.05 (m, 1H), 7.07-7.16 (m, 1H), 7.59 (d, 1H), 9.72 (s, 1H).<br>$[α]_D^{20}$ = +23.2°, c = 0.435, chloroform. |
| 17 | (-)-3-[4-chloro-3-({(2R,3R)-4,4,4-trifluoro-3-methyl-2-[4-(trifluoromethyl)piperidin-1-yl]butanoyl}amino)phenyl]propanoic acid<br><br>from (+)-tert-butyl 3-(4-chloro-3-{[(3R)-4,4,4-trifluoro-D-valyl]amino}phenyl)propanoate and 3-(trifluoromethyl)pentanedial | LC-MS (Method 3): $R_t$ = 1.38 min; m/z = 489 (M + H)$^+$.<br>$^1$H-NMR (400 MHz, DMSO-$d_6$): δ [ppm] = 1.11 (d, 3H), 1.28-1.41 (m, 1H), 1.43-1.56 (m, 1H), 1.69-1.87 (m, 2H), 2.07-2.18 (m, 1H), 2.21-2.35 (m, 1H), 2.55-2.65 (m, 1H), 2.74-2.86 (m, 3H), 3.03-3.10 (m, 2H), 3.56 (d, 1H), 7.09 (dd, 1H), 7.41 (d, 1H), 7.47 (d, 1H), 9.67 (s, 1H), 12.16 (br. s, 1H).<br>$[α]_D^{20}$ = -5.1°, c = 0.370, chloroform. |

-continued

| Example | Name/Structure/Starting materials | Analytical data |
| --- | --- | --- |
| 18 | (+)-3-(3-{[(2R,3R)-2-(4-cyclopropylpiperidin-1-yl)-4,4,4-trifluoro-3-methylbutanoyl]amino}-4-fluorophenyl)propanoic acid<br><br>from (+)-tert-butyl 3-(4-fluoro-3-{[(3R)-4,4,4-trifluoro-D-valyl]amino}phenyl)propanoate and 3-cyclopropylpentanedial | LC-MS (Method 5): $R_t$ = 2.39 min; m/z = 445 (M + H)$^+$.<br>$^1$H-NMR (400 MHz, DMSO-$d_6$): δ [ppm] = 0.04 (d, 2H), 0.33 (d, 2H), 0.51 (br. s, 2H), 1.13 (d, 3H), 1.15-1.42 (m, about 3H), 1.68 (br. t, 2H), 2.32-2.46 (m, 1H), 2.64-2.85 (m, 3H), 2.96 (br. s, 1H), 3.07 (br. s, 1H), 6.97-7.08 (m, 1H), 7.15 (dd, 1H), 7.59 (dd, 1H), 9.76 (br. s, 1H).<br>$[α]_D^{20}$ = +32.9°, c = 0.385, methanol. |
| 19 | 3-(3-{[(2R,3R)-2-(6-azaspiro[2.5]oct-6-yl)-4,4,4-trifluoro-3-methylbutanoyl]amino}-4-chlorophenyl)propanoic acid<br><br>from (+)-tert-butyl 3-(4-chloro-3-{[(3R)-4,4,4-trifluoro-D-valyl]amino}phenyl)propanoate and 2,2'-cyclopropane-1,1-diyldiacetaldehyde | LC-MS (Method 3): $R_t$ = 1.36 min; m/z = 447 (M + H)$^+$.<br>$^1$H-NMR (400 MHz, DMSO-$d_6$): δ [ppm] = 0.16-0.25 (m, 4H), 1.14 (d, 3H), 1.26-1.38 (m, 4H), 2.52-2.57 (m, about 4H), 2.60-2.72 (m, 2H), 2.81 (t, 2H), 3.01-3.14 (m, 1H), 3.56 (d, 1H), 7.09 (dd, 1H), 7.41 (d, 1H), 7.48 (d, 1H), 9.62 (s, 1H), 12.16 (br. s, 1H).<br>$[α]_D^{20}$ = -7.8°, c = 0.370, chloroform. |
| 20 | (3S)-3-(4-chloro-3-{[4,4,4-trifluoro-3-methyl-2-(4-methylpiperidin-1-yl)butanoyl]amino}phenyl)butanoic acid (diastereomer mixture 1)<br><br>from tert-butyl (3S)-3-{4-chloro-3-[(4,4,4-trifluorovalyl)amino]phenyl}butanoate (diastereomer mixture 1) and 3-methylpentanedial | LC-MS (Method 2:) $R_t$ = 1.25 min; m/z = 449 (M + H)$^+$. |

| Example | Name/Structure/Starting materials | Analytical data |
| --- | --- | --- |
| 21 | (3S)-3-(3-{[2-(6-azaspiro[2.5]oct-6-yl)-4,4,4-trifluoro-3-methylbutanoyl]amino}-4-chlorophenyl)butanoic acid (diastereomer mixture 1)<br><br>from tert-butyl (3S)-3-{4-chloro-3-[(4,4,4-trifluorovalyl)amino]phenyl}butanoate (diastereomer mixture 1) and 2,2'-cyclopropane-1,1-diyldiacetaldehyde | LC-MS (Method 2): $R_t$ = 1.28 min; m/z = 479 (M + H)$^+$.<br>$^1$H-NMR (400 MHz, DMSO-$d_6$): δ [ppm] = 0.20 (s, 4H), 1.14 (d, 3H), 1.20 (d, 3H), 1.28-1.40 (m, 4H), 2.52-2.72 (m, 4H), 3.04-3.15 (m, 2H), 3.57 (d, 1H), 6.12 (d, 1H), 7.42 (d, 1H), 7.48 (s, 1H), 9.67 (s, 1H), 12.20 (br. s, 1H). |
| 22 | (+)-3-(4-fluoro-3-{[(2R,3R)-4,4,4-trifluoro-3-methyl-2-(4-phenylpiperidin-1-yl)butanoyl]amino}phenyl)propanoic acid<br><br>from (+)-tert-butyl 3-(4-fluoro-3-{[(3R)-4,4,4-trifluoro-D-valyl]amino}phenyl)propanoate and 3-phenylpentanedial | LC-MS (Method 2): $R_t$ = 1.22 min; m/z = 481 (M + H)$^+$.<br>$^1$H-NMR (400 MHz, DMSO-$d_6$): δ [ppm] = 1.16 (d, 3H), 1.50-1.60 (m, 1H), 1.62-1.85 (m, 3H), 2.19 (t, 1H), 2.40-2.49 (m, 1H), 2.55-2.68 (m, about 3H), 2.75-2.83 (m, 3H), 2.98-3.15 (m, 2H), 3.57 (d, 1H), 6.99-7.09 (m, 1H), 7.12-7.34 (m, 6H), 7.66 (dd, 1H), 9.78 (s, 1H), 12.18 (br. s, about 1H).<br>$[α]_D^{20}$ = +49.3°, c = 0.535, chloroform. |
| 23 | (-)-(3S)-3-[4-chloro-3-({(2R,3R)-4,4,4-trifluoro-3-methyl-2-[4-(trifluoromethyl)piperidin-1-yl]-butanoyl}amino)phenyl]butanoic acid<br><br>from tert-butyl (3S)-3-(4-chloro-3-{[(3R)-4,4,4-trifluoro-D-valyl]amino}phenyl)butanoate and 3-(trifluoromethyl)pentanedial | LC-MS (Method 3): $R_t$ = 1.42 min; m/z = 503 (M + H)$^+$.<br>$^1$H-NMR (400 MHz, DMSO-$d_6$): δ [ppm] = 1.11 (d, 3H), 1.19 (d, 3H), 1.28-1.41 (m, 1H), 1.44-1.58 (m, 1H), 1.71-1.89 (m, 2H), 2.09-2.19 (m, 1H), 2.21-2.38 (m, 2H), 2.56-2.68 (m, 1H), 2.79 (d, 1H), 3.00-3.21 (m, 4H), 3.57 (d, 1H), 7.13 (dd, 1H), 7.42 (d, 1H), 7.48 (d, 1H), 9.68 (s, 1H).<br>$[α]_D^{20}$ = -14.5°, c = 0.370, chloroform. |

-continued

| Example | Name/Structure/Starting materials | Analytical data |
|---|---|---|
| 24 | (−)-3-[4-fluoro-3-({(2R,3R)-4,4,4-trifluoro-3-methyl-2-[4-(trifluoromethyl)piperidin-1-yl]butanoyl}amino)phenyl]propanoic acid<br>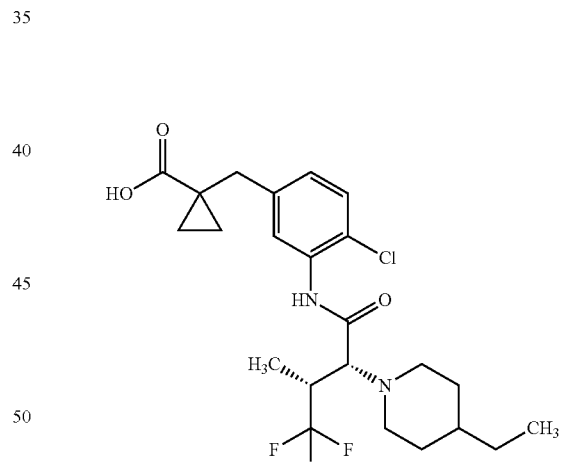<br>from (+)-tert-butyl 3-(4-fluoro-3-{[(3R)-4,4,4-trifluoro-D-valyl]amino}phenyl)propanoate and 3-(trifluoromethyl)pentanedial | LC-MS (Method 2): $R_t$ = 1.17 min; m/z = 473 (M + H)$^+$.<br>$^1$H-NMR (400 MHz, DMSO-$d_6$): δ [ppm] = 1.10 (d, 3H), 1.34 (qd, 1H), 1.48 (qd, 1H), 1.79 (t, 2H), 2.03-2.13 (m, 1H), 2.19-2.34 (m, 1H), 2.42-2.48 (m, 1H), 2.74-2.83 (m, 3H), 2.98-3.11 (m, 2H), 3.55 (d, 1H), 6.97-7.07 (m, 1H), 7.16 (dd, 1H), 7.64 (dd, 1H), 9.80 (s, 1H).<br>$[α]_D^{20}$ = +27.8°, c = 0.500, chloroform. |

Example 25

1-(3-{[(2R,3R)-2-(6-Azaspiro[2.5]oct-6-yl)-4,4,4-trifluoro-3-methylbutanoyl]amino}-4-chlorobenzyl)cyclopropanecarboxylic acid

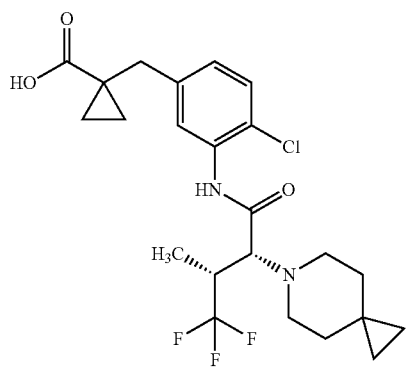 [SMILES: C[C@H]([C@H](C(=O)Nc1cc(CC2(C(=O)O)CC2)ccc1Cl)N1CCC2(CC1)CC2)C(F)(F)F]

The title compound was obtained according to General Procedure 4 from (+)-tert-butyl 1-(4-chloro-3-{[(3R)-4,4,4-trifluoro-D-valyl]amino}benzyl)cyclopropanecarboxylate and 2,2'-cyclopropane-1,1-diyldiacetaldehyde. Yield: 111.7 mg (63.8% of theory).

LC-MS (Method 2): $R_t$=1.25 min; m/z=473 (M+H)$^+$.

$^1$H-NMR (400 MHz, DMSO-$d_6$): δ [ppm]=0.21 (s, 4H), 0.82 (q, 2H), 1.12-1.17 (m, 5H), 1.31 (br. s, 4H), 2.52-2.59 (m, 2H), 2.61-2.70 (m, 2H), 2.80-2.94 (m, 2H), 2.98-3.15 (m, 1H), 3.53 (d, 1H), 7.11 (dd, 1H), 7.39 (d, 1H), 7.50 (d, 1H), 9.61 (s, 1H).

Example 26

1-(4-Chloro-3-{[(2R,3R)-2-(4-ethylpiperidin-1-yl)-4,4,4-trifluoro-3-methylbutanoyl]amino}benzyl)cyclopropanecarboxylic acid The title compound was obtained according to General Procedure 4 from (+)-tert-butyl 1-(4-chloro-3-{[(3R)-4,4,4-trifluoro-D-valyl]amino}benzyl)cyclopropanecarboxylate and 3-ethylpentanedial. Yield: 33 mg (39.7% of theory).

LC-MS (Method 2): $R_t$=1.31 min; m/z=475 (M+H)$^+$.

$^1$H-NMR (400 MHz, DMSO-$d_6$): δ [ppm]=0.76-0.88 (m, 5H), 0.95-1.26 (m, about 10H), 1.64 (t, 2H), 2.06 (t, 1H), 2.52-2.60 (m, about 1H), 2.63-2.72 (m, 1H), 2.86 (s, 2H), 2.90-2.97 (m, 1H), 2.99-3.10 (m, 1H), 3.50 (d, 1H), 7.11 (dd, 1H), 7.39 (d, 1H), 7.43-7.54 (m, 1H), 9.60 (s, 1H).

General Procedure 5: Cleavage of Ethyl Esters to the Corresponding Carboxylic Acids Using a Mixture of Hydrochloric Acid or Sulphuric Acid with Acetic Acid A solution of the ethyl ester in question in a mixture (about 1:1 to 3:1) of acetic acid and concentrated hydrochloric acid or of acetic acid and 10% strength, 20% strength or semiconcentrated sulphuric acid is stirred at temperatures of from 80° C. to 140° C. (optionally under reflux) for 30 min up to 12 h. After cooling, the reaction mixture is either concentrated directly under reduced pressure or added to water. The aqueous phase is then adjusted to about neutral using aqueous sodium hydroxide solution and extracted with ethyl acetate or dichloromethane, and the combined organic phases are concentrated under reduced pressure. The residue is taken up in ethyl acetate and washed with water (adjusted to about neutral (pH 6-7.7) by addition of a little sat. sodium bicarbonate solution). After concentration under reduced pressure, the crude product can be purified by preparative RP-HPLC (mobile phase acetonitrile/water or methanol/water gradient), by crystallization from acetonitrile or water/acetonitrile mixtures or by a combination of these methods.

The following examples were prepared according to General Procedure 5:

| Example | Name/Structure/Starting material | Analytical data |
| --- | --- | --- |
| 27 | (+)-(2S)-3-(4-chloro-3-{[(2R,3R)-4,4,4-trifluoro-3-methyl-2-(4-methylpiperidin-1-yl)butanoyl]amino}phenyl)-2-methylpropanoic acid<br>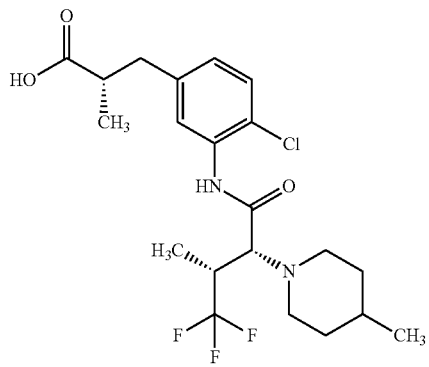<br>from ethyl (2S)-3-(4-chloro-3-{[(2R,3R)-4,4,4-trifluoro-3-methyl-2-(4-methylpiperidin-1-yl)butanoyl]amino}phenyl)-2-methylpropanoate | LC-MS (Method 2): $R_t$ = 1.25 min; m/z = 449 (M + H)$^+$.<br>$^1$H-NMR (400 MHz, DMSO-$d_6$): δ [ppm] = 0.87 (d, 3H), 0.97-1.07 (m, 4H), 1.11 (d, 3H), 1.15-1.36 (m, 2H), 1.54-1.63 (m, 2H), 1.97-2.13 (m, 1H), 2.54-2.69 (m, 4H), 2.82-2.95 (m, 2H), 2.99-3.09 (m, 1H), 3.51 (d, 1H), 7.04 (dd, 1H), 7.40 (d, 1H), 7.43 (d, 1H), 9.60 (s, 1H), 12.17 (br. s, 1H).<br>$[α]_D^{20}$ = +11.9°, c = 0.340, chloroform. |
| 28 | (2S)-3-(3-{[(2R,3R)-2-(6-azaspiro[2.5]oct-6-yl)-4,4,4-trifluoro-3-methylbutanoyl]amino}-4-fluorophenyl)-2-methylpropanoic acid<br>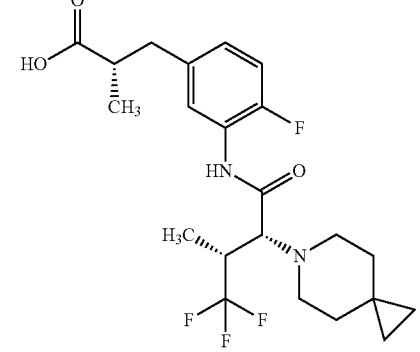<br>from ethyl (2S)-3-(3-{[(2R,3R)-2-(6-azaspiro[2.5]oct-6-yl)-4,4,4-trifluoro-3-methylbutanoyl]amino}-4-fluorophenyl)-2-methylpropanoate | LC-MS (Method 3): $R_t$ = 1.32 min; m/z = 445 (M + H)$^+$.<br>$^1$H-NMR (400 MHz, DMSO-$d_6$): δ [ppm] = 0.16-0.26 (m, 4H), 1.05 (d, 3H), 1.13 (d, 3H), 1.30 (br. s, 4H), 2.53-2.64 (m, about 6H, obscured), 2.80-2.91 (m, 1H), 3.00-3.10 (m, 1H), 3.54 (d, 1H), 7.00 (td, 1H), 7.17 (dd, 1H), 7.61 (dd, 1H), 9.74 (s, 1H), 12.18 (br. s, 1H). |

-continued

| Example | Name/Structure/Starting material | Analytical data |
|---|---|---|
| 29 | (−)-(2R)-3-(3-{[(2R,3R)-2-(6-azaspiro[2.5]oct-6-yl)-4,4,4-trifluoro-3-methylbutanoyl]amino}-4-chlorophenyl)-2-methylpropanoic acid<br><br>from ethyl (2R)-3-(3-{[(2R,3R)-2-(6-azaspiro[2.5]oct-6-yl)-4,4,4-trifluoro-3-methylbutanoyl]amino}-4-chlorophenyl)-2-methylpropanoate | LC-MS (Method 2): $R_t$ = 1.26 min; m/z = 461 (M + H)$^+$.<br>$^1$H-NMR (400 MHz, DMSO-$d_6$): δ [ppm] = 0.21 (br. s, 4H), 1.05 (d, 3H), 1.14 (d, 3H), 1.32 (br. s, 4H), 2.55-2.70 (m, about 6H), 2.80-2.94 (m, 1H), 3.02-3.12 (m, 1H), 3.55 (d, 1H), 7.05 (dd, 1H), 7.29-7.49 (m, 2H), 9.63 (s, 1H).<br>$[α]_D^{20}$ = −21.6°, c = 0.405, chloroform. |
| 30 | (+)-(2R)-3-(4-fluoro-3-{[(2R,3R)-4,4,4-trifluoro-3-methyl-2-(4-methylpiperidin-1-yl)butanoyl]amino}phenyl)-2-methylpropanoic acid<br><br>from ethyl (2R)-3-(4-fluoro-3-{[(2R,3R)-4,4,4-trifluoro-3-methyl-2-(4-methylpiperidin-1-yl)butanoyl]amino}phenyl)-2-methylpropanoate | LC-MS (Method 2): $R_t$ = 1.17 min; m/z = 433 (M + H)$^+$.<br>$^1$H-NMR (400 MHz, DMSO-$d_6$): δ [ppm] = 0.86 (d, 3H), 0.96-1.07 (m, 4H), 1.09 (d, 3H), 1.12-1.21 (m, 1H), 1.23-1.33 (m, 1H), 1.57 (t, 2H), 2.02 (t, 1H), 2.37-2.45 (m, 1H), 2.55-2.69 (m, about 3H), 2.80-2.93 (m, 2H), 2.97-3.08 (m, 1H), 3.49 (d, 1H), 6.93-7.03 (m, 1H), 7.15 (dd, 1H), 7.57 (dd, 1H), 9.71 (s, 1H).<br>$[α]_D^{20}$ = +9.2°, c = 0.450, chloroform. |
| 31 | (−)-(2R)-3-(4-chloro-3-{[(2R,3R)-4,4,4-trifluoro-3-methyl-2-(4-methylpiperidin-1-yl)butanoyl]amino}phenyl)-2-methylpropanoic acid<br><br>from ethyl (2R)-3-(4-chloro-3-{[(2R,3R)-4,4,4-trifluoro-3-methyl-2-(4-methylpiperidin-1-yl)butanoyl]amino}phenyl)-2-methylpropanoate | LC-MS (Method 4): $R_t$ = 2.54 min; m/z = 449 (M + H)$^+$.<br>$^1$H-NMR (400 MHz, DMSO-$d_6$): δ [ppm] = 0.87 (d, 3H), 0.95-1.07 (m, 4H), 1.10 (d, 3H), 1.13-1.36 (m, 2H), 1.51-1.65 (m, 2H), 2.06 (t, 1H), 2.56-2.68 (m, 4H), 2.81-2.95 (m, 2H), 2.99-3.09 (m, 1H), 3.51 (d, 1H), 7.04 (d, 1H), 7.35-7.52 (m, 2H), 9.61 (s, 1H), 12.19 (br. s, about 1H).<br>$[α]_D^{20}$ = −23.6°, c = 0.425, chloroform. |

| Example | Name/Structure/Starting material | Analytical data |
|---|---|---|
| 32 | (+)-(2S)-3-(4-fluoro-3-{[(2R,3R)-4,4,4-trifluoro-3-methyl-2-(4-methylpiperidin-1-yl)butanoyl]amino}phenyl)-2-methylpropanoic acid<br><br>from ethyl (2S)-3-(4-fluoro-3-{[(2R,3R)-4,4,4-trifluoro-3-methyl-2-(4-methylpiperidin-1-yl)butanoyl]amino}phenyl)-2-methylpropanoate | LC-MS (Method 2): $R_t$ = 1.13 min; m/z = 433 (M + H)⁺.<br>¹H-NMR (400 MHz, DMSO-$d_6$): δ [ppm] = 0.87 (d, 3H), 0.97-1.02 (m, 1H), 1.04 (d, 3H), 1.09 (d, 3H), 1.12-1.21 (m, 1H), 1.21-1.35 (m, 1H), 1.58 (t, 2H), 1.98-2.08 (m, 1H), 2.35-2.47 (m, 1H), 2.55-2.70 (m, 3H), 2.80-2.93 (m, 2H), 2.95-3.11 (m, 1H), 3.49 (d, 1H), 6.95-7.04 (m, 1H), 7.15 (dd, 1H), 7.57 (dd, 1H), 9.72 (s, 1H), 12.17 (br. s, 1H).<br>$[\alpha]_D^{20}$ = +42.6°, c = 0.430, chloroform. |
| 33 | (+)-(2R)-3-(3-{[(2R,3R)-2-(6-azaspiro[2.5]oct-6-yl)-4,4,4-trifluoro-3-methylbutanoyl]amino}-4-fluorophenyl)-2-methylpropanoic acid<br><br>from ethyl (2R)-3-(3-{[(2R,3R)-2-(6-azaspiro[2.5]oct-6-yl)-4,4,4-trifluoro-3-methylbutanoyl]amino}-4-fluorophenyl)-2-methylpropanoate | LC-MS (Method 2): $R_t$ = 1.20 min; m/z = 445 (M + H)⁺.<br>¹H-NMR (400 MHz, DMSO-$d_6$): δ [ppm] = 0.21 (s, 4H), 1.05 (d, 3H), 1.13 (d, 3H), 1.30 (br. s, 4H), 2.50-2.62 (m, about 6H, obscured), 2.80-2.92 (m, 1H), 3.00-3.10 (m, 1H), 3.54 (d, 1H), 6.94-7.06 (m, 1H), 7.17 (dd, 1H), 7.61 (dd, 1H), 9.74 (s, 1H), 12.17 (br. s, 1H).<br>$[\alpha]_D^{20}$ = +5.0°, c = 0.450, chloroform. |
| 34 | (+)-(2S)-3-[4-chloro-3-({(2R,3R)-4,4,4-trifluoro-3-methyl-2-[4-(trifluoromethyl)piperidin-1-yl]butanoyl}amino)phenyl]-2-methylpropanoic acid<br><br>from ethyl (2S)-3-[4-chloro-3-({(2R,3R)-4,4,4-trifluoro-3-methyl-2-[4-(trifluoromethyl)piperidin-1-yl]butanoyl}amino)phenyl]-2-methylpropanoate | LC-MS (Method 3): $R_t$ = 1.43 min; m/z = 503 (M + H)⁺.<br>¹H-NMR (400 MHz, DMSO-$d_6$): δ [ppm] = 1.04 (d, 3H), 1.11 (d, 3H), 1.24-1.41 (m, 1H), 1.42-1.61 (m, 1H), 1.70-1.86 (m, 2H), 2.05-2.18 (m, 1H), 2.22-2.35 (m, 1H), 2.52-2.74 (m, about 3H), 2.75-2.92 (m, 2H), 3.00-3.11 (m, 2H), 3.56 (d, 1H), 7.05 (dd, 1H), 7.36-7.53 (m, 2H), 9.68 (s, 1H), 12.26 (br. s, about 1H).<br>$[\alpha]_D^{20}$ = +12.7°, c = 0.350, chloroform. |

Example 35

(+)-1-(4-Fluoro-3-{[4,4,4-trifluoro-3-methyl-2-(piperidin-1-yl)butanoyl]amino}benzyl)cyclopropanecarboxylic acid (enantiomer 2)

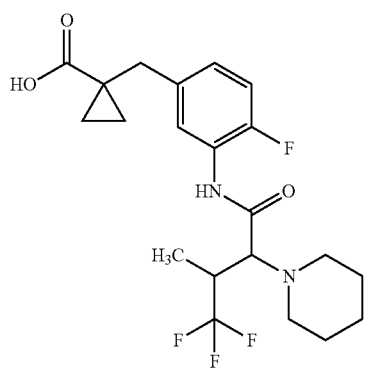 [SMILES: CC(C(C(=O)Nc1cc(CC2(C(=O)O)CC2)ccc1F)N1CCCCC1)C(F)(F)F]

The racemic mixture, obtained above, of 1-(4-fluoro-3-{[4,4,4-trifluoro-3-methyl-2-(piperidin-1-yl)butanoyl]amino}benzyl)cyclopropanecarboxylic acid (Example 2, racemic diastereomer 1) was separated further by preparative HPLC on a chiral phase [column: Daicel Chiralpak AD-H, 5 μm, 250 mm×20 mm; injection volume: 0.50 ml; temperature: 40° C.; mobile phase: 75% isohexan/25% isopropanol (+0.2% TFA+1% $H_2O$); flow rate: 15 ml/min; detection: 220 nm]. 290 mg of mixture gave 127 mg of the title compound as enantiomer 2.

LC-MS (Method 2): $R_t$=1.09 min; m/z=431 (M+H)$^+$.

$^1$H-NMR (400 MHz, DMSO-$d_6$): δ [ppm]=0.76-0.85 (m, 2H), 1.07-1.14 (m, 5H), 1.33-1.56 (m, 6H), 2.38-2.48 (m, 2H), 2.84 (s, 2H), 2.97-3.13 (m, 1H), 3.45 (d, 1H), 7.02-7.09 (m, 1H), 7.14 (dd, 1H), 7.63 (dd, 1H), 9.70 (s, 1H), 12.14 (br. s, 1H).

$[α]_D^{20}$=+21.2°, c=0.550, chloroform.

Example 36

(+)-1-(4-Fluoro-3-{[4,4,4-trifluoro-3-methyl-2-(4-methylpiperidin-1-yl)butanoyl]amino}benzyl)cyclopropanecarboxylic acid (enantiomer 2)

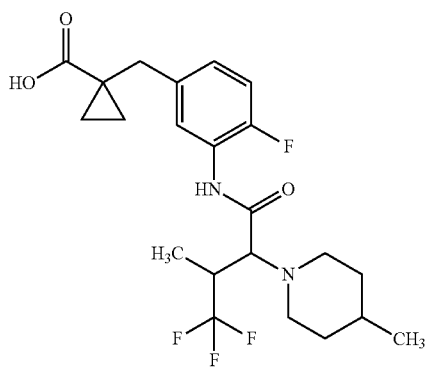 [SMILES: CC1CCN(C(C(=O)Nc2cc(CC3(C(=O)O)CC3)ccc2F)C(C)C(F)(F)F)CC1]

The racemic mixture, obtained above, of 1-(4-fluoro-3-{[4,4,4-trifluoro-3-methyl-2-(4-methylpiperidin-1-yl)butanoyl]amino}benzyl)cyclopropanecarboxylic acid (Example 4, racemic diastereomer 1) was separated further by preparative HPLC on a chiral phase [column: Daicel Chiralpak AD-H, 5 μm, 250 mm×20 mm; injection volume: 0.30 ml; temperature: 40° C.; mobile phase: 75% isohexane/25% isopropanol (+0.2% TFA+1% $H_2O$); flow rate: 15 ml/min; detection: 220 nm]. 400 mg of mixture gave 271 mg of the title compound (as enantiomer 2) as trifluoroacetic acid salt. This salt was then suspended in a little water/acetonitrile, neutralized by stirring with 1 N aqueous sodium hydroxide solution and then re-purified by preparative RP-HPLC (mobile phase: acetonitrile/water gradient). This gave 60 mg of the title compound.

LC-MS (Method 2): $R_t$=1.18 min; m/z=445 (M+H)$^+$.

$^1$H-NMR (400 MHz, DMSO-$d_6$): δ [ppm]=0.74-0.83 (m, 2H), 0.87 (d, 3H), 0.96-1.36 (m, 7H), 1.57 (t, 2H), 2.02 (t, 1H), 2.35-2.47 (m, 1H), 2.63 (d, 1H), 2.84 (s, 2H), 2.99 (d, 1H), 2.98-3.08 (m, 1H), 3.47 (d, 1H), 7.01-7.09 (m, 1H), 7.09-7.19 (m, 1H), 7.61 (dd, 1H), 9.70 (s, 1H).

$[α]_D^{20}$=+22.7°, c=0.460, chloroform.

Example 37

(+)-3-(4-Fluoro-3-{[4,4,4-trifluoro-3-methyl-2-(4-methylpiperidin-1-yl)butanoyl]amino}phenyl)propanoic acid trifluoroacetate (enantiomer 2)

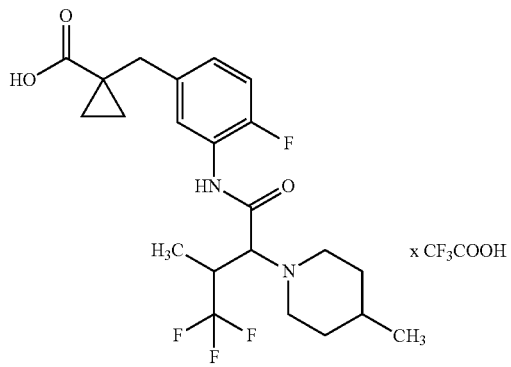 [SMILES: CC1CCN(C(C(=O)Nc2cc(CC3(C(=O)O)CC3)ccc2F)C(C)C(F)(F)F)CC1]

The racemic mixture, obtained above, of 3-(4-fluoro-3-{[4,4,4-trifluoro-3-methyl-2-(4-methylpiperidin-1-yl)butanoyl]amino}phenyl)propanoic acid (Example 6, racemic diastereomer 2) was separated further by preparative HPLC on a chiral phase [column: Daicel Chiralpak AD-H, 5 μm, 250 mm×20 mm; injection volume: 0.40 ml; temperature: 25° C.; mobile phase: 80% isohexane/20% ethanol (+0.2% TFA+1% $H_2O$); flow rate: 15 ml/min; detection: 220 nm]. 58 mg of mixture gave 38 mg of the title compound as enantiomer 2.

LC-MS (Method 2): $R_t$=0.95 min; m/z=419 (M+H)$^+$.

$[α]_D^{20}$=+15.8°, c=0.490, chloroform.

Example 38 and Example 39

1-(3-{[2-(4-Ethylpiperidin-1-yl)-4,4,4-trifluoro-3-methylbutanoyl]amino}-4-fluorobenzyl)cyclopropanecarboxylic acid (enantiomers 1 and 2)

The racemic mixture, obtained above, of 1-(3-{[2-(4-ethylpiperidin-1-yl)-4,4,4-trifluoro-3-methylbutanoyl]amino}-4-fluorobenzyl)cyclopropanecarboxylic acid (Example 8, racemic diastereomer 1) was separated further by preparative HPLC on a chiral phase [column: Daicel Chiralpak AD-H, 5 μm, 250 mm×20 mm; injection volume: 1.5 ml; temperature:

RT; mobile phase: 50% isohexane/50% isopropanol; flow rate: 18 ml/min; detection: 230 nm]. 275 mg of mixture gave 125 mg of enantiomer 1 (Example 38) and 122 mg of enantiomer 2 (Example 39):

Example 38

(−)-1-(3-{[(2S,3S)-2-(4-Ethylpiperidin-1-yl)-4,4,4-trifluoro-3-methylbutanoyl]amino}-4-fluorobenzyl)cyclopropanecarboxylic acid (enantiomer 1)

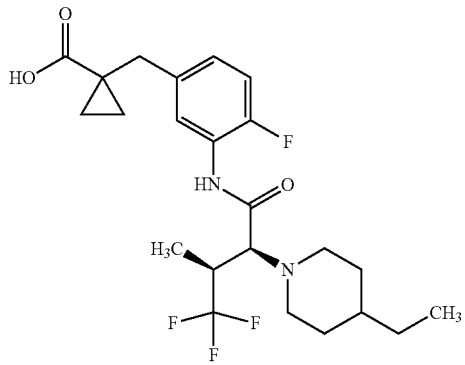 [SMILES: CCC1CCN([C@H](C(=O)Nc2cc(CC3(C(=O)O)CC3)ccc2F)[C@H](C)C(F)(F)F)CC1]

LC-MS (Method 2): $R_t$=1.25 min; m/z=459 (M+H)$^+$.
$^1$H-NMR (400 MHz, DMSO-d$_6$): δ [ppm]=0.77-0.88 (m, about 5H), 0.97-1.26 (m, about 10H), 1.63 (t, 2H), 1.97-2.05 (m, 1H), 2.36-2.45 (m, 1H), 2.65 (d, 1H), 2.84 (s, 2H), 2.88-2.96 (m, 1H), 2.96-3.10 (m, 1H), 3.47 (d, 1H), 7.00-7.10 (m, 1H), 7.10-7.22 (m, 1H), 7.61 (dd, 1H), 9.68 (s, 1H), 12.12 (br. s, 1H).
$[α]_D^{20}$=19.5°, c=0.545, chloroform.

Example 39

(+)-1-(3-{[(2R,3R)-2-(4-Ethylpiperidin-1-yl)-4,4,4-trifluoro-3-methylbutanoyl]amino}-4-fluorobenzyl)cyclopropanecarboxylic acid (enantiomer 2)

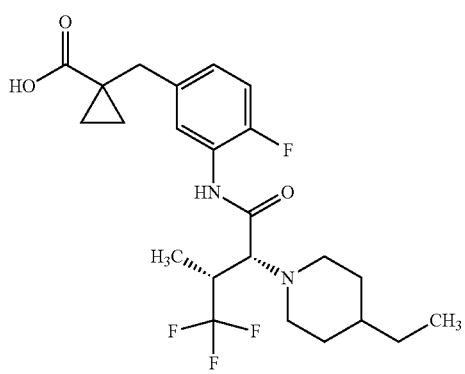 [SMILES: CCC1CCN([C@@H](C(=O)Nc2cc(CC3(C(=O)O)CC3)ccc2F)[C@@H](C)C(F)(F)F)CC1]

LC-MS (Method 2): $R_t$=1.25 min; m/z=459 (M+H)$^+$.
$^1$H-NMR (400 MHz, DMSO-d$_6$): δ [ppm]=0.80-0.88 (m, about 5H), 0.97-1.26 (m, about 10H), 1.63 (t, 2H), 2.01 (t, 1H), 2.36-2.45 (m, 1H), 2.65 (d, 1H), 2.84 (s, 2H), 2.91 (d, 1H), 2.98-3.08 (m, 1H), 3.47 (d, 1H), 7.00-7.09 (m, 1H), 7.10-7.19 (m, 1H), 7.61 (dd, 1H), 9.68 (s, 1H), 12.12 (br. s, 1H).
$[α]_D^{20}$=+20.3°, c=0.555, chloroform.

Example 40 and Example 41

3-(3-{[2-(4-Ethylpiperidin-1-yl)-4,4,4-trifluoro-3-methylbutanoyl]amino}-4-fluorophenyl)propanoic acid (enantiomers 1 and 2)

The racemic mixture, obtained above, of 3-(3-{[2-(4-ethylpiperidin-1-yl)-4,4,4-trifluoro-3-methylbutanoyl]amino}-4-fluorophenyl)propanoic acid (Example 9, racemic diastereomer 1) was separated further by preparative HPLC on a chiral phase [column: Daicel Chiralpak AD-H, 5 μm, 250 mm×20 mm; injection volume: 1.5 ml; temperature: RT; mobile phase: 60% isohexane/40% isopropanol; flow rate: 18 ml/min; detection: 230 nm]. 260 mg of mixture gave 101 mg of enantiomer 1 (Example 40) and 92 mg of enantiomer 2 (Example 41):

Example 40

(−)-3-(3-{[(2S,3S)-2-(4-Ethylpiperidin-1-yl)-4,4,4-trifluoro-3-methylbutanoyl]amino}-4-fluorophenyl)propanoic acid (enantiomer 1)

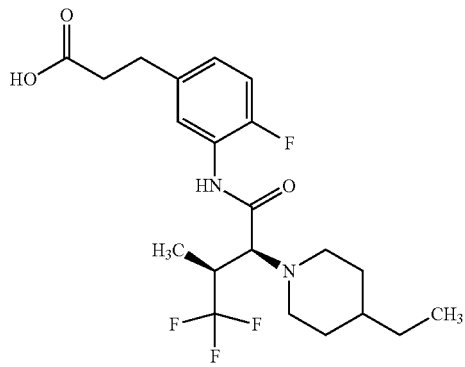 [SMILES: CCC1CCN([C@H](C(=O)Nc2cc(CCC(=O)O)ccc2F)[C@H](C)C(F)(F)F)CC1]

LC-MS (Method 2): $R_t$=1.18 min; m/z=433 (M+H)$^+$.
$^1$H-NMR (400 MHz, DMSO-d$_6$): δ [ppm]=0.83 (t, 3H), 0.96-1.25 (m, about 8H), 1.63 (t, 2H), 1.96-2.09 (m, 1H), 2.35-2.46 (m, 1H), 2.65 (d, 1H), 2.79 (t, 2H), 2.87-2.94 (m, 1H), 2.97-3.08 (m, 1H), 3.49 (d, 1H), 6.95-7.08 (m, 1H), 7.15 (dd, 1H), 7.59 (dd, 1H), 9.70 (s, 1H).
$[α]_D^{20}$=−20.8°, c=0.460, chloroform.

Example 41

(+)-3-(3-{[(2R,3R)-2-(4-Ethylpiperidin-1-yl)-4,4,4-trifluoro-3-methylbutanoyl]amino}-4-fluorophenyl)propanoic acid (enantiomer 2)

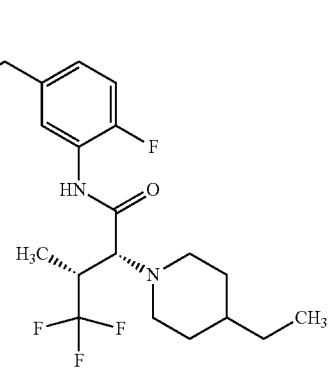

LC-MS (Method 2): $R_t$=1.18 min; m/z=433 (M+H)$^+$.

$^1$H-NMR (400 MHz, DMSO-d$_6$): δ [ppm]=0.83 (t, 3H), 0.96-1.26 (m, about 8H), 1.63 (t, 2H), 1.97-2.06 (m, 1H), 2.36-2.45 (m, 1H), 2.65 (d, 1H), 2.75-2.83 (m, 2H), 2.88-2.95 (m, 1H), 2.97-3.08 (m, 1H), 3.49 (d, 1H), 6.98-7.07 (m, 1H), 7.15 (dd, 1H), 7.59 (dd, 1H), 9.70 (s, 1H), 12.05 (br. s, about 1H).

$[α]_D^{20}$=+22.4°, c=0.575, chloroform.

Example 42 and Example 43

3-(4-Chloro-3-{[4,4,4-trifluoro-3-methyl-2-(4-methylpiperidin-1-yl)butanoyl]amino}phenyl)propanoic acid (enantiomer 1 and 2)

The racemic mixture, obtained above, of 3-(4-chloro-3-{[4,4,4-trifluoro-3-methyl-2-(4-methylpiperidin-1-yl)butanoyl]amino}phenyl)propanoic acid (Example 13, racemic diastereomer 1) was separated further by preparative HPLC on a chiral phase [column: Daicel Chiralpak AD-H, 5 µm, 250 mm×20 mm; injection volume: 1.0 ml; temperature: 30° C.; mobile phase: 70% isohexane/30% isopropanol; flow rate: 15 ml/min; detection: 220 nm]. 180 mg of mixture gave 77 mg of enantiomer 1 (Example 42) and 85 mg of enantiomer 2 (Example 43):

Example 42

3-(4-Chloro-3-{[(2S,3S)-4,4,4-trifluoro-3-methyl-2-(4-methylpiperidin-1-yl)butanoyl]amino}phenyl)propanoic acid (enantiomer 1)

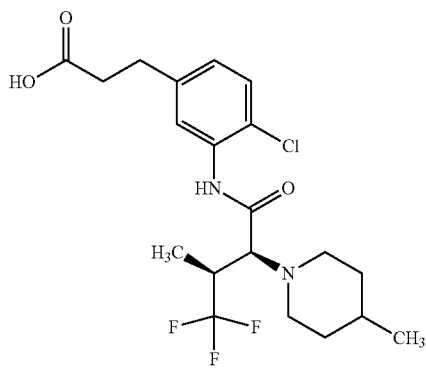

LC-MS (Method 3): $R_t$=1.33 min; m/z=435 (M+H)$^+$.

$^1$H-NMR (400 MHz, DMSO-d$_6$): δ [ppm]=0.87 (d, 3H), 0.96-1.08 (m, 1H), 1.10 (d, 3H), 1.12-1.23 (m, 1H), 1.23-1.37 (m, 1H), 1.51-1.68 (m, 2H), 2.07 (t, 1H), 2.26 (t, 2H), 2.55-2.60 (m, about 1H), 2.64 (d, 1H), 2.73 (t, 2H), 2.90 (d, 1H), 2.97-3.12 (m, 1H), 3.50 (d, 1H), 7.06 (dd, 1H), 7.35 (d, 1H), 7.38-7.44 (m, 1H), 9.62 (s, 1H).

Example 43

(+)-3-(4-Chloro-3-{[(2R,3R)-4,4,4-trifluoro-3-methyl-2-(4-methylpiperidin-1-yl)butanoyl]amino}phenyl)propanoic acid (enantiomer 2)

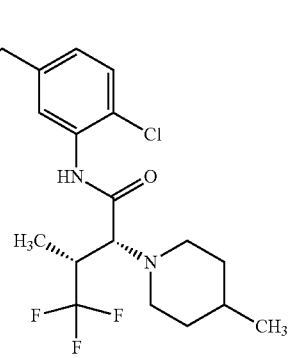

LC-MS (Method 3): $R_t$=1.33 min; m/z=435 (M+H)$^+$.

$^1$H-NMR (400 MHz, DMSO-d$_6$): δ [ppm]=0.87 (d, 3H), 0.96-1.08 (m, 1H), 1.10 (d, 3H), 1.12-1.23 (m, 1H), 1.23-1.37 (m, 1H), 1.51-1.66 (m, 2H), 2.01-2.16 (m, 1H), 2.28 (t, 2H), 2.52-2.60 (m, about 1H), 2.64 (d, 1H), 2.74 (t, 2H), 2.91 (d, 1H), 2.99-3.09 (m, 1H), 3.50 (d, 1H), 7.06 (dd, 1H), 7.36 (d, 1H), 7.39-7.46 (m, 1H), 9.61 (s, 1H).

$[α]_D^{20}$=+6.5°, c=0.400, chloroform.

Example 44 and Example 45

3-(4-Chloro-3-{[2-(4-ethylpiperidin-1-yl)-4,4,4-trifluoro-3-methylbutanoyl]amino}phenyl)propanoic acid (enantiomer 1 and 2)

The racemic mixture, obtained above, of 3-(4-chloro-3-{[2-(4-ethylpiperidin-1-yl)-4,4,4-trifluoro-3-methylbutanoyl]amino}phenyl)propanoic acid (Example 11, racemic diastereomer 1) was separated further by preparative HPLC on a chiral phase [column: Daicel Chiralpak AD-H, 5 µm, 250 mm×20 mm; injection volume: 1.0 ml; temperature: 30° C.; mobile phase: 70% isohexane/30% isopropanol; flow rate: 15 ml/min; detection: 220 nm]. 151 mg of mixture gave 52.2 mg of enantiomer 1 (Example 44) and 72.2 mg of enantiomer 2 (Example 45):

Example 44

(+)-3-(4-Chloro-3-{[(2S,3S)-2-(4-ethylpiperidin-1-yl)-4,4,4-trifluoro-3-methylbutanoyl]amino}phenyl)propanoic acid (enantiomer 1)

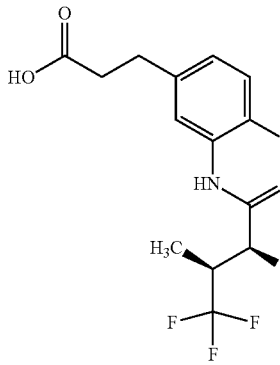

LC-MS (Method 2): $R_t$=1.26 min; m/z=449 (M+H)$^+$.

$^1$H-NMR (400 MHz, DMSO-d$_6$): δ [ppm]=0.84 (t, 3H), 0.94-1.26 (m, 8H), 1.56-1.71 (m, 2H), 2.05 (t, 1H), 2.39-2.48 (m, 2H), 2.52-2.58 (m, about 1H), 2.66 (d, 1H), 2.78 (t, 2H), 2.94 (d, 1H), 2.98-3.10 (m, 1H), 3.51 (d, 1H), 7.08 (dd, 1H), 7.39 (d, 1H), 7.41-7.49 (m, 1H), 9.61 (s, 1H).

$[α]_D^{20}$=+1.6°, c=0.350, chloroform.

Example 45

(+3-(4-Chloro-3-{[(2R,3R)-2-(4-ethylpiperidin-1-yl)-4,4,4-trifluoro-3-methylbutanoyl]amino}phenyl)propanoic acid (enantiomer 2)

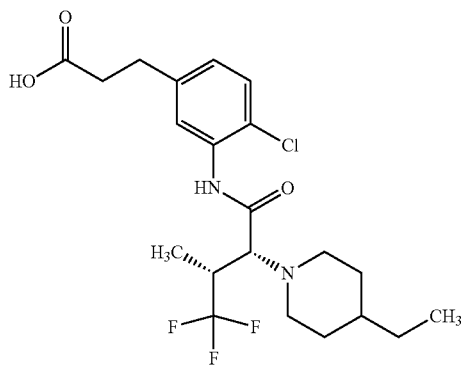 [SMILES: CCC1CCN([C@@H](C(=O)Nc2cc(CCC(=O)O)ccc2F)[C@@H](C)C(F)(F)F)CC1]

LC-MS (Method 2): $R_t$=1.26 min; m/z=449 (M+H)$^+$.

$^1$H-NMR (400 MHz, DMSO-d$_6$): δ [ppm]=0.84 (t, 3H), 0.95-1.25 (m, 8H), 1.64 (dd, 2H), 2.00-2.11 (m, 1H), 2.42-2.48 (m, 2H), 2.52-2.58 (m, about 1H), 2.66 (d, 1H), 2.78 (t, 2H), 2.94 (d, 1H), 2.99-3.09 (m, 1H), 3.51 (d, 1H), 7.08 (dd, 1H), 7.39 (d, 1H), 7.44 (d, 1H), 9.61 (s, 1H).

$[α]_D^{20}$=−0.7°, c=0.340, chloroform.

Example 46

(+)-(2S)-3-(3-{[(2R,3R)-2-(6-Azaspiro[2.5]oct-6-yl)-4,4,4-trifluoro-3-methylbutanoyl]amino}-4-chlorophenyl)-2-methylpropanoic acid (diastereomer 2)

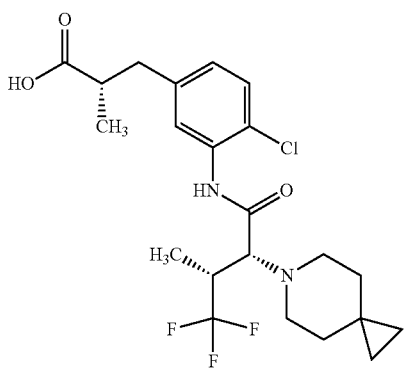 [SMILES: C[C@H]([C@H](C(=O)Nc1cc(C[C@H](C)C(=O)O)ccc1Cl)N1CCC2(CC1)CC2)C(F)(F)F]

From ethyl (2S)-3-(3-{[2-(6-azaspiro[2.5]oct-6-yl)-4,4,4-trifluoro-3-methylbutanoyl]amino}-4-chlorophenyl)-2-methylpropanoate (Example 82A), according to General Procedure 5, the corresponding carboxylic acid was prepared as a diastereomer mixture. This diastereomer mixture was then separated further by preparative HPLC on a chiral phase [column: Daicel Chiralpak AD-H, 5 μm, 250 mm×20 mm; injection volume: 1.0 ml; temperature: RT; mobile phase: 60% isohexane/40% isopropanol; flow rate: 18 ml/min; detection: 230 nm]. 348 mg of diastereomer mixture gave 160 mg of diastereomer 2, which was purified further by preparative RP-HPLC (mobile phase: acetonitrile/water gradient). This gave 113 mg of the pure title compound.

LC-MS (Method 2): $R_t$=1.27 min; m/z=461 (M+H)$^+$.

$^1$H-NMR (400 MHz, DMSO-d$_6$): δ [ppm]=0.21 (s, 4H), 1.05 (d, 3H), 1.14 (d, 3H), 1.32 (br. s, 4H), 2.55-2.71 (m, about 6H), 2.83-2.93 (m, 1H), 3.01-3.14 (m, 1H), 3.55 (d, 1H), 7.05 (dd, 1H), 7.36-7.48 (m, 2H), 9.62 (s, 1H), 12.19 (br. s, 1H).

$[α]_D^{20}$=+14.0°, c=0.405, chloroform.

Example 47

(+)-(3R)-3-(3-{[(2R,3R)-2-(6-Azaspiro[2.5]oct-6-yl)-4,4,4-trifluoro-3-methylbutanoyl]amino}-4-chlorophenyl)butanoic acid (diastereomer 2)

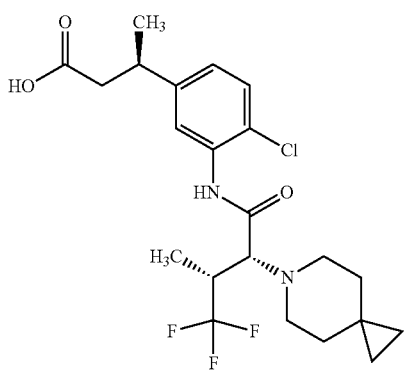 [SMILES: C[C@H](CC(=O)O)c1ccc(Cl)c(NC(=O)[C@@H]([C@@H](C)C(F)(F)F)N2CCC3(CC2)CC3)c1]

The diastereomer mixture of (3R)-3-(3-{[(2R,3R)-2-(6-azaspiro[2.5]oct-6-yl)-4,4,4-trifluoro-3-methylbutanoyl]amino}-4-chlorophenyl)butanoic acid and (3R)-3-(3-{[(2S,3S)-2-(6-azaspiro[2.5]oct-6-yl)-4,4,4-trifluoro-3-methylbutanoyl]amino}-4-chlorophenyl)butanoic acid, prepared according to General Procedure 4 from tert-butyl (3R)-3-{4-chloro-3-[(4,4,4-trifluorovalyl)amino]phenyl}butanoate (Example 62A) and 2,2'-cyclopropane-1,1-diyldiacetaldehyde, was separated by preparative HPLC on a chiral phase [column: Daicel Chiralpak AD-H, 5 μm, 250 mm×20 mm; injection volume: 0.75 ml; temperature: RT; mobile phase: 70% isohexane/30% isopropanol; flow rate: 18 ml/min; detection: 230 nm]. 209 mg of diastereomer mixture gave 76 mg of the title compound as diastereomer 2.

LC-MS (Method 2): $R_t$=1.25 min; m/z=461 (M+H)$^+$.

$^1$H-NMR (400 MHz, DMSO-d$_6$): δ [ppm]=0.21 (s, 4H), 1.14 (d, 3H), 1.20 (d, 3H), 1.24-1.40 (m, 4H), 2.52-2.60 (m, about 4H, obscured), 2.62-2.70 (m, 2H), 3.03-3.19 (m, 2H), 3.56 (d, 1H), 7.12 (dd, 1H), 7.42 (d, 1H), 7.49 (d, 1H), 9.63 (s, 1H).

$[α]_D^{20}$=+5.7°, c=0.363, chloroform.

Example 48

(+)-(3R)-3-(4-Chloro-3-{[(2R,3R)-4,4,4-trifluoro-3-methyl-2-(4-methylpiperidin-1-yl)butanoyl]amino}phenyl)butanoic acid (diastereomer 2)

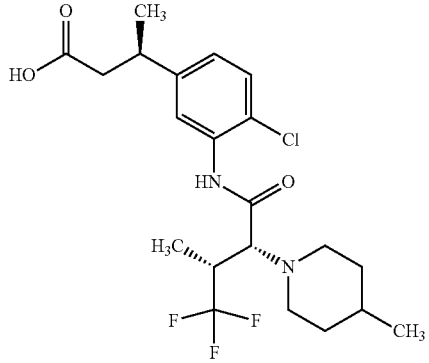 [SMILES: CC1CCN([C@@H](C(=O)Nc2cc([C@H](C)CC(=O)O)ccc2Cl)[C@@H](C)C(F)(F)F)CC1]

The diastereomer mixture of (3R)-3-(4-chloro-3-{[(2R,3R)-4,4,4-trifluoro-3-methyl-2-(4-methylpiperidin-1-yl)butanoyl]amino}phenyl)butanoic acid and (3R)-3-(4-chloro-3-{[(2S,3S)-4,4,4-trifluoro-3-methyl-2-(4-methylpiperidin-1-yl)butanoyl]amino}phenyl)butanoic acid, prepared according to General Procedure 4 from tert-butyl (3R)-3-{4-chloro-3-[(4,4,4-trifluorovalyl)amino]phenyl}butanoate (Example 62A) and 3-methylpentanedial, was separated by preparative HPLC on a chiral phase [column: Daicel Chiralpak AD-H, 5 µm, 250 mm×20 mm; injection volume: 0.75 ml; temperature: RT; mobile phase: 70% isohexane/30% isopropanol; flow rate: 20 ml/min; detection: 230 nm]. 195 mg of diastereomer mixture gave 92 mg of the title compound as diastereomer 2.

LC-MS (Method 5): $R_t$=2.47 min; m/z=449 (M+H)$^+$.

$^1$H-NMR (400 MHz, DMSO-d$_6$): δ [ppm]=0.87 (d, 3H), 0.96-1.08 (m, 1H), 1.11 (d, 3H), 1.15-1.25 (m, 1H), 1.19 (d, 3H), 1.25-1.38 (m, 1H), 1.59 (t, 2H), 2.00-2.13 (m, 1H), 2.53-2.60 (m, about 1H), 2.65 (d, 1H), 2.87-2.95 (m, 1H), 2.99-3.18 (m, 2H), 3.52 (d, 1H), 7.12 (dd, 1H), 7.41 (d, 1H), 7.47 (d, 1H), 9.60 (s, 1H).

Example 49

(−)-(3S)-3-(4-Chloro-3-{[(2R,3R)-4,4,4-trifluoro-3-methyl-2-(4-methylpiperidin-1-yl)butanoyl]amino}phenyl)butanoic acid (diastereomer 1)

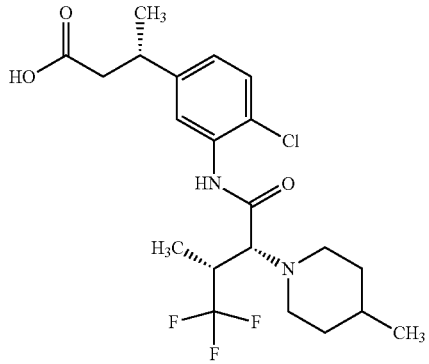 [SMILES: CC1CCN([C@@H](C(=O)Nc2cc([C@@H](C)CC(=O)O)ccc2Cl)[C@@H](C)C(F)(F)F)CC1]

The mixture, obtained above, of (3S)-3-(4-chloro-3-{[(2R,3R)-4,4,4-trifluoro-3-methyl-2-(4-methylpiperidin-1-yl)butanoyl]amino}phenyl)butanoic acid and (3S)-3-(4-chloro-3-{[(2S,3S)-4,4,4-trifluoro-3-methyl-2-(4-methylpiperidin-1-yl)butanoyl]amino}phenyl)butanoic acid (Example 20, diastereomer mixture 1) was separated by preparative HPLC on a chiral phase [column: Daicel Chiralpak AS-H, 5 µm, 250 mm×20 mm; injection volume: 1.2 ml; temperature: RT; mobile phase: 70% isohexane/30% isopropanol; flow rate: 20 ml/min; detection: 230 nm]. 182 mg of diastereomer mixture gave 77 mg of the title compound as diastereomer 1.

LC-MS (Method 4): $R_t$=2.53 min; m/z=449 (M+H)$^+$.

$^1$H-NMR (400 MHz, DMSO-d$_6$): δ [ppm]=0.87 (d, 3H), 1.03-1.24 (m, 8H), 1.24-1.35 (m, 1H), 1.58 (t, 2H), 2.01-2.11 (m, 1H), 2.54-2.60 (m, about 1H), 2.65 (d, 1H), 2.86-2.96 (m, 1H), 2.98-3.18 (m, 2H), 3.52 (d, 1H), 7.12 (dd, 1H), 7.42 (d, 1H), 7.46 (d, 1H), 9.62 (s, 1H), 12.10 (br. s, 1H).

$[α]_D^{20}$=−22.1°, c=0.360, chloroform.

Example 50

(−)-(3S)-3-(3-{[(2R,3R)-2-(6-Azaspiro[2.5]oct-6-yl)-4,4,4-trifluoro-3-methylbutanoyl]amino}-4-chlorophenyl)butanoic acid (diastereomer 1)

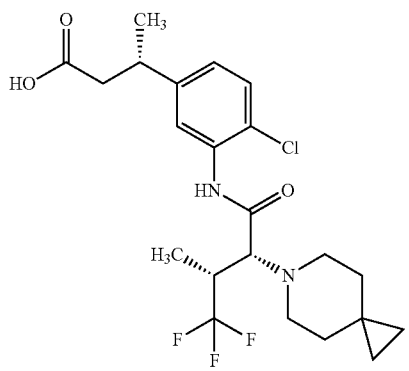 [SMILES: C[C@H]([C@H](C(=O)Nc1cc([C@@H](C)CC(=O)O)ccc1Cl)N1CCC2(CC1)CC2)C(F)(F)F]

The mixture, obtained above, of (3S)-3-(3-{[(2R,3R)-2-(6-azaspiro[2.5]oct-6-yl)-4,4,4-trifluoro-3-methylbutanoyl]amino}-4-chlorophenyl)butanoic acid and (3S)-3-(3-{[(2S,3S)-2-(6-azaspiro[2.5]oct-6-yl)-4,4,4-trifluoro-3-methylbutanoyl]amino}-4-chlorophenyl)butanoic acid (Example 21, diastereomer mixture 1) was separated by preparative HPLC on a chiral phase [column: Daicel Chiralpak AS-H, 5 µm, 250 mm×20 mm; injection volume: 1.0 ml; temperature: RT; mobile phase: 10% isohexane/90% isopropanol; flow rate: 20 ml/min; detection: 230 nm]. 252 mg of diastereomer mixture gave 104 mg of the title compound as diastereomer 1.

LC-MS (Method 4): $R_t$=2.61 min; m/z=461 (M+H)$^+$.

$^1$H-NMR (400 MHz, DMSO-d$_6$): δ [ppm]=0.21 (s, 4H), 1.14 (d, 3H), 1.20 (d, 3H), 1.22-1.40 (m, 4H), 2.50-2.58 (m, about 4H, obscured), 2.61-2.72 (m, 2H), 2.99-3.19 (m, 2H), 3.56 (d, 1H), 7.13 (dd, 1H), 7.43 (d, 1H), 7.48 (d, 1H), 9.64 (s, 1H), 12.10 (br. s, 1H).

$[α]_D^{20}$=17.7°, c=0.440, chloroform.

Example 51

1-(4-Chloro-3-{[(2R,3R)-4,4,4-trifluoro-3-methyl-2-(4-methylpiperidin-1-yl)butanoyl]amino}benzyl)cyclopropanecarboxylic acid

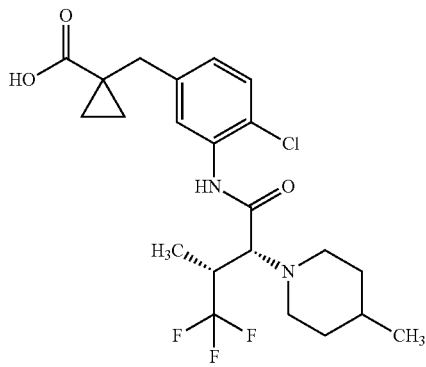 [SMILES: CC1CCN([C@@H](C(=O)Nc2cc(CC3(C(=O)O)CC3)ccc2Cl)[C@@H](C)C(F)(F)F)CC1]

The title compound was obtained according to General Procedure 4 from (+)-tert-butyl 1-(4-chloro-3-{[(3R)-4,4,4-trifluoro-D-valyl]amino}benzyl)cyclopropanecarboxylate (Example 65A) and 3-methylpentanedial.

LC-MS (Method 2): $R_t$=1.24 min; m/z=461 (M+H)$^+$.

$^1$H-NMR (400 MHz, DMSO-d$_6$): δ [ppm]=0.77-0.83 (m, 2H), 0.87 (d, 3H), 0.96-1.34 (m, 6H), 1.10 (d, 3H), 1.59 (t, 2H), 2.06 (t, 1H), 2.60-2.68 (m, 1H), 2.85 (d, 2H), 2.87-2.94 (m, 1H), 2.98-3.11 (m, 1H), 3.49 (d, 1H), 7.11 (dd, 1H), 7.39 (d, 1H), 7.48 (d, 1H), 9.62 (s, 1H), 11.85-12.54 (br. s, 1H).

$[α]_D^{20}$=−4.7°, c=0.325, chloroform.

Example 52 rac-1-(3-{[Cyclopentyl(4-methoxypiperidin-1-yl)acetyl]amino}-4-fluorobenzyl)cyclopropanecarboxylic acid trifluoroacetate

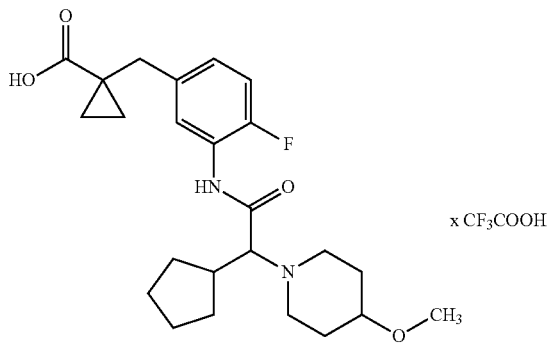 [SMILES: COC1CCN(C(C(=O)Nc2cc(CC3(C(=O)O)CC3)ccc2F)C2CCCC2)CC1]

20.1 mg (0.04 mmol) of rac-tert-butyl 1-(3-{[cyclopentyl(4-methoxypiperidin-1-yl)acetyl]amino}-4-fluorobenzyl)cyclopropanecarboxylate (Example 95A) were dissolved in 2.4 ml of 20% strength trifluoroacetic acid in dichloromethane and stirred at RT for 5 h. The mixture was then concentrated on a rotary evaporator and the residue was purified by preparative HPLC (RP18 column; mobile phase: acetonitrile/water gradient with addition of 0.1% TFA, 10:90→95:5; run time 38 min). This gave 6.8 mg (30% of theory) of the title compound.

LC-MS (Method 5): $R_t$=0.86 min; m/z=433.1 (M+H)$^+$.

$^1$H-NMR (400 MHz, DMSO-d$_6$): δ [ppm]=0.80-0.86 (m, 2H), 1.10-1.16 (m, 2H), 1.35-1.73 (m, 8H), 1.79-2.07 (m, 4H), 2.08-2.21 (m, 1H), 2.86 (br. s, 2H), 3.26 (s, 3H), 3.29-3.35 (m, 2H), 4.06-4.15 (m, 1H), 7.12-7.27 (m, 2H), 7.67 (t, 1H), 9.61 (br. s, 1H), 10.43-10.51 (m, 1H) [further signals hidden under solvent peaks].

Example 53 rac-1-(3-{[Cyclopentyl(3,4-dihydroisoquinolin-2(1H)-yl)acetyl]amino}-4-fluorobenzyl)cyclopropanecarboxylic acid trifluoroacetate

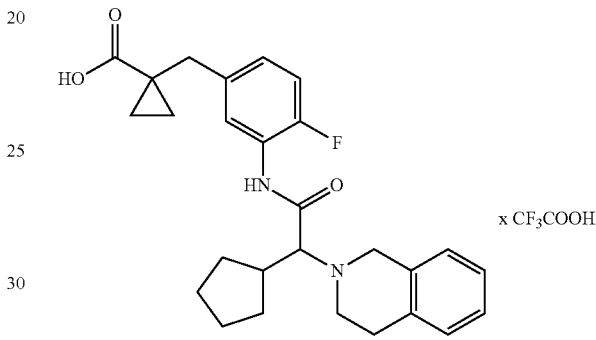

101 mg (0.2 mmol) of rac-tert-butyl 1-(3-{[cyclopentyl(3,4-dihydroisoquinolin-2(1H)-yl)acetyl]amino}-4-fluorobenzyl)cyclopropanecarboxylate (Example 96A) were dissolved in 11.5 ml of 20% strength trifluoroacetic acid in dichloromethane and stirred at RT for 5 h. The mixture was then concentrated on a rotary evaporator and the residue was purified by preparative HPLC (RP18 column; mobile phase: acetonitrile/water gradient with addition of 0.1% TFA, 10:90→95:5; run time 38 min). This gave 14.4 mg (13% of theory) of the title compound.

LC-MS (Method 2): $R_t$=0.91 min; m/z=451.3 (M+H)$^+$.

$^1$H-NMR (400 MHz, DMSO-d$_6$): δ [ppm]=0.79-0.87 (m, 2H), 1.07-1.14 (m, 2H), 1.38-1.50 (m, 1H), 1.51-1.69 (m, 5H), 1.70-1.81 (m, 1H), 1.90-2.04 (m, 1H), 2.86 (s, 2H), 3.05-3.21 (m, 2H), 4.20-4.36 (m, 1H), 4.50-4.64 (m, 1H), 7.02-7.37 (m, 6H), 7.63-7.73 (m, 1H) [further signals hidden under solvent peaks].

B. ASSESSMENT OF PHARMACOLOGICAL EFFICACY

The pharmacological efficacy of the inventive compounds can be shown in the following assays:

B-1. Stimulation of Recombinant Soluble Guanylate Cyclase (sGC) In Vitro

The investigations on the stimulation of recombinant soluble guanylate cyclase (sGC) by the compounds according to the invention with and without sodium nitroprusside and with and without the haem-dependent sGC inhibitor 1H-1,2,4-oxadiazolo[4,3-a]quinoxalin-1-one (ODQ) are carried out by the method described in detail in the following literature reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. Haem-free guanylate cyclase is obtained by adding Tween 20 to the sample buffer (final concentration 0.5%).

Activation of sGC by a test substance is stated as x-fold stimulation of basal activity. The result for Example 25 is shown in Table 1:

TABLE 1

Stimulation (x-times) by Example 25 of recombinant soluble guanylate cyclase (sGC) in vitro

| Concentration of Example 25 [µM] | Haem-containing sGC | | | Haem-free |
|---|---|---|---|---|
| | Basal (n = 2) | +0.01 µM DEA/NO | +10 µM ODQ | sGC Basal (n = 2) |
| 0 | 1.0 ± 0.0 | 11.2 ± 5.0 | 3.6 ± 1.2 | 1.0 ± 0.0 |
| 0.01 | 0.9 ± 0.2 | 11.4 ± 3.9 | 2.3 ± 0.1 | 1.9 ± 0.8 |
| 0.1 | 0.9 ± 0.0 | 11.9 ± 4.2 | 2.7 ± 0.2 | 2.4 ± 0.8 |
| 1.0 | 2.8 ± 0.4 | 12.0 ± 3.9 | 10.5 ± 2.4 | 7.3 ± 3.6 |
| 10 | 8.6 ± 0.2 | 15.1 ± 2.9 | 32.5 ± 5.4 | 26.6 ± 7.3 |

[DEA/NO = 2-(N,N-diethylamino)diazenolate 2-oxide;
ODQ = 1H-1,2,4-oxadiazolo[4,3-a]quinoxalin-1-one].

It can be seen from Table 1 that stimulation both of the haem-containing and of the haem-free enzyme is achieved. Furthermore, the combination of Example 25 with 2-(N,N-diethylamino)diazenolate 2-oxide (DEA/NO), an NO donor, shows no synergistic effect, i.e. the activity of DEA/NO is not potentiated as would be expected for an sGC activator acting via a haem-dependent mechanism. In addition, the activity of the sGC activator according to the invention is not blocked but, in contrast, even enhanced by 1H-1,2,4-oxadiazolo[4,3-a]quinoxalin-1-one (ODQ), a heam-dependent inhibitor of soluble guanylate cyclase. Accordingly, the results in Table 1 confirm the mechanism of action of the compounds according to the invention as activators of soluble guanylate cyclase.

B-2. Effect on a Recombinant Guanylate Cyclase Reporter Cell Line

The cellular activity of the compounds according to the invention is determined using a recombinant guanylate cyclase reporter cell line, as described in F. Wunder et al., *Anal. Biochem.* 339, 104-112 (2005).

Representative results for the compounds according to the invention are listed in Table 2:

TABLE 2 sGC-activating activity in the CHO reporter cell in vitro

| Example No. | MEC [nM] |
|---|---|
| 1 | 20 |
| 2 | 20 |
| 3 | 60 |
| 4 | 5 |
| 5 | 30 |
| 6 | 60 |
| 7 | 60 |
| 8 | 0.3 |
| 9 | 10 |
| 10 | 30 |
| 11 | 10 |
| 12 | 30 |
| 13 | 30 |
| 14 | 30 |
| 15 | 10 |
| 16 | 50 |
| 17 | 3 |
| 18 | 30 |
| 19 | 3 |

TABLE 2-continued sGC-activating activity in the CHO reporter cell in vitro

| Example No. | MEC [nM] |
|---|---|
| 22 | 300 |
| 23 | 3 |
| 24 | 100 |
| 25 | 1 |
| 26 | 1 |
| 27 | 10 |
| 28 | 20 |
| 29 | 30 |
| 30 | 300 |
| 31 | 100 |
| 32 | 30 |
| 33 | 300 |
| 34 | 10 |
| 35 | 30 |
| 36 | 2.3 |
| 37 | 200 |
| 38 | 300 |
| 39 | 0.3 |
| 40 | 1000 |
| 41 | 10 |
| 42 | 300 |
| 43 | 10 |
| 44 | 1000 |
| 45 | 3 |
| 46 | 10 |
| 47 | 1 |
| 48 | 3 |
| 49 | 3 |
| 50 | 10 |
| 51 | 1 |
| 52 | 3000 |
| 53 | 100 |

(MEC = minimum effective concentration).

B-3. Stimulation of sGC Enzyme Activity

Soluble guanylate cyclase (sGC) converts on stimulation GTP into cGMP and pyrophosphate (PPi). PPi is detected with the aid of the assay described below. The signal produced in the assay increases as the reaction progresses and serves as a measure of the sGC enzyme activity under the given stimulation.

To carry out the assay, 29 µl of enzyme solution [0-10 nM soluble guanylate cyclase (prepared according to Hönicka et al., *J. Mol. Med.* 77, 14-23 (1999)) in 50 mM TEA, 2 mM $MgCl_2$, 0.1% BSA (fraction V), 0.005% Brij®, pH 7.5] are initially introduced into a microplate, and 1 µl of the substance to be tested (as a serially diluted solution in DMSO) is added. The mixture is incubated at room temperature for 10 min. Then 20 µl of detection mix [1.2 nM Firefly Luciferase (*Photinus pyralis* luciferase, Promega), 29 µM dehydroluciferin (prepared according to Bitler & McElroy, *Arch. Biochem. Biophys.* 72, 358 (1957)), 122 µM luciferin (Promega), 153 µM ATP (Sigma) and 0.4 mM DTT (Sigma) in 50 mM TEA, 2 mM $MgCl_2$, 0.1% BSA (fraction V), 0.005% Brij®, pH 7.5] are added. The enzyme reaction is started by adding 20 µl of substrate solution [1.25 mM guanosine 5'-triphosphate (Sigma) in 50 mM TEA, 2 mM $MgCl_2$, 0.1% BSA (fraction V), 0.005% Brij®, pH 7.5] and measured continuously in a luminometer. The extent of the stimulation by the substance to be tested can be determined relative to the signal of the unstimulated reaction.

The activation of haem-free guanylate cyclase is examined by addition of 25 µM of 1H-1,2,4-oxadiazolo[4,3-a]quinoxalin-1-one (ODQ) to the enzyme solution and subsequent incubation for 30 minutes and compared to the stimulation of the native enzyme.

Representative results for the compounds according to the invention are listed in Table 3:

TABLE 3

Activating action at the sGC enzyme in vitro

| Example No. | MEC [nM] | $EC_{50}$ [nM] |
|---|---|---|
| 8 | 1.2 | 21 |
| 11 | 17 | 390 |
| 18 | 6.9 | 540 |
| 25 | 2.2 | 15 |
| 26 | 0.8 | 10 |
| 27 | 10.5 | 210 |
| 34 | 10.5 | 90 |
| 36 | 3 | 25 |
| 39 | 1.1 | 7.9 |
| 46 | 17 | 210 |
| 47 | 3.9 | 81 |
| 48 | 1.1 | 33 |
| 51 | 1.2 | n.d. |
| 53 | 160 | 840 |

(MEC = minimum effective concentration;
$EC_{50}$ = half-maximal effective concentration;
n.d. = not determined).

B-4. Vasorelaxant Effect In Vitro

Rabbits are anaesthetized by intravenous injection of thiopental sodium or killed (about 50 mg/kg) and exsanguinated. The arteria saphena is removed and divided into 3 mm wide rings. The rings are individually mounted on in each case one triangular pair of hooks, open at the end, made of 0.3 mm strong special wire (Remanium®). Under pretension, each ring is transferred into 5 ml organ baths containing a warm, carbogen-aerated Krebs-Henseleit solution at 37° C. having the following composition: NaCl 119 mM; KCl 4.8 mM; $CaCl_2 \times 2$ $H_2O$ 1 mM; $MgSO_4 \times 7$ $H_2O$ 1.4 mM; $KH_2PO_4$ 1.2 mM; $NaHCO_3$ 25 mM; glucose 10 mM; bovine serum albumin 0.001%. The contractile force is determined with Statham UC2 cells, amplified and digitalized using A/D transducers (DAS-1802 HC, Keithley Instruments Munich), and recorded in parallel on linear recorders. Contractions are induced by addition of phenylephrin.

After several (in general 4) control cycles, the substance to be investigated is added in each further passage in increasing dosage, and the height of the contraction achieved under the influence of the test substance is compared with the height of the contraction achieved in the last preliminary passage. From this, the concentration which is necessary in order to reduce the contraction achieved in the preliminary control by 50% ($IC_{50}$) is calculated. The standard administration volume is 5 µl. The proportion of DMSO in the bath solution corresponds to 0.1%.

B-5. Radiotelemetric Measurement of Blood Pressure and Heart Rate of Conscious SH Rats A commercially available telemetry system from Data Sciences International DSI, USA, is employed for the measurements on conscious SH rats described below.

The system consists of 3 main components: (1) implantable sender, (2) receiver which are, via a multiplexer, linked to a (3) data aquisition computer. The telemetry system makes it possible to continuously record blood pressure and heart rate of conscious animals in their usual habitat.

The studies are conducted on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 am and at 7.00 pm.

The telemetry transmitters used (TAM PA-C40, DSI) are surgically implanted under aseptic conditions in the experimental animals at least 14 days before the first experimental use. The animals instrumented in this way can be used repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and the wound is closed layer by layer. An antibiotic (Tardomyocel COMP, Bayer AG, 1 ml/kg s.c.) is administered postoperatively for prophylaxis of infection.

Test Procedure:

The substances to be studied are administered orally by gavage to a group of animals in each case (n=6). In accordance with an administration volume of 5 ml/kg of body weight, the test substances are dissolved in suitable solvent mixtures or suspended in 0.5% tylose. A solvent-treated group of animals is used as control.

The telemetry measuring system is configured for 24 animals. Each experiment is registered under an experiment number.

Each of the instrumented rats living in the system is assigned a separate receiving antenna (1010 Receiver, DSI). The implanted senders can be activated externally via an installed magnetic switch and are switched to transmission during the pre-run of the experiment. The signals emitted can be detected online by a data acquisition system (Dataquest™ A.R.T. for Windows, DSI) and processed accordingly. The data are stored in each case in a file created for this purpose and bearing the experiment number.

In the standard procedure, the following are measured for 10-second periods in each case: (1) systolic blood pressure (SBP), (2) diastolic blood pressure (DBP), (3) mean arterial pressure (MAP) and (4) heart rate (HR).

The acquisition of measurements is repeated under computer control at 5-minute intervals. The source data obtained as absolute values are corrected in the diagram with the currently measured barometric pressure and stored as individual data. Further technical details are given in the documentation from the manufacturer company (DSI).

Administration of the test substances takes place at 9 a.m. on the day of the experiment. Following the administration, the parameters described above are measured over 24 hours. After the end of the experiment, the acquired individual data are sorted using the analysis software (Dataquest™ A.R.T. Analysis). The blank value is taken at the time 2 hours before administration, and the selected data set therefore encompasses the period from 7:00 am on the day of the experiment to 9:00 am on the following day.

The data are smoothed over a predefinable period by determination of the average (15-minute average, 30-minute average) and transferred as a text file to a storage medium. The measured values presorted and compressed in this way are transferred to Excel templates and tabulated.

C. WORKING EXAMPLES FOR PHARMACEUTICAL COMPOSITIONS

The compounds according to the invention can be converted to pharmaceutical formulations as follows:

Tablet:

Composition:

100 mg of the compound according to the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm

Production:

The mixture of inventive compound, lactose and starch is granulated with a 5% solution (w/w) of the PVP in water. The granules are dried and then mixed with the magnesium stearate for 5 minutes. This mixture is compressed in a conventional tablet press (see above for format of the tablet). The guide value used for the pressing is a pressing force of 15 kN.

Suspension which can be Administered Orally:

Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol; the compound according to the invention is added to the suspension. The water is added while stirring. The mixture is stirred for about 6 h before swelling of the Rhodigel is complete.

Solution for Oral Administration:

Composition:

500 mg of the compound according to the invention, 2.5 g of polysorbate and 97 g of polyethylene glycol 400. 20 g of oral solution correspond to a single dose of 100 mg of the compound according to the invention.

Production:

The compound according to the invention is suspended in the mixture of polyethylene glycol and polysorbate with stirring. The stirring operation is continued until solution of the compound according to the invention is complete.

i.v. Solution:

The compound according to the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

The invention claimed is:

1. A compound of the formula (I)

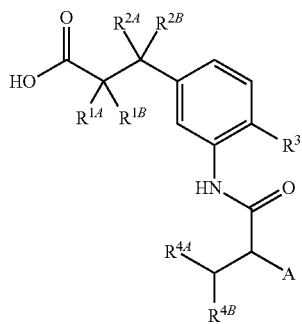

(I)

in which
R$^{1A}$ and R$^{1B}$ independently of one another represent hydrogen, methyl, ethyl or n-propyl
or
are attached to one another and together with the carbon atom to which they are attached form a cyclopropyl or cyclobutyl ring,
R$^{2A}$ represents hydrogen, methyl, ethyl, n-propyl, isopropyl, cyclopropyl, methoxy, ethoxy or cyclopropyloxy,
R$^{2B}$ represents hydrogen or methyl,
or
R$^{2A}$ and R$^{2B}$ are attached to one another and together with the carbon atom to which they are attached form a cyclopropyl or cyclobutyl ring,
R$^{3}$ represents hydrogen, fluorine, chlorine, methyl, trifluoromethyl or ethyl,
R$^{4A}$ and R$^{4B}$ independently of one another represent methyl, trifluoromethyl or ethyl
or
are attached to one another and together with the carbon atom to which they are attached form a cyclopropyl, cyclobutyl or cyclopentyl ring which may be substituted up to two times by fluorine
and
A represents an optionally substituted or fused piperidine ring of the formula

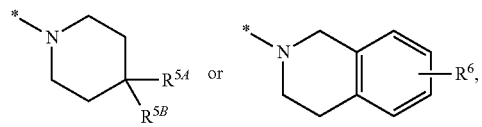

wherein
* denotes the point of attachment to the remainder of the molecule,
R$^{5}$ represents hydrogen, (C$_1$-C$_4$)-alkyl, cyclopropyl, cyclobutyl, methoxy, ethoxy or phenyl, where (C$_1$-C$_4$)-alkyl for its part may be substituted up to three times by fluorine,
R$^{5B}$ represents hydrogen or methyl,
or
R$^{5A}$ and R$^{5B}$ are attached to one another and together with the carbon atom to which they are attached form a cyclopropyl or cyclobutyl ring,
and
R$^{6}$ represents hydrogen, fluorine, chlorine, methyl or trifluoromethyl,
or a salt, solvate, or a solvate of the salt thereof.

2. The compound of claim 1 in which
R$^{1A}$ represents hydrogen or methyl,
R$^{1B}$ represents hydrogen,
or
R$^{1A}$ and R$^{1B}$ are attached to one another and together with the carbon atom to which they are attached form a cyclopropyl or cyclobutyl ring,
R$^{2A}$ represents hydrogen, methyl, ethyl, isopropyl or cyclopropyl,
R$^{2B}$ represents hydrogen,
or
R$^{2A}$ and R$^{2B}$ are attached to one another and together with the carbon atom to which they are attached form a cyclopropyl ring,
R$^{3}$ represents fluorine, chlorine or methyl,
R$^{4A}$ represents methyl,
R$^{4B}$ represents trifluoromethyl,
or
R$^{4A}$ and R$^{4B}$ are attached to one another and together with the carbon atom to which they are attached form a cyclopentyl ring which may be substituted up to two times by fluorine,
and
A represents an optionally substituted or fused piperidine ring of the formula

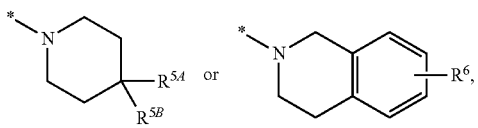

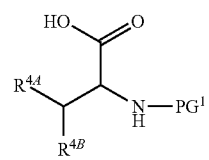  (II)

wherein

* denotes the point of attachment to the remainder of the molecule, $R^{5A}$ represents hydrogen, methyl, trifluoromethyl, ethyl, isopropyl or cyclopropyl, $R^{5B}$ represents hydrogen or $R^{5A}$ and $R^{5B}$ are attached to one another and together with the carbon atom to which they are attached form a cyclopropyl ring, and $R^6$ represents hydrogen or fluorine, or a salt, solvate, or a solvate of the salt thereof.

3. The compound of claim 1 in which $R^{1A}$ represents hydrogen or methyl, $R^{1B}$ is hydrogen, or $R^{1A}$ and $R^{1B}$ are attached to one another and together with the carbon atom to which they are attached form a cyclopropyl ring, $R^{2A}$ represents hydrogen or methyl, $R^{2B}$ represents hydrogen, $R^3$ represents fluorine or chlorine, $R^{4A}$ represents methyl, $R^{4B}$ represents trifluoromethyl, and A represents an optionally substituted piperidine ring of the formula

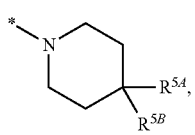

wherein

* denotes the point of attachment to the remainder of the molecule, $R^{5A}$ represents hydrogen, methyl, trifluoromethyl or ethyl, $R^{5B}$ represents hydrogen or $R^{5A}$ and $R^{5B}$ are attached to one another and together with the carbon atom to which they are attached form a cyclopropyl ring, or a salt, solvate, or a solvate of the salt thereof.

4. A process for preparing the compound of claim 1, comprising coupling a protected α-aminocarboxylic acid of the formula (II)

in which $R^{4A}$ and $R^{4B}$ have the meanings given in claim 1 and $PG^1$ represents a suitable amino protective group, in an inert solvent with the aid of a condensing agent in the presence of a base with an amine of the formula (III)

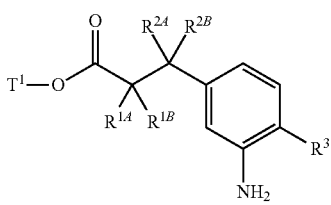  (III)

in which $R^{1A}$, $R^{1B}$, $R^{2A}$, $R^{2B}$ and $R^3$ have the meanings given in claim 1 and $T^1$ represents $(C_1-C_4)$-alkyl or benzyl, to give a carboxamide of the formula (IV)

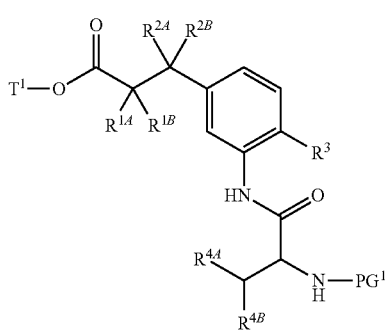  (IV)

in which $PG^1$, $R^{1A}$, $R^{1B}$, $R^{2A}$, $R^{2B}$, $R^3$, $R^{4A}$, $R^{4B}$ and $T^1$ have the meanings given above, then, removing the protective group $PG^1$ to release the amine compound (V)

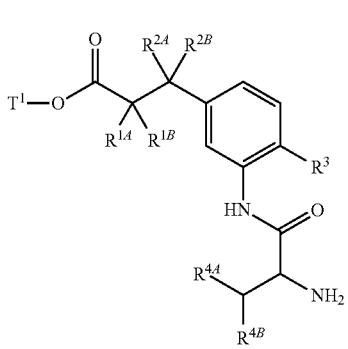  (V)

in which $R^{1A}$, $R^{1B}$, $R^{2A}$, $R^{2B}$, $R^3$, $R^{4A}$, $R^{4B}$ and $T^1$ have the meanings given above
then reacting the amine compound (V) in the presence of a suitable reducing agent with a dialdehyde of the formula (VI)

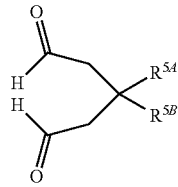

(VI)

in which $R^{5A}$ and $R^{5B}$ have the meanings given in claim 1, to give a mixture (with varying proportions) of the two cyclization products (VII) and (VIII)

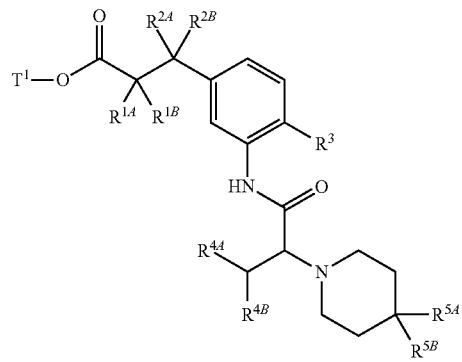

(VII)

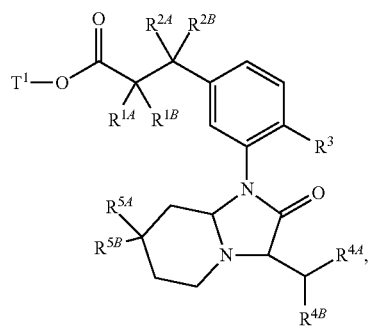

(VIII)

in which $R^{1A}$, $R^{1B}$, $R^{2A}$, $R^{2B}$, $R^3$, $R^{4A}$, $R^{4B}$, $R^{5A}$, $R^{5B}$ and $T^1$ have the meanings given above,
then treating the mixture with an excess of triethylsilane in trifluoroacetic acid so that the cyclization product (VIII) is also converted into the cyclization product (VII), and removing the ester radical $T^1$ by basic or acidic solvolysis or, in the case that $T^1$ represents benzyl, also by hydrogenolysis, giving the carboxylic acid of the formula (I-A)

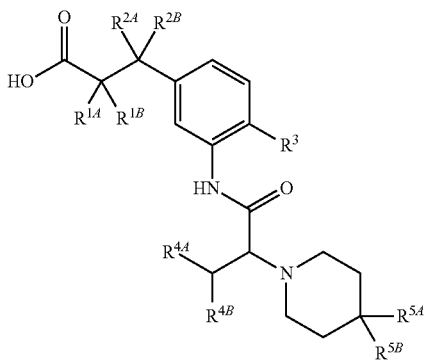

(I-A)

in which $R^{1A}$, $R^{1B}$, $R^{2A}$, $R^{2B}$, $R^3$, $R^{4A}$, $R^{4B}$, $R^{5A}$ and $R^{5B}$ have the meanings given above;
wherein the resulting compound of the formula (I-A) is optionally separated into their enantiomers and/or diastereomers and/or converted using the appropriate (i) solvents and/or (ii) bases or acids into the solvates, salts and/or solvates of the salts thereof.

5. A pharmaceutical composition comprising the compound of claim 1 in combination with one or more inert, nontoxic, pharmaceutically suitable excipients.

6. A pharmaceutical composition comprising the compound of claim 1 in combination with one or more further active compounds selected from the group consisting of organic nitrates, NO donors, cGMP-PDE inhibitors, stimulators of guanylate cyclase, antithrombotic agents, hypotensive agents and lipid metabolism modifiers.

7. A pharmaceutical composition comprising the compound as defined in claim 3 in combination with one or more inert, nontoxic, pharmaceutically suitable excipients.

8. A method for treatment of heart failure, angina pectoris, hypertension, pulmonary hypertension, thromboembolic disorders, ischaemias, vascular disorders, impaired microcirculation, renal insufficiency, fibrotic disorders and arteriosclerosis in humans and animals comprising administering an effective amount of at least one compound as defined in claim 1 to a patient in need thereof.

9. A method for treatment of heart failure, angina pectoris, hypertension, pulmonary hypertension, thromboembolic disorders, ischaemias, vascular disorders, impaired microcirculation, renal insufficiency, fibrotic disorders and arteriosclerosis in humans and animals comprising administering an effective amount of the pharmaceutical composition of claim 5 to a patient in need thereof.

10. A method for treatment of heart failure, angina pectoris, hypertension, pulmonary hypertension, thromboembolic disorders, ischaemias, vascular disorders, impaired microcirculation, renal insufficiency, fibrotic disorders and arteriosclerosis in humans and animals comprising administering an effective amount of the pharmaceutical composition of claim 7 to a patient in need thereof.

* * * * *